United States Patent
Patel et al.

(10) Patent No.: US 12,168,003 B2
(45) Date of Patent: *Dec. 17, 2024

(54) SELECTIVE INHIBITION OF T FOLLICULAR HELPER CELLS FOR TREATMENT OF AUTOIMMUNE DISORDERS

(71) Applicant: NEW YORK UNIVERSITY, New York, NY (US)

(72) Inventors: Preeyam S. Patel, New York, NY (US); Robert J. Schneider, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/165,113

(22) Filed: Feb. 6, 2023

(65) Prior Publication Data

US 2023/0233535 A1 Jul. 27, 2023

Related U.S. Application Data

(63) Continuation of application No. 17/110,023, filed on Dec. 2, 2020, now Pat. No. 11,602,524.

(60) Provisional application No. 62/942,503, filed on Dec. 2, 2019.

(51) Int. Cl.
| | | |
|---|---|---|
| C12N 15/113 | (2010.01) | |
| A61K 31/426 | (2006.01) | |
| C12Q 1/68 | (2018.01) | |

(52) U.S. Cl.
CPC .......... *A61K 31/426* (2013.01); *C12N 15/113* (2013.01); *C12N 2310/11* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| 11,602,524 B2 | 3/2023 | Patel et al. |
| 2012/0177597 A1 | 7/2012 | Ueno et al. |

FOREIGN PATENT DOCUMENTS

| WO | 2014/074852 A1 | 5/2014 |
| WO | 2015/050957 A2 | 4/2015 |

OTHER PUBLICATIONS

Extended European Search Report in EP Application No. 20896446.0 (mailed Sep. 19, 2023).
Klassen et al., "Ribavirin Treatment in Murine Autoimmune Disease," Arthritis and Rheumatism 22(2): 145-154 (1979).
Gensous et al., "T Follicular Helper Cells in Autoimmune Disorders," Front. Immunol. 17(9):1637 (2018).
Chiang et al., "Abstract 1302: Targeting Hormone Receptor-Dependent Cancers with Potent, Selective and Orally-Available Small Molecule Inhibitors of eIF4E," Proceedings of the American Association for Cancer Research Annual Meeting 2019; Mar. 29-Apr 3, 2019; Atlanta, GA. Philadelphia (PA): AACR Cancer Res 2019; 79(13 Suppl): Abstract nr 1302. (2019).
Yl et al., "The mTORC1-4E-BP-eIF4E Axis Controls de Novo Bcl6 Protein Synthesis in T Cells and Systemic Autoimmunity," Nat. Commun. 8:254-254 (2017).
Bjur et al., "Distinct Translational Control in CD4+ T Cell Subsets," PLOS Genet. 9(5):e1003494 (2013).
International Search Report and Written Opinion for PCT/US2020/062892 mailed Mar. 4, 2021.

*Primary Examiner* — Sean McGarry
(74) *Attorney, Agent, or Firm* — Troutman Pepper Hamilton Sanders LLP

(57) ABSTRACT

Disclosed herein is a method of inhibiting T Follicular Helper (TFH) cell-mediated differentiation and/or activation in a subject. This method involves administering to a subject in need of treatment for an autoimmune disorder a eukaryotic translation initiation factor 4E (eIF4E) inhibitor to inhibit TFH cell-mediated differentiation and/or activation in the subject. Also disclosed is a method of inhibiting T Follicular Helper (THF) cell differentiation or TFH cell activity.

15 Claims, 36 Drawing Sheets

Specification includes a Sequence Listing.

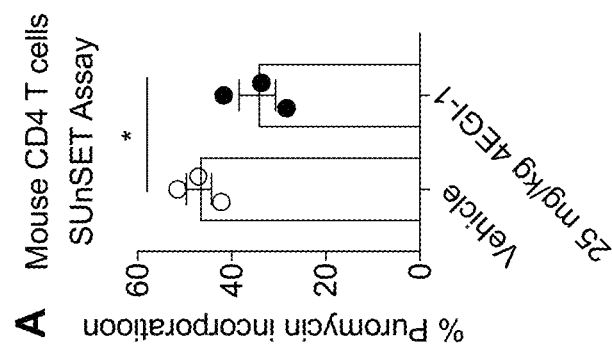
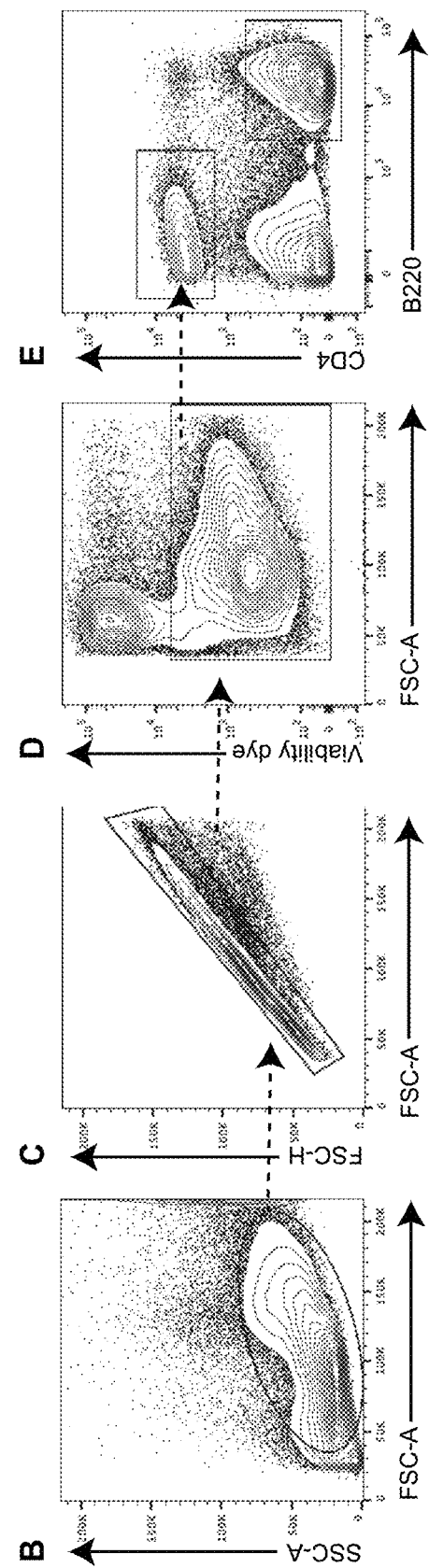
FIGs. 1A-1E

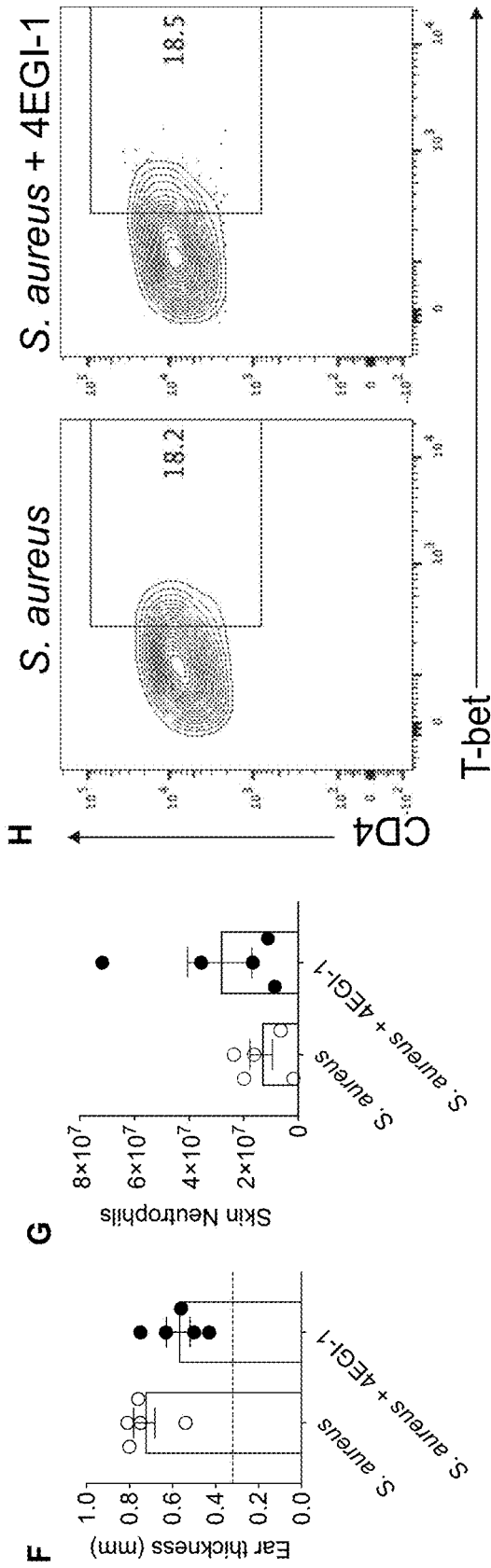
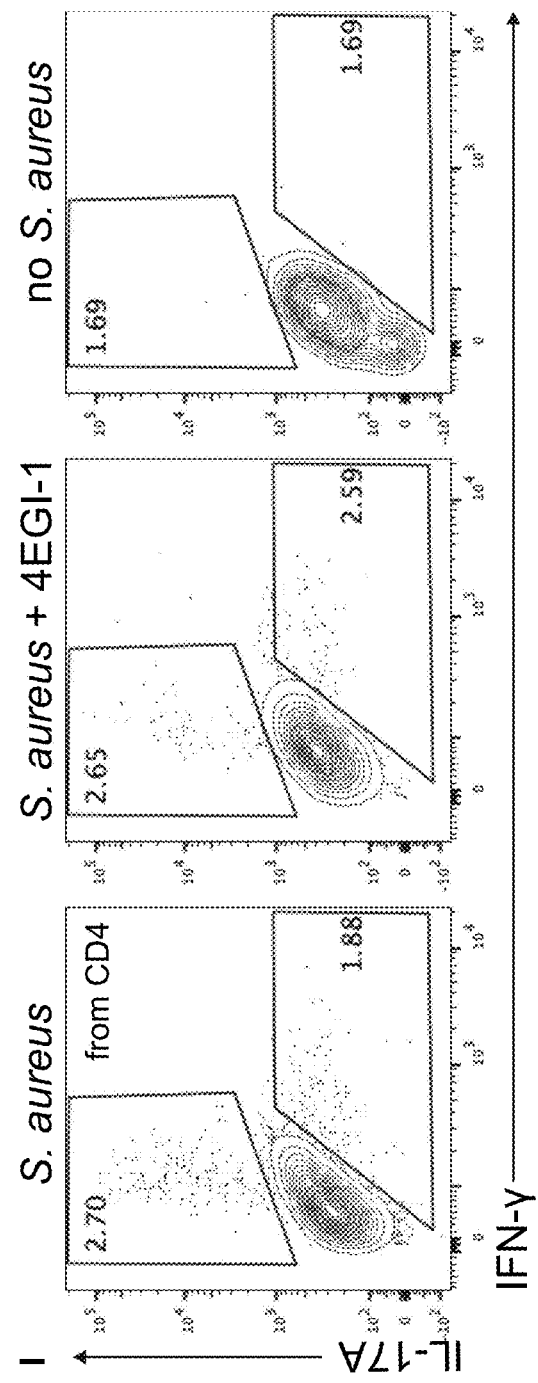
FIGs. 1F-1I

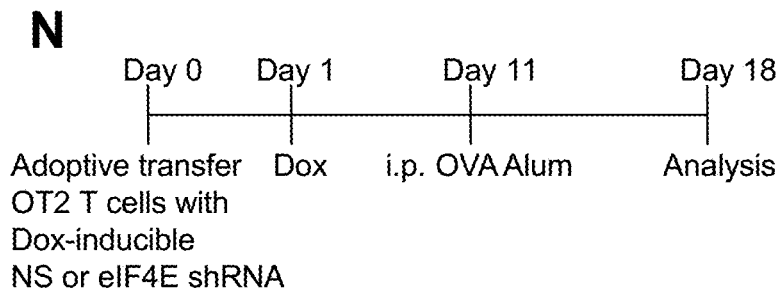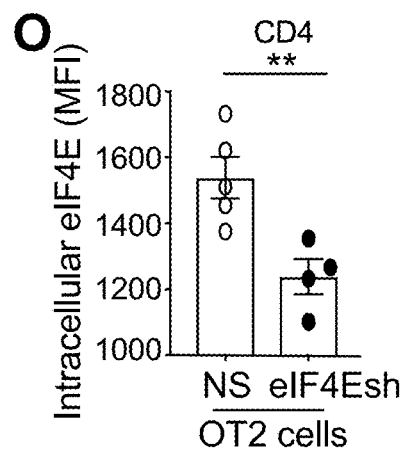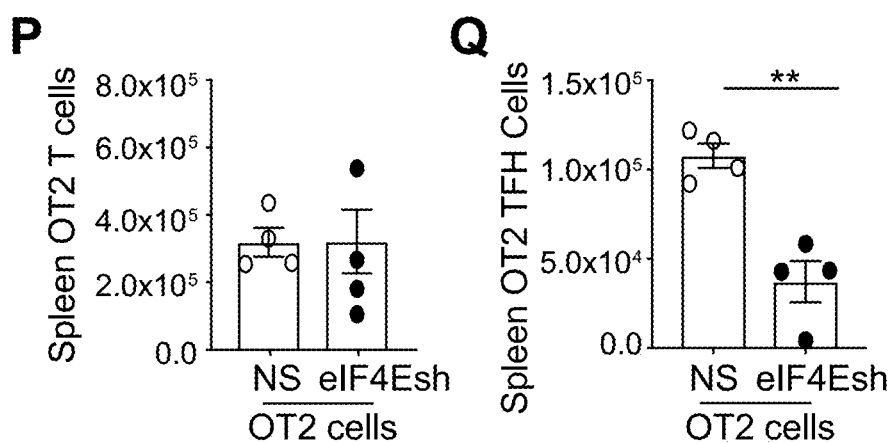
FIGs. 2N-2Q

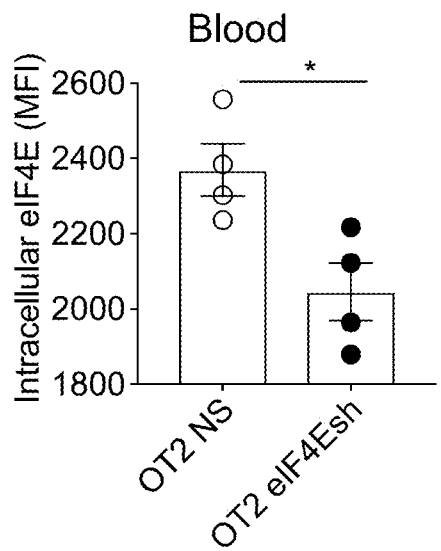
FIG. 3K
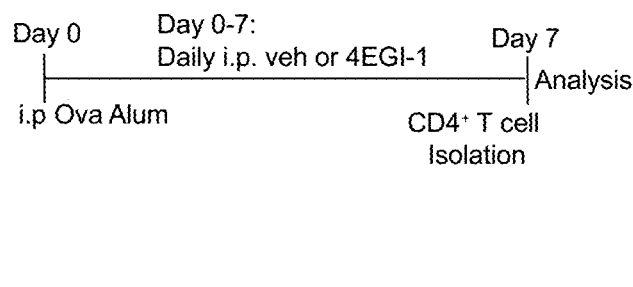
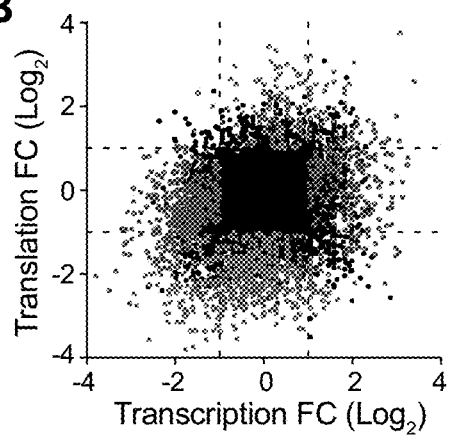
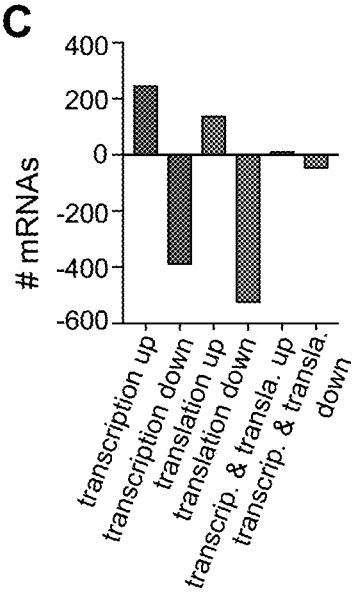
FIGs. 4A-4C

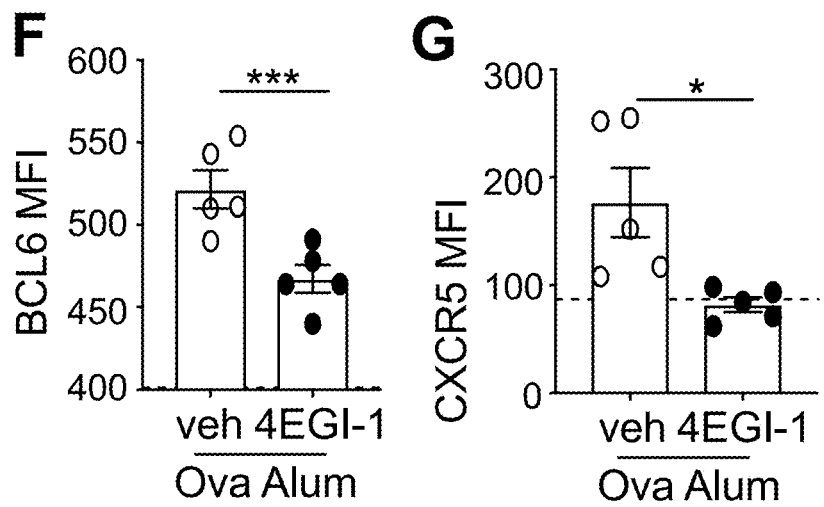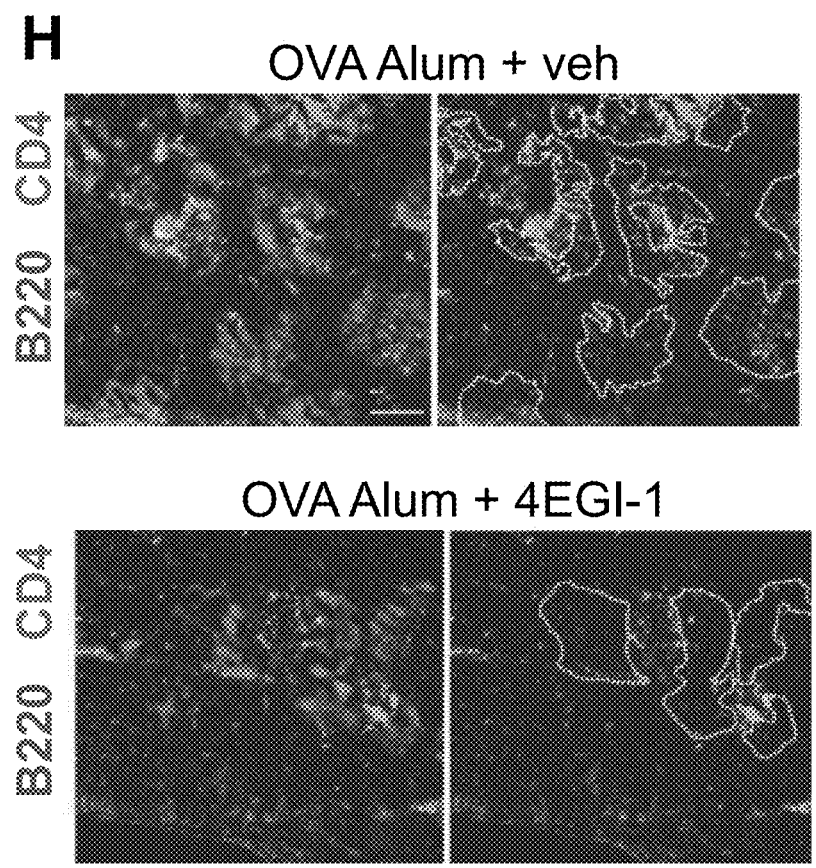
FIGs. 5F-5H

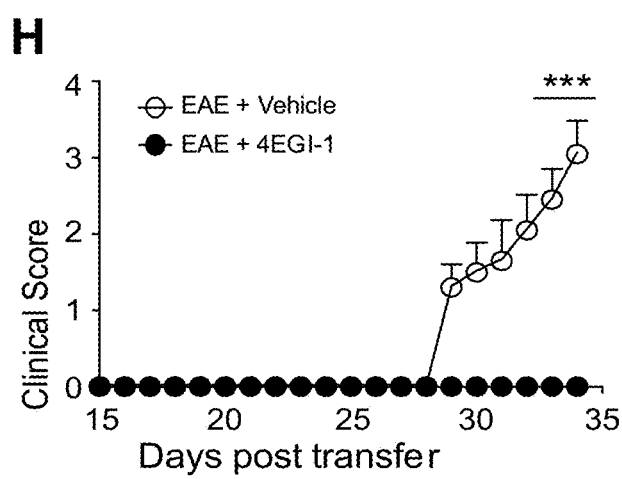
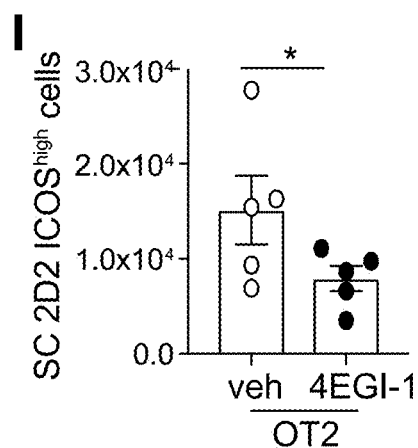
FIGs. 13G-13I

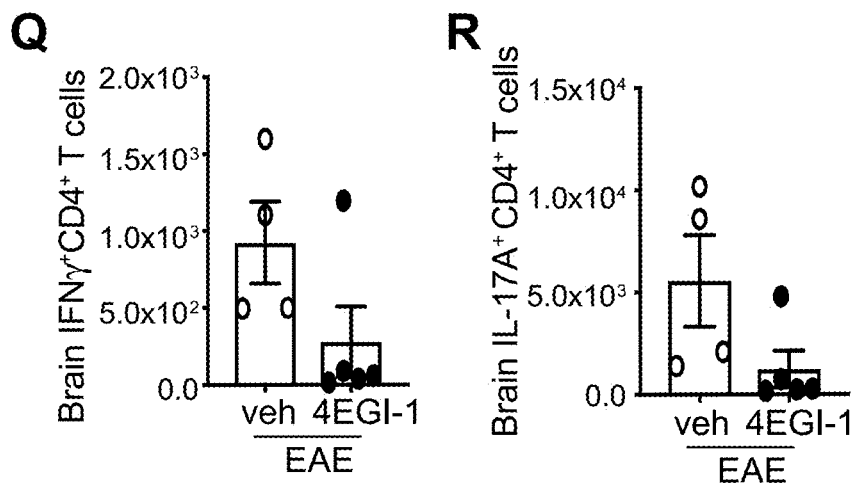
*FIGS. 14Q-14R*
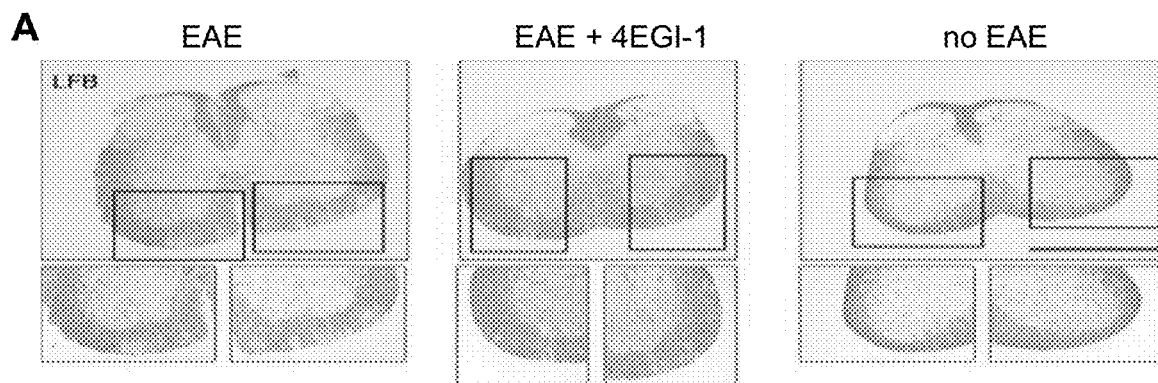
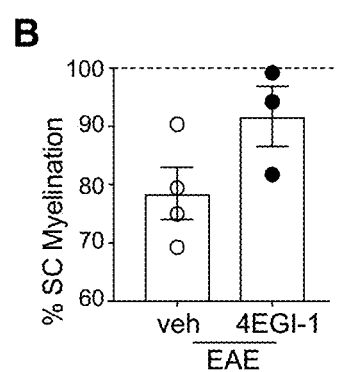
*FIGS. 15A-15B*

SEQUENCE LISTING

```
Sequence total quantity: 6
SEQ ID NO: 1            moltype = DNA  length = 20
FEATURE                 Location/Qualifiers
misc_feature            1..20
                        note = eIF4E-ASO1
modified_base           1..5
                        mod_base = OTHER
                        note = 2-methoxyethyl
modified_base           16..20
                        mod_base = OTHER
                        note = 2-methoxyethyl
source                  1..20
                        mol_type = other DNA
                        organism = synthetic construct
SEQUENCE: 1
tgctatctta tcacctttag                                               20

SEQ ID NO: 2            moltype = DNA  length = 20
```

```
FEATURE                 Location/Qualifiers
misc_feature            1..20
                        note = eIF4E-ASO2
modified_base           1..5
                        mod_base = OTHER
                        note = 2-methoxyethyl
modified_base           16..20
                        mod_base = OTHER
                        note = 2-methoxyethyl
source                  1..20
                        mol_type = other DNA
                        organism = synthetic construct
SEQUENCE: 2
ggcgaatgag acttctctta                                               20

SEQ ID NO: 3            moltype = DNA  length = 20
FEATURE                 Location/Qualifiers
misc_feature            1..20
                        note = eIF4E-ASO3
modified_base           1..5
                        mod_base = OTHER
                        note = 2-methoxyethyl
modified_base           16..20
                        mod_base = OTHER
                        note = 2-methoxyethyl
source                  1..20
                        mol_type = other DNA
                        organism = synthetic construct
SEQUENCE: 3
tcctggatcc ttcaccaatg                                               20

SEQ ID NO: 4            moltype = DNA  length = 20
FEATURE                 Location/Qualifiers
misc_feature            1..20
                        note = LY2275796
modified_base           1..5
                        mod_base = OTHER
                        note = 2-methoxyethyl
modified_base           16..20
                        mod_base = OTHER
                        note = 2-methoxyethyl
source                  1..20
                        mol_type = other DNA
                        organism = synthetic construct
SEQUENCE: 4
tgtcatattc ctggatcctt                                               20

SEQ ID NO: 5            moltype = DNA  length = 21
FEATURE                 Location/Qualifiers
misc_feature            1..21
                        note = Sequence encoding non-silencing shRNA
source                  1..21
                        mol_type = other DNA
                        organism = synthetic construct
SEQUENCE: 5
acgtgacacg ttcggagaat t                                             21

SEQ ID NO: 6            moltype = DNA  length = 21
FEATURE                 Location/Qualifiers
misc_feature            1..21
                        note = Sequence encoding eIF4E shRNA
source                  1..21
                        mol_type = other DNA
                        organism = synthetic construct
SEQUENCE: 6
gcgtcaagca atcgagattt g                                             21
```

SELECTIVE INHIBITION OF T FOLLICULAR HELPER CELLS FOR TREATMENT OF AUTOIMMUNE DISORDERS

This application is a continuation of U.S. patent application Ser. No. 17/110,023, filed Dec. 20, 2020, which claims the priority benefit of U.S. Provisional Patent Application Ser. No. 62/942,503, filed Dec. 2, 2019, which is hereby incorporated by reference in its entirety.

This invention was made with government support under grant number RO1 AI137067 awarded by National Institute of Health. The government has certain rights in the invention.

The Sequence Listing is being submitted electronically in XML format and is hereby incorporated by reference in its entirety. Said XML copy, created on Sep. 18, 2024, is named 147462_002224.xml and is 13,006 bytes in size. No new matter is being introduced.

FIELD OF THE INVENTION

The present application relates to the inhibition of and treatment of autoimmune disease resulting from pathologic T Follicular Helper (TFH) cells.

BACKGROUND OF THE INVENTION

T Follicular Helper ("TFH") cells are $CD4^+$ T helper cells that are critical for immune responses to infection and vaccination, but their aberrant accumulation is associated with autoimmune diseases, including Multiple Sclerosis (MS). TFH cells promote differentiation of B cells to high-affinity antibody-producing plasma cells through formation of germinal centers ("GCs"). While TFH cells promote immune responses to pathogens and immunization, pathologic expansion of TFH cells can result in autoimmune disease. TFH cells have a central role in the formation and maintenance of ectopic lymphoid follicles ("ELFs"), which are inducible immunologic centers that generate specific antigen responses but are also associated with autoimmune disorders (Lassmann et al., "Progressive Multiple Sclerosis: Pathology and Pathogenesis," *Nat. Rev. Neurol.* 8(11):647-656 (2012)). TFH cells reside within ELFs and perpetuate the follicles, along with inflammatory TH1 and TH17 cells, and clusters of B cells that promote the survival of TFH cells and have established roles in autoimmune disease (Fletcher et al., "T Cells in Multiple Sclerosis and Experimental Autoimmune Encephalomyelitis," *Clin. Exp. Immunol.* 162 (1):1-11 (2010) and Quinn et al., "Role of TFH Cells in Promoting T Helper 17-Induced Neuroinflammation," *Frontiers in Immunology* 9:382 (2018)). While TFH cells are associated with the pathogenesis of autoimmune diseases and represent a potentially attractive therapeutic target, there are currently no specific pharmacologic inhibitors of TFH cells, and their causal role in autoimmune pathogenesis needs greater clarity.

Since selective expansion of TFH cells that recognize self-antigen can result in autoimmunity, the initiation, commitment, differentiation, and maintenance of TFH cells is regulated by a complex set of coordinated signals. First, T cell receptor ("TCR") and CD28, which provide co-stimulatory signals for T cell activation and survival, are engaged and promote nuclear localization of transcription factors NFAT1 and NFAT2 (Crotty, S., "T Follicular Helper Cell Biology: A Decade of Discovery and Diseases," *Immunity* 50(5):1132-1148 (2019) and Martinez et al., "Cutting Edge: NFAT Transcription Factors Promote the Generation of Follicular Helper T Cells in Response to Acute Viral Infection," *J. Immunol.* 196(5):2015-2019 (2016)), transcriptional coactivator Pou2af1 (Stauss et al., "The Transcriptional Coactivator Bob1 Promotes the Development of Follicular T Helper Cells Via Bcl6," *EMBO J.* 35(8):881-898 (2016)), and expression of immune checkpoint proteins ICOS and PD-1 (Webb et al., "Signals that Drive T Follicular Helper Cell Formation," *Immunology* 152:185-194 (2017)). Next, TFH cell differentiation occurs, initiating with activation of protein kinases mTORC1 and mTORC2 (Yang et al., "Critical Roles of mTOR Complex 1 and 2 for T Follicular Helper Cell Differentiation and Germinal Center Responses," *elife* 5:e17936 (2016)), and upregulation of TFH cell lineage-defining transcription factor, B Cell CLL/Lymphoma 6 ("BCL6") (Johnston et al., "Bcl6 and Blimp-1 are Reciprocal and Antagonistic Regulators of T Follicular Helper Cell Differentiation," *Science* 325(5943):1006-1010 (2009); Nurieva et al., "Bcl6 Mediates the Development of T Follicular Helper Cells," *Science* 325(5943):1001-1005 (2009); and Yu et al., "The Transcriptional Repressor Bcl-6 Directs T Follicular Helper Cell Lineage Commitment," *Immunity* 31(3):457-468 (2009)), which coordinates many functional programs including T cell production of interleukins IL-4 and IL-21, and expression of chemokine receptor CXCR5. CXCR5 plays a critical role in TFH cell function by promoting the migration of T cells to B cell zones and their maintenance within these follicles. TFH cells are further maintained in GCs by stable engagement of GC B cells that involves multiple points of contact, including checkpoints and the lymphocyte signaling molecules PD-1, SLAM, CD28, and OX40 (Webb et al., "Signals that Drive T Follicular Helper Cell Formation," *Immunology* 152:185-194 (2017)).

While transcriptional regulation of TFH cells has been well studied (Liu et al., "Genome-Wide Analysis Identifies Bcl6-Controlled Regulatory Networks during T Follicular Helper Cell Differentiation," *Cell Rep.* 14:1735-1747 (2016)), the regulation of mRNA translation has not. Translational regulation and, in particular, a means for selective mRNA translation of TFH cell mRNAs, might be critical in TFH cell development, given the complex multi-factorial process required for TFH cell differentiation and immune function. In general, mechanisms of translational control remain surprisingly uncharacterized in immune cells, including T helper cells. The canonical translation initiation process involves the $m^7GTP$ (cap) binding protein eukaryotic translation initiation factor 4E (eIF4E), which forms a translation pre-initiation complex (PIC) with core scaffolding initiation factor eIF4G and ATP-dependent RNA helicase eIF4A. The PIC, along with a number of other translation initiation factors, assembles the translation initiation complex at the mRNA 5' cap, recruits the 40S ribosome subunit, and scans the mRNA in search of the downstream initiation codon (typically an AUG) (Silvera et al., "Translational Control in Cancer," *Nat. Rev. Cancer* 10:254-266 (2010)). eIF4E availability is controlled by its sequestration by the eIF4E binding proteins (4E-BPs), which compete with eIF4G for eIF4E binding and are inhibited by mTORC1 phosphorylation (Sonenberg et al., "Regulation of Translation Initiation in Eukaryotes: Mechanisms and Biological Targets," *Cell* 136(4):731-745 (2009)). It is therefore notable that TFH cells are dependent on high levels of mTORC1 (and mTORC2) activity (Yang et al., "Critical Roles of mTOR Complex 1 and 2 for T Follicular Helper Cell Differentiation and Germinal Center Responses," *elife* 5:e17936 (2016)).

SUMMARY OF THE INVENTION

One aspect of the present application relates to a method of inhibiting T Follicular Helper (TFH) cell-mediated differentiation and/or activation in a subject. This method involves administering to a subject in need of treatment for an autoimmune disorder a eukaryotic translation initiation factor 4E (eIF4E) inhibitor to inhibit TFH cell-mediated differentiation and/or activation in the subject.

Another aspect of the present application relates to a method of inhibiting T Follicular Helper (TFH) cell differentiation and/or TFH cell activity. This method involves contacting CD4$^+$ T cells with a eukaryotic translation initiation factor 4E (eIF4E) inhibitor to inhibit TFH cell differentiation and/or TFH cell activity in the contacted cells.

The present application involves inhibitors/antagonists of eIF4E that selectively down regulate TFH cell differentiation and viability without disrupting/inhibiting other T cell types (TH1, TH2, TH17, and regulatory T ("Treg") cells) important to maintaining immune function and limiting toxic side effects. Such inhibitors/antagonists include small molecule drugs such as 4EGI-1 or interfering RNAs targeting eIF4E. Such inhibitors/antagonists can be used in the treatment of subjects diagnosed with autoimmune diseases, including but not limited to, rheumatoid arthritis, asthma, systemic lupus erythematosus (SLE), allergies and food allergies, anaphylactic responses, Jorgen syndrome, multiple sclerosis (MS), autoimmune encephalitis (EAE), lupus nephritis, Type 1 diabetes, juvenile dermatomyositis, autoimmune myasthenia gravis, autoimmune thyroid disease, atherosclerosis, and graft versus host disease, among others.

The present application is based in part on the discovery that (at least partial) inhibition of the translation initiation factor eIF4E can be used to treat a variety of autoimmune disorders that involve TFH cells, to prevent disease, ameliorate and/or reverse disease once started, as well as to prevent disease progression or occurrence. The studies in animal models described herein in the Examples below demonstrate that TFH cells have an acute requirement for high levels of eIF4E which can be selectively downregulated with small molecule drugs such as 4EGI-1 and its similarly active derivatives, 4EIR-Cat and its similarly active derivatives, eFT-4Ei-1, -4ei-2, -4ei-3 and their similarly active derivatives, and ribavirin and its similarly active derivatives, or by interfering RNA or antisense oligonucleotides targeting eIF4E, including but not limited to 4E-ASO, selectively blocking transcription and/or translation of TFH cell lineage/function-determining mRNAs that are essential for TFH cell differentiation and viability, without altering TH1, TH2, TH17, and regulatory T cell (Treg) development. These mRNAs include, but are not limited to, those encoding SLAM, CXCR5, OX40, CD28, BCL6, NFAT1/2, FOXO, PD-1 ICOS, NFAT1, NFAT2, Pou2af1, and others. These TFH cell lineage determining mRNAs have an acute requirement for higher levels of eIF4E and encode transcription factors. Cytokines, chemokines, and other factors required for differentiation of TFH cells from uncommitted CD4$^+$ T cells. The studies demonstrate that T-cell intrinsic inhibition of eIF4E by the drug 4EGI-1 or shRNA resulted in decreased formation of TFH and GC B cells, which require TFH cells for their development and maturation to antibody producing plasma cells, but does not impact differentiation or effector function of TH1, TH2, or TH17 cells.

The studies demonstrate that at least partial inhibition of eIF4E prior to or following induction of autoimmune pathogenesis in animal models of generalized autoimmune pathogenesis (using the OVA/alum model of autoimmune induction, experimental encephalitis (EAE), asthma (*Aspergillus fumigatus*), bacterial (*Staphylococcus aureus*) infection) is sufficient to prevent or reverse pathogenic TFH responses and treat disease.

The present application is illustrated by the Examples infra, which demonstrate the ability to prevent TFH cell development and function, and to reverse TFH cell function and viability following differentiation as a means of preventing or reversing TFH cell-mediated autoimmune disorders using chemical compounds or interfering RNA inhibition of eIF4E. Data demonstrate that downregulating eIF4E activity by these means in generalized autoimmune disorders as shown by immunization with ovalbumin (OVA/alum). Data demonstrate that downregulating eIF4E activity by these means using a multiple sclerosis-like EAE model inhibits TFH cell-mediated autoimmune pathogenesis, T cell infiltration into the central nervous system (CNS), blocks demyelination of the spinal cord (SC) induced during EAE, and can mitigate disease progression and severity of multiple autoimmune disorders. Data demonstrate that downregulating eIF4E activity by these means inhibits TFH cell-mediated autoimmune pathogenesis and manifestations of autoimmune disease in general as mediated by OVA/alum, in asthma development induced by *A. fumigatus*. Data demonstrate that downregulating eIF4E activity by these means inhibits TFH cell-mediated autoimmune pathogenesis and manifestations of autoimmune pathogenesis mediated by *S. aureus* bacterial infection. Thus, selective eIF4E inhibition specifically impairs TFH cells and can treat the pathogenesis of multiple autoimmune disorders. Further, treatment of mice during or after induction of experimental autoimmune encephalitis (EAE) results in improved clinical score and decreased infiltration of pathogenic CD4 T cells to the CNS showing the ability to reverse pathogenic autoimmunity.

The present application is novel and not previously known or used and differs significantly from the disclosure in Yi et al., "The mTORC1-4E-BP-eIF4E Axis Controls de Novo Bcl6 Protein Synthesis in T Cells and Systemic Autoimmunity," *Nat. Commun.* 8:254-254 (2017) ("Yi"). Yi reports that TFH cells require mTORC1/2, which can regulate mRNA translation, among many other activities, and in so doing can impair GC formation in animals. However, Yi never showed reduction of TFH cells in animals or amelioration of disease using an artificial animal model in which many types of immune cells were elevated, and importantly, mTORC1/2 inhibition is not specific to TFH cells. Yi suggests that BCL6 requires eIF4E for translation of its mRNA, but no supporting data is provided. All of the data in Yi regarding the drug 4EGI-1 were carried out in tissue culture and it was never shown to specifically inhibit translation of the group of TFH cell lineage and function determining mRNAs. No in vivo (animal) data was reported and there are no data to suggest that eIF4E downregulation with 4EGI-1 or any other approach could specifically target TFH cells, GCs, and prevent translation of TFH cell-specific mRNAs, reduce progression of, or reverse autoimmune disease of any type in an animal model. There was no evidence to indicate that downregulation of eIF4E using 4EGI-1 or any other eIF4E antagonist, in tissue culture or in animals could specifically downregulate translation of the constellation of mRNAs that promote TFH cell differentiation and function and do so without altering the development or function of other T helper cell subtypes. In contrast to Yi, the Examples of the present application use genome-wide transcription coupled to genome-wide translation analysis to characterize mRNAs in CD4+ T cells that are downregulated in their translation using eIF4E chemical or RNA-based partial inhibition of eIF4E function or levels of expression. These data were used to identify a unique gene set of mRNAs as TFH cell lineage and function determining mRNAs, and demonstrate the very specific and selective inhibition of TFH cell development and function by partial reduction in eIF4E activity or function. The present application demonstrates that prior to TFH cell differentiation, eIF4E is overexpressed in TFH cells, that the higher levels of eIF4E are required for selective translation of a constellation of mRNAs including, but not limited to, those encoding SLAM, CXCR5, OX40, CD28, BCL6, NFAT1/2, FOXO, PD-1 ICOS, NFAT1, NFAT2, Pou2af1, and others that encode TFH cell differentiation and function, and that inhibition of eIF4E with chemical agents or interfering RNAs specifically inhibits TFH cells is well tolerated in animals, and does not alter differentiation of any other helper T cell subset. The present application is also the first to demonstrate that by targeting eIF4E for downregulation in activity or levels, general autoimmune pathology and specific autoimmune pathologies can be prevented, reversed, and multiple autoimmune diseases can be corrected. Moreover, the present application demonstrates that only three days of anti-eIF4E treatment are sufficient to achieve downregulation of TFH cells and GCs, and reduction in autoimmune disease.

The present application is novel and not previously known or used and differs significantly from the disclosure in Bjur et al., "Distinct Translational Control in CD4+ T Cell Subsets," *PLOS Genet.* 9(5):e1003494 (2013) ("Bjur"). Bjur report that Foxp3+ and Foxp3− T cell subsets, which represent activated and proliferative versus non-activated, resting and non-proliferative T cells, can be distinguished by their mRNA translation profile and requirement for eIF4E. Bjur demonstrates that there is a requirement for eIF4E for the translation of Foxp3 mRNA. All of the data in Bjur is directed to distinguishing Foxp3+ from Foxp3− activated from non-activated T cells. Bjur differs from the present application in that they did not investigate TFH cell lineage determination and/or function, they did not study or include TFH cells, and they did not find selective TFH cell mRNA lineage and/or function mRNAs.

BRIEF DESCRIPTION OF THE DRAWINGS

FIGS. 1A-1N show that 4EGI-1 downregulation of eIF4E activity during *S. aureus* infection does not significantly alter in vivo TH1 and TH17 differentiation or in vitro cytokine secretion. FIG. 1A is a graph showing the effect of 4EGI-1 downregulation of eIF4E activity on mouse CD4+ T cell protein synthesis activity by SUnSET assay in uninfected animals. FIGS. 1B-1E are plots showing representative identification of CD4+ T cells by flow cytometry by gating on lymphocytes (FIG. 1B), single cells (FIG. 1C), live cells (FIG. 1D), and CD4+ T cells that are not B220+ (FIG. 1E). FIGS. 1F-1G are graphs showing the measurement of ear thickness (FIG. 1F) and skin neutrophil levels (FIG. 1G) 8 days after *S. aureus* infection, as described in FIG. 2A. FIGS. 1H-1I are representative flow cytometry plots of CD4+ T cells from vehicle or 4EGI-1 treated animals that express intranuclear T-bet (FIG. 1H) or intracellular IFN-g or IL-17A (FIG. 1I) following re-stimulation. Dotted line represents levels present in control mice that were not infected. FIGS. 1M-1N are graphs showing the measurement from supernatant of differentiated TH17 cells of secreted IL-17A (FIG. 1M) or IL-17F (FIG. 1N). In all histograms, dotted line represents levels present in control mice. *P<0.05, P<0.01, *P<0.001.

FIGS. 2A-2Q show that partial pharmacologic downregulation of eIF4E activity inhibits formation of TFH cells but not differentiation or effector function of TH1, TH17, TH2, or Tregs. FIG. 2A is a scheme for mice infected subdermally in the ear pinnae with *S. aureus* and treated daily i.p. with vehicle (veh) or 25 mg/kg 4EGI-1. FIGS. 2B-2E are graphs of skin CD4+ T cells that are T-bet+ (FIG. 2B), IFN-γ+ (FIG. 2C), IRORγt+ (FIG. 2D), and IL-17+ (FIG. 2E). FIG. 2F is a scheme for mice repeatedly intratracheally sensitized with *A. fumigatus* on days 0, 7, and 11, and treated daily with vehicle or 25 mg/kg 4EGI-1. FIGS. 2G-2I are graphs of lung CD4+ T cells that are GATA-3+ (FIG. 2G), IL-13+ (FIG. 2H), and Foxp3+ (FIG. 2I). FIG. 2N is a scheme for OT2 T cell activation and transplant. OT2 cells were activated and stably transduced with lentiviruses expressing Dox-inducible non-silencing (NS) or eIF4E shRNAs. Following puromycin selection, OT2 T cells were transferred into congenic CD45.1 mice and 24 hours later (day 1), placed on a Dox diet for 1 week to induce shRNA silencing. Mice were then injected with OVA/Alum (day 8) and the frequency of OT2 T cells that formed TFH cells determined by flow cytometry 7 days following injection (day 15). FIG. 2O is a graph showing intracellular eIF4E levels in transduced OT2 T cells from the spleen, quantified in permeabilized cells by flow cytometry and eIF4E Ab staining. MFI, mean fluorescence intensity. FIGS. 2P-2Q are graphs showing the numbers of splenic OT2 T cells (FIG. 2P) and OT2 T cells (FIG. 2Q) that formed TFH cells at day 15 post-transfer. *P<0.05, **P<0.01, ±SEM from 3 or more independent studies. The dotted line in all histograms represents levels present in control mice that were not subjected to infection, allergic sensitization, or vaccination.

FIGS. 3A-3K shows downregulation of eIF4E function by 4EGI-1 during *A. fumigatus*-induced airway disease and intracellular levels of eIF4E and eIF4GI in TFH and non-TFH cells. FIGS. 3A-3C are representative flow cytometry plots of CD4+ T cells from lungs of *A. fumigatus* infected mice that express intranuclear GATA3 (FIG. 3A), Foxp3 (FIG. 3B), or intracellular IL-13 (FIG. 3C) following infection as described in the legend to FIG. 2F. FIG. 3D is a graph showing quantification of lung eosinophil levels at day 18 following *A. fumigatus* sensitization, as described in the legend to FIG. 2F. The dotted line represents levels present in control mice not subjected allergic sensitization. FIG. 3E is a graph showing Naïve T cells activated under TH2 conditions and treated with 4EGI-1 following activation as in FIGS. 1A-N, and IL-13 measured from the supernatant of TH2 cells. FIGS. 3F-3G are representative images of lung sections from *A. fumigatus* sensitized mice treated with vehicle or 4EGI-1, or animals not treated with allergen that were stained with Periodic acid Schiff stain (PAS) for mucin (magenta) (FIG. 3F) or H&E (FIG. 3G). Scale bar, 500 microns. FIG. 3H is a representative flow cytometry plot for identification of CD4$^+$ T cells that are TFH or non-TFH. FIGS. 3I-3J are a pair of graph and histogram of TFH and non-TFH CD4$^+$ T cell intracellular levels of eIF4E (FIG. 3I) and eIF4G1 (FIG. 3J). The dotted line represents levels in isotype control. FIG. 3K is a graph showing the intracellular levels of eIF4E in adoptively transferred NS or eIF4E shRNA OT2 cells isolated from the blood from mice with prior to OVA/Alum immunization and placed on Dox for 1 week. In all histograms, dotted line represents levels present in control mice. *P<0.05, P<0.01, *P<0.001.

FIGS. 4A-4H show mRNA and pathway analysis of downregulation of eIF4E activity in CD4$^+$ T cells. FIG. 4A is a scheme for OVA/alum immunization and treatment with vehicle or 25 mg/kg 4EGI-1, isolation of CD4$^+$ T cells, genome-wide translatomic analysis by polysome profiling, genome-wide transcriptomic analysis by mRNA sequencing. FIG. 4B is a scatter plot highlighting genes/mRNAs regulated by 4EGI-1 at the level of transcription (blue), translation (green) or both (pink). FIG. 4C is a graph showing numbers of genes/mRNAs affected by 4EGI-1 downregulation of eIF4E activity. Color code same as in FIG. 4B. FIGS. 4D-4F are graphs showing top pathways, mRNAs, and their translation that are down-regulated by 4EGI-1 treatment. Top pathways downregulated with eIF4E partial inhibition by 4EGI-1 (FIG. 4D). Top transcription factors reduced in mRNA level and/or translation with 4EGI-1 treatment (FIG. 4E). Top pathways translationally downregulated with 4EGI-1 treatment (FIG. 4F). FIG. 4G is a plot showing the annotation of select genes/mRNAs that are highlighted in pathway analysis and required for TFH cell differentiation and maintenance that rely on higher eIF4E levels for transcription and/or translation. Data from two independent studies. Color code same as in FIG. 4B. FIG. 4H shows the number of genes/mRNAs enriched in TFH cells that are regulated by transcription, translation, or both.

FIGS. 5A-5O demonstrate that higher levels of eIF4E stimulate BCL6 expression, its transcriptional programs, and expression of co-stimulatory proteins required for TFH cell development and GC B cell maintenance. FIG. 5A is a scheme for OVA/alum immunization and treatment with vehicle or 4EGI-1 as shown in FIG. 2A. FIGS. 5B-5C are graphs showing flow cytometry quantification of CD4$^+$ T cells (FIG. 5B) and % divided cells (FIG. 5B) following OVA/alum immunization and treatment with vehicle or 4EGI-1 as in FIG. 5A. FIGS. 5D-5G are graphs showing flow cytometry quantification of CD4$^+$ T cell expression of ICOS (FIG. 5D), PD-1 (FIG. 5E), intranuclear BCL6 (FIG. 5F), and CXCR5 (FIG. 5G). FIG. 5H shows representative immunofluorescence images of splenic sections stained for CD4$^+$ T cells (green) and B220$^+$ B cells (red). B cell follicles outlined and overlaid on CD4$^+$ T cell stain (dotted line). Scale bar=200 microns. FIG. 5I shows quantification of 12 images from 3 independent studies of CD4$^+$ T cells in B cell follicles normalized to a standard area. FIGS. 5J-5N show quantification of splenic CD4$^+$ T cells that express IL-4 (GFP$^+$) (FIG. 5J), IL-21 (VFP$^+$) (FIG. 5K), SLAM (FIG. 5L), CD28 (FIG. 5M), or OX40 (FIG. 5N). FIG. 5O is a graph of mice immunized with OVA/Alum as in FIG. 5A, but treated with 4EGI-1 for 14 days and TFR cells quantified. Dotted line in all histograms represents levels present in control mice. *P<0.05, P<0.01, *P<0.001, ±SEM from 3 or more independent studies.

FIG. 6A is a chart showing numbers and percent of mRNAs altered in abundance at the level of transcription, translation, or both by 4EGI-1 downregulation of eIF4E activity. FIGS. 6B-6C show pathway analysis (FIG. 6B) and transcription factor binding (FIG. 6C) prediction of top 100 mRNAs downregulated by 4EGI-1 transcriptionally and/or translationally.

FIGS. 7A-7D show representative identification of B cell subsets by flow cytometry by gating on lymphocytes (FIG. 7A), single cells (FIG. 7B), live B cells (FIG. 7C), plasmablasts (PB) identified as B220$^+$ CD138$^+$ (FIG. 7D), plasma cells (PCs) as B220mid/neg CD138$^{high}$. In FIGS. 7E-7H, GC B cells were identified as B220$^+$ GL7$^+$ Fas$^+$ (FIG. 7E) and further characterized as CD86$^+$ (LZ, light zone) and CXCR4$^+$ (DZ, dark zone) (FIG. 7F), IgG1 class switched (FIG. 7G), OVA-specific from OVA-alum immunized mice (FIG. 7H). FIGS. 7I-7J are graphs showing the quantification of B cells (FIG. 7I) and OVA-specific GC B cells (FIG. 7J) seven days following OVA/alum immunizations, as described in the legend to FIG. 2J. In all histograms, dotted line represents levels present in control mice. *P<0.05, P<0.01, *P<0.001.

FIG. 8A shows representative flow cytometry identification of GC B cells (B220$^+$ Fas$^+$ GL7$^+$) from mice immunized with OVA/Alum administered vehicle, 4EGI-1, or Alum only control mice, analyzed at day 7 as in FIG. 2A. FIGS. 8B-8G are graphs showing quantification of OVA/Alum treated mice with vehicle or 4EGI-1 for splenic GC B cells (FIG. 8B), splenic GC B cells that are CD86$^+$ (LZ, light zone) (FIG. 8C), CXCR4$^+$ (DZ, dark zone) (FIG. 8D), IgG1 class switched (FIG. 8E), plasmablasts (FIG. 8F), and plasma cells (FIG. 8G). FIG. 8H is a graph showing quantification of OVA-specific IgG1 antibody secreting cells (ASCs) treated as in FIG. 8A per 10$^6$ splenocytes. FIG. 8I is a graph showing serum levels of OVA-specific IgG1 antibody. Dotted lines in all histograms represent levels present in control mice. *P<0.05, P<0.01, *P<0.001±SEM from 3 or more independent studies.

FIGS. 9A-9D show quantification and representative flow cytometry plots at day 8 from cervical lymph nodes (CLNs) of animals infected with *S. aureus* as described in the legend to FIG. 2A. FIGS. 9A-9B show a graph (FIG. 9A) and plots (FIG. 9B) for TFH cells. FIGS. 9C-9D show a graph (FIG. 9C) and plots (FIG. 9D) for GC B cells. FIG. 9E is a graph showing serum levels of *S. aureus*-specific IgG1 at day 8 from animals infected with *S. aureus* that were treated with vehicle or 4EGI-1. FIGS. 9F-9I show quantification and representative flow cytometry plots at day 18 from mediastinal lymph nodes (MedLN) of animals repeatedly sensitized with *A. fumigatus*, as described in the legend to FIG. 2F. FIGS. 9F-9G show a graph (FIG. 9F) and plots (FIG. 9G) for TFH cells. FIGS. 9H-9I show a graph and plots (FIG. 9I) for GC B cells. FIG. 9J is a graph showing serum levels of total IgE from animals at day 18 that were sensitized with *A. fumigatus* and treated with vehicle or 4EGI-1. The dotted line represents levels present in control animals that were not subjected to infection or allergic sensitization. In all histograms, dotted line represents levels present in control mice. *P<0.05, P<0.01, *P<0.001.

FIGS. 10A-10O show that maintenance of BCL6 expression in mouse CD4+ T cells and TFH cells in human lymph node requires continuous translation by a higher level of eIF4E. In FIGS. 10A-10F, CD4+ T cells from mice immunized with OVA/Alum were incubated with increasing (0-25 µM) concentrations of 4EGI-1 for 4 hours. FIG. 10A is a graph showing quantification of protein synthesis activity by SUnSET assay. FIG. 10B is a graph showing CD4+ T cell viability. FIGS. 10C-10F are graphs showing levels of extracellular CXCR5 (FIG. 10C), intranuclear BCL6 (FIG. 10D), extracellular PD-1 (FIG. 10E), ICOS (FIG. 10F). FIGS. 10G-10H show dot plots and histograms of the human TFH isolated cell population. TFH cells were identified as PD1+ and CXCR5+ double positive (FIG. 10G), and quantified for BCL6+ (red; CD4+ CD45RO+ CXCR5+ PD1+ BCL6+ ICOS+) (FIG. 10H). In FIGS. 10L-10O, human CD4+ CD45RO+ lymph node cells were incubated with 0-30 µM 4EGI-1 overnight and quantified by flow cytometry for expression of intranuclear BCL6 (FIG. 10L) and surface expression of PD1 (FIG. 10M), ICOS (FIG. 10N), and CXCR5 (FIG. 10O). Values normalized to percent of control (no 4EGI-1). Patient lymph node location noted. *P<0.05, ***P<0.001, ±SEM from 3 or more independent analyses.

FIG. 11A is a scheme for induction of active EAE by MOG/CFA with daily treatment of vehicle (veh) or 25 mg/kg 4EGI-1. FIG. 11N is a graph showing quantification of cell infiltration into spinal cord. Dotted line represents levels in control animals with no EAE. *P<0.05, P<0.01, *P<0.001±SEM from 3 or more independent studies.

FIG. 12A shows representative images of Luxol fast blue (LFB) stained spinal cords (SC) from animals with EAE induced as in FIGS. 11A-N, treated with vehicle (veh) or 4EGI-1. Myelin stained blue. Scale bar, 500 microns. FIG. 12B is a graph showing quantified SC white matter myelination levels in control (no EAE) and EAE animals treated with veh or 4EGI-1. FIGS. 12C-12E are images showing staining of SCs from control and EAE mice CD4+ T cells (red) and CD19+ B cells (green) and enlargement of ectopic lymphoid follicles treated with vehicle (FIG. 12C), 4EGI-1 (FIG. 12D), and control animals with no EAE (FIG. 12E). In histogram, dotted line represents levels in controls animals with no EAE. **P<0.01 SEM from 3 or more independent studies.

FIGS. 13A-13I demonstrate that pretreatment of lymphocytes with 4EGI-1 prior to adoptive transfer of preformed TFH cells inhibits pathological development of disease and TFH cells. FIG. 13A is a scheme for OT2 T cell activation and treatment in culture with vehicle (veh) or 20 µM 4EGI-1 for 1 hour. Cells were transferred into CD45.1 congenic host mice that had been immunized with OVA/Alum 3 days prior to transfer. FIG. 13B is a graph showing OT2 T cells in spleen at 3 days after adoptive transfer (day 7) in control and 4EGI-1 treated mice. FIG. 13C is a scheme for OT2 T cell analysis post-4EGI-1 treatment at 34 days after adoptive transfer into CD45.1 congenic mice. FIG. 13D is a graph showing OT2 T cells in spleen at 34 days after adoptive transfer in control and 4EGI-1 treated mice. FIG. 13E is a graph showing OT2 TFH cells in spleen at 34 days post-transfer. FIG. 13F is a graph showing OT2 TFH cells at 34 days post transfer in the spleen quantified for intracellular levels of eIF4E in permeabilized cells by flow cytometry. FIG. 13G is a scheme for treatment of TH17-differentiated 2D2 cells with vehicle or 20 µM 4EGI-1 in culture and transfer into congenic mice for induction of passive EAE. FIG. 13H is a graph showing the daily clinical score of EAE mice with adoptively transferred differentiated 2D2 cells pre-treated with vehicle or 4EGI-1. FIG. 13I is a graph showing quantification of TFH-like (ICOS$^{high}$) 2D2 T cells in the SCs of EAE mice at day 34. *P<0.05, ***P<0.001±SEM from 3 or more independent studies.

FIGS. 14A-14R demonstrate that downregulation of eIF4E activity inhibits progression of active EAE and TH17-dependent ELF formation in passive EAE. FIG. 14A is a scheme showing a protocol where mice were immunized with OVA/Alum, then following formation of TFH cells on day 7, treated with 50 mg/kg or 75 mg/kg 4EGI-1 for 6 days. FIG. 14B is a graph showing quantification of CD4+ T cell protein synthesis rates when treated at 75 mg/kg 4EGI-1 determined by SunSET assay. FIGS. 14C-14D are graphs showing quantification of splenic CD4+ T cells (FIG. 14C), TFH cells (FIG. 14D), GC B cells (FIG. 14E), OVA-specific IgG1+ antibody secreting cells (ASCs) (FIG. 14F), and serum levels of OVA-specific IgG1 (FIG. 14G). FIGS. 14P-14R are graphs showing quantification of brain CD4+ T cells in animals 18 days following onset of disease for CD4+ of CD45+ cells (FIG. 14P), CD4+ T cells expressing IFN-γ+ (FIG. 14Q), or IL17A+ (FIG. 14R). Dotted line represents levels present in control mice. *P<0.05, P<0.01, *P<0.001±SEM from 3 or more independent studies.

FIGS. 15A-15G show that downregulation of eIF4E activity promotes myelination after onset of active EAE and ELF formation in spinal cord. FIG. 15A shows representative images from control animals (no EAE) and at day 21 from animals with active EAE induction treated with vehicle (veh) or 4EGI-1 as in FIG. 14H. Luxol fast blue (LFB) stained spinal cords (SC), myelin stained blue. FIG. 15B is a graph showing quantified spinal cord white matter myelination. FIG. 15C shows representative H&E stained cross-sections of SCs from animals as in FIG. 15A. Clusters of blue nuclei identify cell infiltration. FIG. 15D is a graph showing quantification of infiltration of cells into spinal cord. FIGS. 15E-15G show staining of spinal cords for $CD4^+$ T cells (red), $CD19^+$ B cells (green) and enlargement of ectopic lymphoid follicles or $CD4^+$ T cells clusters from mice with EAE that were treated with vehicle (FIG. 15E), 4EGI-1 (FIG. 15F), and control animals (FIG. 15G) not subject to EAE. Scale bar, 500 microns. Dotted lines represent levels present in mice not subjected to EAE. **$P<0.01\pm SEM$ from 3 or more independent studies.

DETAILED DESCRIPTION OF THE INVENTION

Figure 1J:
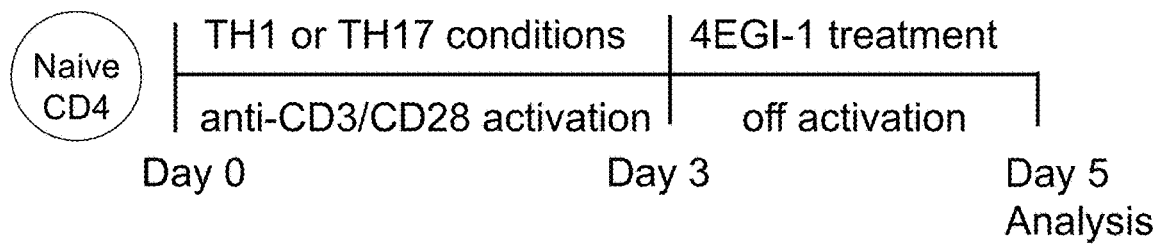
FIG. 1J is a scheme for activation of naïve CD4+ T cells and differentiation to TH1 or TH17 cells with 4EGI-1 treatment following activation.
Figure 1K:
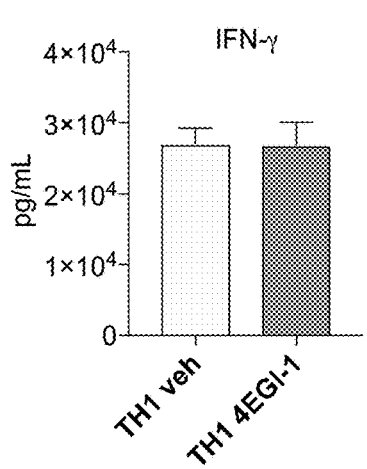
FIGS. 1K-1L are graphs showing the measurement from supernatant of differentiated TH1 cells of secreted IFN-g (FIG. 1K) or TNF-α (FIG. 1L).
Figure 1L:
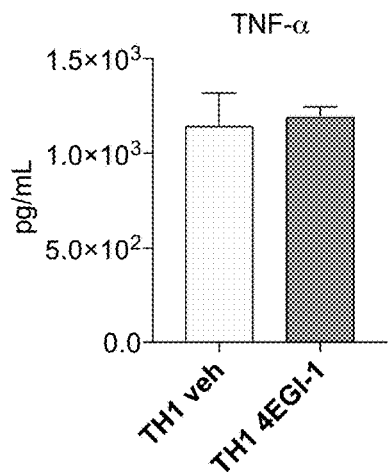
Figure 1M:
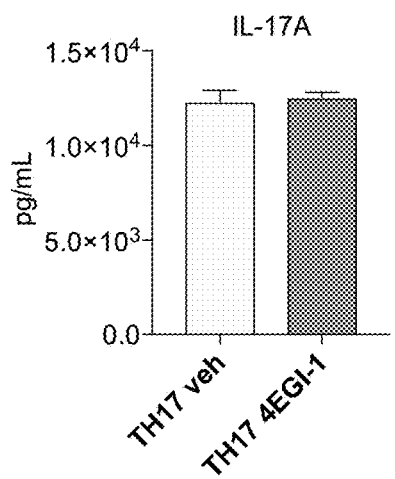
Figure 1N:
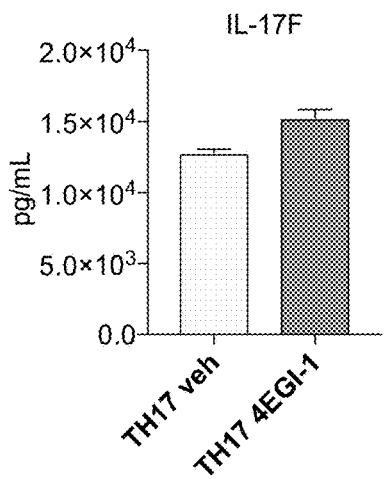

One aspect of the present application relates to a method of inhibiting T Follicular Helper (TFH) cell-mediated differentiation and/or activation in a subject. This method involves administering to a subject in need of treatment for an autoimmune disorder a eukaryotic translation initiation factor 4E (eIF4E) inhibitor to inhibit TFH cell-mediated differentiation and/or activation in the subject.

Another aspect of the present application relates to a method of inhibiting T Follicular Helper (TFH) cell differentiation and/or TFH cell activity. This method involves contacting a T cell with a eukaryotic translation initiation factor 4E (eIF4E) inhibitor to inhibit TFH cell differentiation and/or TFH cell activity in the contacted cell. According to this aspect, the method may be carried out in vitro or in vivo. In some embodiments, said contacting is effective to inhibit the ability of the contacted T cell to mediate B cell differentiation.

The present application involves the use of inhibitors/antagonists of eIF4E to selectively down regulate TFH cell differentiation and viability, without disrupting/inhibiting other T cell types (TH1, TH2, TH17, and regulatory T cell (Treg)) important to maintaining immune function and limiting toxic side effects. Such inhibitors/antagonists include small molecule drugs such as 4EGI-1 or interfering RNAs. Such inhibitors/antagonists can be used in the treatment of subjects with autoimmune diseases, including but not limited to, those involving pathogenic antibody producing B cells; allergies and food allergies; anaphylactic responses; inflammatory disorders; chronic skin diseases; endocrinopathies; neurological, muscle, and vascular autoimmune diseases; gastrointestinal tract and hepatological autoimmune diseases; and autoimmune thyroid diseases.

Suitable autoimmune diseases involving pathogenic antibody producing B cells include, but are not limited to, graft versus host disease (GVHD) and systemic sclerosis.

Suitable inflammatory disorders include, but are not limited to, systemic lupus erythematosus (SLE), rheumatoid arthritis (RA), autoimmune hemolytic anemia, vitiligo, pernicious anemia, antiphospholipid syndrome, ant-IgA antibody disease, juvenile idiopathic arthritis, ankylosing spondylitis (AS), idiopathic thrombocytopenic purpura, and vasculitis.

Suitable chronic inflammatory skin diseases include, but are not limited to, psoriasis, atopic dermatitis, juvenile dermatomyositis, pemphigus, and bullous pemphigoid.

Suitable endocrinopathies include, but are not limited to, pancreatitis, glomerulonephritis, diabetic nephropathy, lupus nephritis, type 1 diabetes, and Sjogren syndrome.

Suitable neurological, muscle, and vascular autoimmune diseases include, but are not limited to, multiple sclerosis (MS), autoimmune myasthenia gravis, autoimmune carditis, atherosclerosis, asthma, neuromyelitis optica spectrum disorders, uveitis, idiopathic inflammatory myopathies, dermatomyositis, and polymyositis.

Suitable gastrointestinal tract and hepatological autoimmune diseases include, but are not limited to, Crohn's disease, ulcerative colitis, inflammatory bowel diseases, primary biliary cholangitis, and autoimmune hepatitis.

Suitable autoimmune thyroid diseases include, but are not limited to, Hashimoto's thyroiditis and Grave disease.

The present application is based in part on the discovery that partial inhibition of the translation initiation factor eIF4E can be used to treat a variety of autoimmune disorders that involve TFH cells, to prevent disease, ameliorate and/or reverse disease once started, as well as to prevent or inhibit disease progression or occurrence. The studies in animal models described in the Examples herein demonstrate that TFH cells have an acute requirement for high levels of eIF4E which can be selectively downregulated with chemical compound drugs such as 4EGI-1 and derivatives, 4EIR-Cat and derivatives, and ribavirin, or by interfering RNA or antisense oligonucleotides including but not limited to 4E-ASO, specifically blocking translation of TFH cell lineage and function mRNAs that are essential for TFH cell differentiation and viability, but dispensable for development of other T helper cells, including TH1, TH2, TH17, and regulatory T cell (Treg) development. The studies demonstrate that T-cell intrinsic inhibition of eIF4E by the drug 4EGI-1 or shRNA resulted in decreased formation of TFH and GC B cells but did not impact differentiation or effector function of TH1, TH2, TH17, or Treg cells. The studies demonstrate that in animal models of generalized autoimmune pathogenesis (using the OVA model of autoimmune induction, experimental encephalitis (EAE), asthma (*Aspergillus fumigatus*), or bacterial (*Staphylococcus aureus*) infection), partial inhibition of eIF4E prior to or following induction of autoimmune pathogenesis is sufficient to prevent or reverse pathogenic TFH responses and treat disease. Thus, in some embodiments of the method of inhibiting TFH cell-mediated differentiation and/or activation described herein, said administering is carried out to inhibit TFH cell-mediated B cell differentiation and/or activation in the subject. Suitable B cells include, without limitation, germinal center (GC) B cells, $CD86^+$ B cells, $CXCR4^+$ B cells, plasmablasts, and plasma cells. In other embodiments, said administering is carried out to inhibit TFH cell-mediated TH17 cell activation. Suitable TFH cells include, without limitation, $CD4^+$ $PD1^+$ cells, $CD4^+$ $CXCR5^+$ cells, $CD4^+$ $IL-21^+$ cells, $CD4^+$ TFR cells, $CD4^+$ $IL-4^+$ cells, $CD4^+$ interferon $\gamma^+$ cells.

In some embodiments of the methods of the present application, the eIF4E inhibitor does not directly inhibit BCL6.

As used herein, a "subject" is, e.g., a patient, such as a patient in need of treatment for an autoimmune disorder, and encompasses any animal, but preferably a mammal. In one embodiment, the subject is a human subject. Suitable human subjects include, without limitation, an infant, a child, an adolescent, an adult, and/or a geriatric adult.

Suitable T cells include cells from any animal, but preferably a mammal. In some embodiments, the T cell is a human cell. The T cell may be a $CD4^+$ T cell, e.g., a naïve T cell, an antigen-experienced T cell, and/or primed T cell. In a further embodiment, the CD4+ T cell is a pre TFH cell, an immature TFH cell, or a mature TFH cell.

In one embodiment of carrying out the methods of the present application, the autoimmune disorder is selected from the group consisting of an autoimmune disorder involving pathogenic antibody producing B cells; allergies and food allergies; anaphylactic responses; inflammatory disorders; chronic skin diseases; endocrinopathies; neurological, muscle, and vascular autoimmune diseases; gastrointestinal tract and hepatological autoimmune diseases; and autoimmune thyroid diseases.

In one embodiment, an eIF4E inhibitor is selected from, but not limited to, reversibly binding nucleotide analogues resembling m⁷GTP and their derivatives; covalently binding inhibitors to the eIF4E m⁷GTP (cap) binding site; inhibitors of eIF4E binding of eIF4E to eIF4G; antisense RNAs and antisense oligonucleotides (ASOs) to eIF4E of which LY2275796 is a prototype; Ribavarin and other compounds that share similar structure to 7-methyl-GTP; 7-methyl-GMP analogues and their derivatives; and inhibitors that use 4E binding protein mimetic peptides to bind and block eIF4E.

In some embodiments, the eIF4E inhibitor is selected from, but not limited to, reversibly binding nucleotide analogues resembling m⁷GTP and their derivatives (see, e.g., Ghosh et al., "Nontoxic Chemical Interdiction of the Epithelial-to-Mesenchymal Transition by Targeting Cap-Dependent Translation," *ACS Chem. Biol.* 4(5):367-377 (2009); Chen et al., "Small-Molecule Inhibition of Oncogenic Eukaryotic Protein Translation in Mesothelioma Cells," *Invest. New Drugs* 32(4):598-603 (2014); Li et al., "Treatment of Breast and Lung Cancer Cells with a N-7 Benzyl Guanosine Monophosphate Tryptamine Phosphoramidate Pronucleotide (4Ei-1) Results in Chemosensitization to Gemcitabine and Induced eIF4E Proteasomal Degradation," *Mol. Pharm.* 10(2):523-531 (2013); and Ghosh et al., "Synthesis and Evaluation of Potential Inhibitors of eIF4E Cap Binding to 7-methyl GTP", *Bioorg. Med. Chem. Lett.* 15(8):2177-2180 (2005), which are hereby incorporated by reference in their entirety).

In some embodiments, the eIF4E inhibitor is selected from, but not limited to, covalently binding inhibitors to the eIF4E m⁷GTP (cap) binding site such as arylsulfonyl fluoride compounds 2-12 described in Wan et al., "Discovery of Lysine-Targeted eIF4E Inhibitors Through Covalent Docking," *J. Am. Chem. Soc.* 142(11):4960-4964 (2020), which is hereby incorporated by reference in its entirety. Thus, in some embodiments, the eIF4E inhibitor may be (compound 11)

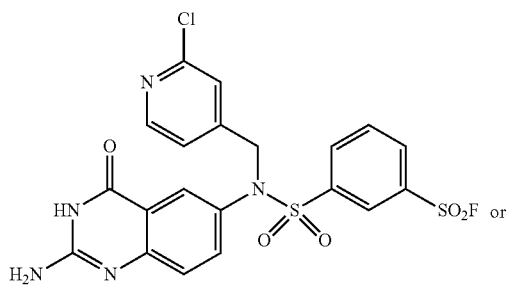

or (compound 12)

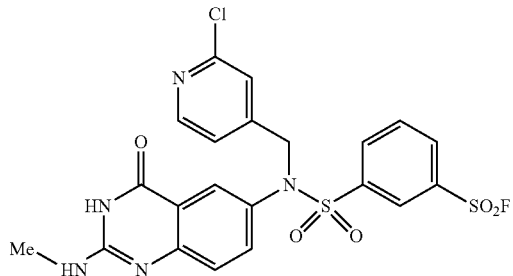

of Wan et al., "Discovery of Lysine-Targeted eIF4E Inhibitors Through Covalent Docking," *J. Am. Chem. Soc.* 142(11):4960-4964 (2020), which is hereby incorporated by reference in its entirety.

In some embodiments, the eIF4e inhibitor is selected from, but not limited to, inhibitors of eIF4E binding of eIF4E to eIF4G of which 4EGI-1 is a prototype (Moerke et al., "Small-Molecule Inhibition of the Interaction Between the Translation Initiation Factors eIF4E and eIF4G," *Cell* 128(2):257-267 (2007); Descamps et al., "The Cap-Translation Inhibitor 4EGI-1 Induces Apoptosis in Multiple Myeloma Through Noxa Induction," *Br. J. Cancer* 106(10): 1660-1667 (2012); Tamburini et al., "Protein Synthesis is Resistant to Rapamycin and Constitutes a Promising Therapeutic Target in Acute Myeloid Leukemia," *Blood* 114(8): 1618-1627 (2009); and Mahalingam et al., "Synthesis of Rigidified eIF4E/eIF4G Inhibitor-1 (4EGI-1) Mimetic and their In Vitro Characterization as Inhibitors of Protein-Protein Interaction," *J. Med. Chem.* 57(12): 5094-5111 (2014), which are hereby incorporated by reference in their entirety); 4E1RCat (Cencic et al., "Reversing Chemoresistance by Small Molecule Inhibition of the Translation Initiation Complex eIF4F," *Proc. Natl. Acad. Sci. USA* 108(3): 1046-1051 (2011), which is hereby incorporated by reference in its entirety); Ouabain, Perillyl Alcohol and other cardiac glycosides (Cao et al., "Cap-Dependent Translation Initiation Factor eIF4E is the Target for Ouabain-Mediated Inhibition of HIF-1α," *Biochem. Pharmacol.* 89(1):20-30 (2014), which is hereby incorporated by reference in its entirety).

In some embodiments, the eIF4E inhibitor is selected from, but not limited to, antisense RNAs and antisense oligonucleotides (ASOs) to eIF4E of which LY2275796 is a prototype (Graff et al., "Therapeutic Suppression of Translation Initiation Factor eIF4E Expression Reduces Tumor Growth without Toxicity," *J. Clin. Invest.* 118(7):2651-2660 (2008) and Hong et al., "A Phase 1 Dose Escalation, Pharmacokinetic, and Pharmacodynamic Evaluation of eIF-4E Antisense Oligonucleotide LY2275796 in Patients with Advanced Cancer," *Clin. Cancer Res.* 17(20):6582-6591 (2011), which are hereby incorporated by reference in their entirety).

In some embodiments, the eIF4E inhibitor is selected from, but not limited to, Ribavarin and other compounds that share similar structure to 7-methyl-GTP (Hofmann et al., "Ribavirin Mode of Action in Chronic Hepatitis C: From Clinical Use back to Molecular Mechanisms," *Liver Int.* 28(10):1332-1343 (2008); Kentsis et al., "Ribavirin Suppresses eIF4E-Mediated Oncogenic Transformation by Physical Mimicry of the 7-Methyl Guanosine mRNA Cap," *Proc. Natl. Acad. Sci. USA* 101(52):18105-18110 (2004); Tan et al., "Ribavirin Targets eIF4E Dependent Akt Survival Signaling," *Biochem. Biophys. Res. Commun.* 375(3):341-345 (2008); Assouline et al., "Molecular Targeting of the Oncogene eIF4E in Acute Myeloid Leukemia (AML), A Proof-of-Principle Clinical Trial with Ribavirin," *Blood* 114(2):257-260 (2009); and Pettersson et al., "Ribavirin Treatment Effects on Breast Cancers Overexpressing eIF4E, a Biomarker with Prognostic Specificity for Luminal B-Type Breast Cancer," *Clin. Cancer Res.* 17(9):2874-2884 (2011), which are hereby incorporated by reference in their entirety).

In some embodiments, the eIF4E inhibitor is selected from, but not limited to, 7-methyl-GMP analogues and their derivatives which include, but are not limited to, 7BnGMP and 4Ei-1 (Ghosh et al., "Nontoxic Chemical Interdiction of the Epithelial-to-Mesenchymal Transition by Targeting Cap-Dependent Translation," *ACS Chem. Biol.* 4(5):367-377 (2009); Chen et al., "Small-Molecule Inhibition of Oncogenic Eukaryotic Protein Translation in Mesothelioma Cells," *Invest. New Drugs* 32(4):598-603 (2014); and Li et al., "Treatment of Breast and Lung Cancer Cells with a N-7 Benzyl Guanosine Monophosphate Tryptamine Phosphoramidate Pronucleotide (4Ei-1) Results in Chemosensitization to Gemcitabine and Induced eIF4E Proteasomal Degradation," *Mol. Pharm.* 10(2):523-531 (2013), which are hereby incorporated by reference in their entirety), Bn$^7$GMP (Cai et al., "Quantitative Assessment of mRNA Cap Analogues as Inhibitors of In Vitro Translation," *Biochemistry* 38(26):8538-8547 (1999); Jia et al., "Design, Synthesis and Evaluation of Analogs of Initiation Factor 4E (eIF4E) Cap-Binding Antagonist Bn7-GMP," *Eur. J. Med. Chem.* 45(4): 1304-1313 (2010); and Brown et al., "Crystallographic and Mass Spectrometric Characterization of eIF4E with N7-Alkylated Cap Derivatives," *J. Mol. Biol.* 372(1):7-15 (2007); and Chen et al., "Structure-Guided Design, Synthesis, and Evaluation of Guanine-Derived Inhibitors of the eIF4E mRNA-Cap Interaction," *J. Med. Chem.* 55(8):3837-3851 (2012), which are hereby incorporated by reference in their entirety); 4Ei10 (Okon et al., "Anchimerically Activated ProTides as Inhibitors of Cap-Dependent Translation and Inducers of Chemosensitization in Mantle Cell Lymphoma," *J. Med. Chem.* 60(19):8131-8144 (2017), which is hereby incorporated by reference in its entirety); eFT-4Ei-1, eFT-4Ei-2, or eFT-4Ei-3 (see, e.g., Chiang et al., "Poster and Abstract 1302: Targeting Hormone Receptor-Dependent Cancers with Potent, Selective and Orally-Available Small Molecule Inhibitors of eIF4E," *Proceedings of the American Association for Cancer Research Annual Meeting* 2019; 2019 Mar. 29-Apr. 3; Atlanta, GA Philadelphia (Pa.): AACR Cancer Res 2019; 79(13 Suppl): Abstract nr 1302. (2019), which is hereby incorporated by reference in its entirety), and derivatives thereof.

In some embodiments, the eIF4E inhibitor is selected from, but not limited to, inhibitors that use 4E binding protein mimetic peptides to bind and block eIF4E, including the prototype GnRH-4EBP (Ko et al., "Inhibition of Ovarian Cancer Growth by a Tumor-Targeting Peptide that Binds Eukaryotic Translation Initiation Factor 4E," *Clin. Cancer Res.* 15(13):4336-4347 (2009), which is hereby incorporated by reference in its entirety).

Thus, in some embodiments, the eIF4E inhibitor is selected from the group consisting of 4EGI-1, 4Ei-1, eFT-4Ei-1, eFT-4Ei-2, or eFT-4Ei-3, 4EIR-Cat, ribavirin, 4EBP mimetic peptides, Bn$^7$GMP, and derivatives thereof.

In another embodiment, the eIF4E inhibitor is a nucleic acid molecule. According to this embodiment, the nucleic acid molecule may encode an antisense oligonucleotide (ASO), small interfering RNA (siRNA), small hairpin (shRNA), or microRNA (miRNA) molecule.

The use of antisense oligonucleotides to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense oligonucleotides are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense oligonucleotide hybridizes to its corresponding target nucleic acid molecule, such as any of the eIF4E mRNA to form a double-stranded molecule, which interferes with translation of the mRNA, as the cell will not translate a double-stranded mRNA. Antisense oligonucleotides used in the methods of the present application are typically at least 10-15 nucleotides in length, for example, at least 10, 11, 12, 13, 14, 15, 16, 17, 18, 19, 20, 25, 30, 35, 40, 45, 50, 55, 60, 65, 70, 75, or greater than 75 nucleotides in length. The antisense oligonucleotide can also be as long as its target nucleic acid with which it is intended to form an inhibitory duplex. In one embodiment, the antisense oligonucleotide is eIF4E ASO LY2275796 (Graff et al., "Therapeutic Suppression of Translation Initiation Factor eIF4E Expression Reduces Tumor Growth without Toxicity," *Journal of Clinical Investigation* 117:2638-2648 (2007) and Hong et al., "A phase 1 Dose Escalation, Pharmacokinetic, and Pharmacodynamic Evaluation of eIF-4E Antisense Oligonucleotide LY2275796 in Patients with Advanced Cancer," *Clinical Cancer Research* 17:6582-6591 (2011), which are hereby incorporated by reference in their entirety).

In some embodiments, the antisense oligonucleotide is 2-methoxyethyl-modified. The antisense oligonucleotide may be 2-methoxyethyl-modified at the 5'-end, the 3'-end, or at both the 5'-end and 3'-end. Suitable 2-methoxyethyl-modified eIF4E antisense oligonucleotides include, but are not limited to, those identified in Table 1.

TABLE 1 eIF4E Antisense Oligonucleotides

| Name | Sequence* | SEQ ID NO: |
|---|---|---|
| eIF4E-ASO1 | 5'-TGCTATCTTATCACCTTTAG-3' | SEQ ID NO: 1 |
| eIF4E-ASO2 | 5'-GGCGAATGAGACTTCTCTTA-3' | SEQ ID NO: 2 |
| eIF4E-ASO3 | 5'-TCCTGGATCCTTCACCAATG-3' | SEQ ID NO: 3 |
| LY2275796 | 5'-TGTCATATTCCTGGATCCTT-3' | SEQ ID NO: 4 |

*Sequences shown in bold underline are 2-methoxyethyl-modified (Graff et al., "Therapeutic Suppression of Translation Initiation Factor eIF4E Expression Reduces Tumor Growth without Toxicity," *Journal of Clinical Investigation* 117:2638-2648 (2007); Hong et al., "A phase 1 Dose Escalation, Pharmacokinetic, and Pharmacodynamic Evaluation of eIF-4E Antisense Oligonucleotide LY2275796 in Patients with Advanced Cancer," *Clinical Cancer Research* 17:6582-6591 (2011); and Jacobson et al., "Targeting Eukaryotic Translation in Mesothelioma Cells with an eIF4E-Specific Antisense Oligonucleotide," *PLoS One* 8(11):e81669 (2013), which are hereby incorporated by reference in their entirety).

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of any one of the eIF4E mRNA. The sequences of various eIF4E mRNAs, are readily known in the art and accessible to one of skill in the art for purposes of designing siRNA and shRNA oligonucleotides. siRNA molecules are typically designed to target a region of the mRNA approximately 50-100 nucleotides downstream from the start codon. Methods and online tools for designing suitable siRNA sequences based on the target mRNA sequences are readily available in the art (see, e.g., Reynolds et al., "Rational siRNA Design for RNA Interference," *Nat. Biotech.* 2:326-330 (2004); Chalk et al., "Improved and Automated Prediction of Effective siRNA," *Biochem. Biophys. Res. Comm.* 319(1):264-274 (2004); Zhang et al., "Weak Base Pairing in Both Seed and 3' Regions Reduces RNAi Off-targets and Enhances si/shRNA Designs," *Nucleic Acids Res.* 42(19): 12169-76 (2014), which are hereby incorporated by reference in their entirety). Upon introduction into a cell, the siRNA complex triggers the endogenous RNA interference (RNAi) pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see, e.g., PCT Application Publication Nos. WO 2004/015107 to Giese et al.; WO 2003/070918 to McSwiggen et al.; WO 1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety). Methods of constructing DNA-vectors for siRNA expression in mammalian cells are known in the art (see, e.g., Sui et al., "A DNA Vector-Based RNAi Technology to Suppress Gene Expression in Mammalian Cells," *Proc. Nat'l Acad. Sci. USA* 99(8):5515-5520 (2002), which is hereby incorporated by reference).

Short or small hairpin RNA (shRNA) molecules are similar to siRNA molecules in function, but comprise longer RNA sequences that make a tight hairpin turn. shRNA is cleaved by cellular machinery. Methods and tools for designing suitable shRNA sequences based on the target mRNA sequences (e.g., eIF4E mRNA and/or Bcl6 mRNA sequences) are readily available in the art (see e.g., Taxman et al., "Criteria for Effective Design, Constructions, and Gene Knockdown shRNA Vectors," *BMC Biotech.* 6:7 (2006) and Taxman et al., "Short Hairpin RNA (shRNA): Design, Delivery, and Assessment of Gene Knockdown," *Meth. Mol. Biol.* 629:139-156 (2010), which are hereby incorporated by reference in their entirety). Methods of constructing DNA-vectors for shRNA expression and gene silencing in mammalian cells is described herein and are known in the art (see, e.g., Cheng and Chang, "Construction of Simple and Efficient DNA Vector-based Short Hairpin RNA Expression Systems for Specific Gene Silencing in Mammalian Cells," *Methods Mol. Biol.* 408:223-41 (2007), which is hereby incorporated by reference in its entirety).

Other suitable agents for administration in the methods disclosed herein for purpose of inhibiting eIF4E include microRNAs (miRNAs). miRNAs are small, regulatory, non-coding RNA molecules that control the expression of their target mRNAs predominantly by binding to the 3' untranslated region (UTR). A single UTR may have binding sites for many miRNAs or multiple sites for a single miRNA, suggesting a complex post-transcriptional control of gene expression exerted by these regulatory RNAs (Shulka et al., "MicroRNAs: Processing, Maturation, Target Recognition and Regulatory Functions," *Mol. Cell. Pharmacol.* 3(3):83-92 (2011), which is hereby incorporated by reference in its entirety). Mature miRNAs are initially expressed as primary transcripts known as a pre-miRNAs which are processed, in the cell nucleus, to 70-nucleotide stem-loop structures called pre-miRNAs by the microprocessor complex. The dsRNA portion of the pre-miRNA is bound and cleaved by Dicer to produce a mature 22 bp double-stranded miRNA molecule that can be integrated into the RISC complex. Thus, miRNA and siRNA share the same cellular machinery downstream of their initial processing. Methods of constructing DNA-vectors for miRNA expression and gene silencing in mammalian cells are known in the art (see e.g., Yang N., "An Overview of Viral and Non-Viral Delivery Systems for microRNA," *Int. J. Pharm. Investig.* 5(4):179-181 (2015), which is hereby incorporated by reference in its entirety).

In one embodiment, an eIF4E inhibitor is administered to the subject. In another embodiment, more than one eIF4E inhibitors are administered to the subject. According to this embodiment, a first eIF4E inhibitor and a second (or more) eIF4E inhibitor may be administered simultaneously. According to another embodiment, a first eIF4E inhibitor and a second (or more) eIF4E inhibitor may be administered sequentially.

Depending on the autoimmune disorder to be treated, and the subject, as well as the route of administration, the eIF4E inhibitor may be administered at varying therapeutically effective doses. Therapeutically effective doses of the eIF4E inhibitor(s) as disclosed herein, for the (i) inhibition of TFH cell-mediated differentiation and/or activation or (ii) inhibition of TFH cell differentiation and/or TFH cell activity, may be determined by a person of skill in the art based on many different factors, including, e.g., the particular eIF4E inhibitor to be administered, the means of administration, the target site, the physiological state of the subject, whether other eIF4E or therapeutic agents are administered, the physical state of the subject relative to other medical complications, the severity of the autoimmune disorder, and/or whether treatment is prophylactic or therapeutic. Dosages for administration may be titrated to optimize safety and efficacy (see, e.g., Hong et al., "A Phase 1 Dose-Escalation, Pharmacokinetic, and Pharmacodynamic Evaluation of eIF-4E Antisense Oligonucleotide LY2275796 in Patients with Advanced Cancer," *Clin. Cancer Res.* 17(20):6585-6591 (2011), which is hereby incorporated by reference in its entirety). Likewise, the amount of the eIF4E inhibitor depends on whether an additional eIF4E inhibitor or therapeutic agent is also administered, with higher dosages being required in the absence of an additional eIF4E inhibitor.

In some embodiments, the eIF4E inhibitor is administered in a dose range sufficient to achieve at about 30% to 70% inhibition of eIF4E activity or expression, as determined by the following assay(s). For eIF4E levels, inhibition of eIF4E expression can be shown by immunoblot blot analysis that compares untreated to specimens treated with drug, interfering RNA and other inhibitors. Specimens consist, e.g., of single-cell suspensions of splenocytes isolated using Percoll gradient purification followed by immunoblot of total eIF4E levels. Alternatively, eIF4E levels can be determined in untreated and treated white blood cells using quantification by flow cytometry of permeabilized white blood cells reacted with a fluorescent tagged eIF4E antibody, as described in FIGS. 2O, 3I, and 3J.

Determination of eIF4E activity in vivo should compare untreated to treated animals. Specimens may include single-cell suspensions of splenocytes isolated using Percoll gradient purification followed by plating in X-VIVO media (Lonza) containing 5% human AB serum (Sigma) and Glutamax at 37° C. for one hour and subjected to SuNSET assay for 10 minutes to determine active protein synthesis rates according to manufacturer instructions (AG Scientific) and shown in FIGS. 10A and 14B.

Subject doses of the eIF4E inhibitor described herein may range from about 0.1 µg to 2000 mg per administration, 1 µg to 2000 mg per administration, 10 µg to 2000 mg per administration, 100 µg to 2000 mg per administration, 1 mg to 2000 mg per administration, or any amount there between.

In some embodiments, subject doses of the eIF4E inhibitor described herein range from about 0.1 µg to 1000 mg per administration, 1 µg to 1000 mg per administration, 10 µg to 1000 mg per administration, 100 µg to 1000 mg per administration, 1 mg to 1000 mg per administration, or any amount there between. In some embodiments, the eIF4E inhibitor is administered at a dose range from about 0.1 µg to 100 mg per administration, 0.1 µg to 100 mg per administration, 0.1 µg to 10 mg per administration, 0.1 µg to 1 mg per administration, or 0.1 µg to 100 µg per administration. In other embodiments, the eIF4E inhibitor is administered at a dose range from about 1 µg to 1000 mg per administration, 1 µg to 100 mg per administration, 1 µg to 10 mg per administration, or 1 µg to 1 mg per administration. In further embodiments, the eIF4E inhibitor is administered at a dose range from about 10 µg to 100 mg per administration, 10 µg to 10 mg per administration, or 10 µg to 1 mg per administration.

In some embodiments, the eIF4E inhibitor is administered at a dose of 1.0 mg/kg to 500 mg/kg; 1.0 mg/kg to 400.0 mg/kg; 1.0 mg/kg to 300.0 mg/kg; 1.0 mg/kg to 200.0 mg/kg; 1.0 mg/kg to 100.0 mg/kg; 1.0 mg/kg to 75.0 mg/kg; 1.0 mg/kg to 50.0 mg/kg; 1.0 mg/kg to 25.0 mg/kg; 10.0 mg/kg to 100.0 mg/kg; 10.0 mg/kg to 75.0 mg/kg; 10.0 mg/kg to 50.0 mg/kg; 10.0 mg/kg to 25.0 mg/kg, or any amount there between.

In some embodiments, when the eIF4E inhibitor is 4EGI-1, the dose range extrapolated from a 20-25 gm mouse (25 mg/kg to 75 mg/kg) to a 60 kg to 70 kg human is 1.0 mg/kg to 10.0 mg/kg, with an optimal dose range of 2.0 to 6.0 mg/kg, adjusted for different body mass index (BMI) and body volume differences in increments of 0.5 mg/kg increasing or decreasing from this range (see, e.g., Nair & Jacob, "A Simple Practice Guide for Dose Conversion Between Animals and Humans," *J. Basic Clin. Pharm.* 7(2):27-31 (2016), which is hereby incorporated by reference in its entirety).

In some embodiments, when the eIF4E inhibitor is eFT-4Ei-1, eFT-4Ei-2, or eFT-4Ei-3, the dose range extrapolated from a 20-25 gm mouse (30 mg/kg to 300 mg/kg) to a 60 kg to 70 kg human is 2.4 mg/kg to 24.4 mg/kg, with an optimal dose range of 1.0 to 25.0 mg/kg, adjusted for different body mass index (BMI) and body volume differences in increments of 0.5 mg/kg increasing or decreasing from this range (see, e.g., Nair & Jacob, "A Simple Practice Guide for Dose Conversion Between Animals and Humans," *J. Basic Clin. Pharm.* 7(2):27-31 (2016), which is hereby incorporated by reference in its entirety).

In some embodiments, when the eIF4E inhibitor is an antisense oligonucleotide (e.g., LY2275796), the eIF4E inhibitor is administered at a dose of 1 mg to 1000 mg (e.g., 100 mg, 200 mg, 400 mg, 600 mg, 1000 mg, or any amount there between). For example, the eIF4E inhibitor may be administered at a dose of 100 mg (approximately 1.3 mg/kg assuming an average weight of 75 kg). See, e.g., Hong et al., "A Phase 1 Dose-Escalation, Pharmacokinetic, and Pharmacodynamic Evaluation of eIF-4E Antisense Oligonucleotide LY2275796 in Patients with Advanced Cancer," *Clin. Cancer Res.* 17(20):6585-6591 (2011), which is hereby incorporated by reference in its entirety)

The administering may be carried out in many frequencies over a wide range of times. In some embodiments, the administering is carried out over a period of less than one day. In some embodiments, the administering is carried out over two, three, four, five, six, seven, eight, nine, ten, eleven, twelve, thirteen, fourteen, or more days. In some embodiments, the administering is carried out one or more times per week, over a period of weeks. In other embodiments, the administering is carried out over a period of weeks for one to several months. In various embodiments, the administering is carried out over a period of a month. In other embodiments, the administering may be carried out over a period of one or more years. According to some embodiments, the administering is carried out daily or weekly.

In one embodiment, the eIF4E inhibitor is selective in its activity. Thus, in some embodiments, the eIF4E inhibitor does not directly disrupt or inhibit the activity or differentiation of other T cell types, such as TH1, TH2, TH17, or regulatory T cell (Treg) when administered to a subject.

The methods of the present application is illustrated by the Examples (infra), which demonstrate the ability to prevent TFH cell development and function and to reverse TFH cell function and viability following differentiation as a means of preventing or reversing TFH cell-mediated autoimmune disorders using chemical compounds or interfering RNA inhibition of eIF4E. Data demonstrate that downregulating eIF4E activity by these means in generalized autoimmune disorders as shown by immunization with ovalbumin (OVA/alum). Data demonstrate that downregulating eIF4E activity by these means using a multiple sclerosis-like EAE model inhibits TFH cell-mediated autoimmune pathogenesis, T cell infiltration into the central nervous system (CNS), blocks demyelination of the spinal cord (SC) induced during EAE, and can mitigate disease progression and severity of multiple autoimmune disorders. Data demonstrate that downregulating eIF4E activity by these means inhibits TFH cell-mediated autoimmune pathogenesis and manifestations of autoimmune disease in general as mediated by OVA, and in asthma development induced by *A. fumigatus*. Data demonstrate that downregulating eIF4E activity by these means inhibits TFH cell-mediated autoimmune pathogenesis and manifestations of autoimmune pathogenesis mediated by *S. aureus* bacterial infection. Thus, selective eIF4E inhibition specifically impairs TFH cells and can treat the pathogenesis of multiple autoimmune disorders. Further, treatment of mice during or after induction of experimental autoimmune encephalitis (EAE) results in improved clinical score and decreased infiltration of pathogenic CD4 T cells to the CNS showing the ability to reverse pathogenic autoimmunity.

EXAMPLES

The examples below are intended to exemplify the practice of embodiments of the present application but are by no means intended to limit the scope thereof.

The present application demonstrates the previously unknown ability to treat autoimmune diseases in subjects using specific inhibition of eIF4E or downregulation of eIF4E levels using chemical compound drugs such as 4EGI-1 and derivatives, 4EIR-Cat and derivatives, and ribavirin, or by interfering RNA or antisense oligonucleotides including but not limited to 4E-ASO. Diseases that can be treated include, but are not limited to, general autoimmune reactions, rheumatoid arthritis, asthma, systemic lupus erythematosus (SLE), allergies and food allergies, anaphylactic responses, Jorgen syndrome, multiple sclerosis (MS), autoimmune encephalitis (EAE), lupus nephritis, Type 1 diabetes, juvenile dermatomyositis, autoimmune myasthenia gravis, autoimmune thyroid disease, atherosclerosis and graft versus host disease, among others.

Materials and Methods for Examples 1-9

Study Design

Non-autoimmune studies: Experiments were performed with 5-10 mice per group to achieve statistical significance, and endpoints were pre-determined from previously published studies or expected drug efficacy ranges. Autoimmune studies: Experiments were performed with 10-20 mice per group. Humane endpoints for EAE studies were pre-defined by IACUC protocols.

Animals

C57BL/6 CD45.2, CD45.1 (B6. SJL-Ptprc$^a$ Pepc$^b$/BoyJ), OT2 (B6.Cg-Tg(TcraTcrb)425Cbn/J) (Barnden et al., "Defective TCR Expression in Transgenic Mice Constructed using cDNA-Based Alpha- and Beta-Chain Genes under the Control of Heterologous Regulatory Elements," *Immunol. Cell Biol.* 76(1):34-40 (1998), which is hereby incorporated by reference in its entirety), 2D2 (C57BL/6-Tg (Tcra2D2, Tcrb2D2)1Kuch/J) (Bettelli et al., "Myelin Oligodendrocyte Glycoprotein-Specific T Cell Receptor Transgenic Mice Develop Spontaneous Autoimmune Optic Neuritis," *J. Exp. Med.* 197(9):1073-1081 (2003), which is hereby incorporated by reference in its entirety) and IL-21 vivid verde fluorescent protein (VFP) (B6.Cg-Il21$^{tm1.1Hm}$/DcrJ) (Marnik et al., "Precocious Interleukin 21 Expression in Naive Mice Identifies a Natural Helper Cell Population in Autoimmune Disease," *Cell Rep.* 21(1):208-221 (2017), which is hereby incorporated by reference in its entirety) along with BALB/c IL4$^{4gct}$ (C.129-Il4$^{tm1Lky}$/J) (Mohrs et al., "Analysis of Type 2 Immunity In Vivo with a Bicistronic IL-4 Reporter," *Immunity* 15(2):303-311 (2001), which is hereby incorporated by reference in its entirety) mice were purchased from Jackson Labs and maintained under specific pathogen-free conditions using animal protocols.

Identification of Mouse Cell Subsets by Flow Cytometry

Single cell suspensions were stained with a viability marker diluted 1:1000 in PBS for 10 minutes, washed in PBS, and stained with antibodies to specific cell surface markers. Viability dye, antibody clones, and dilutions used to identify these populations are detailed in Table 2. Identification of cellular subsets in mice is detailed in FIGS. 1A-1N, 3A-3C, and 6A-6C). In brief, the following gating strategy was used to identify mouse TFH cells (CD4$^+$ PD1$^+$ CXCR5$^+$), TFR cells (CD4$^+$ PD1$^+$ CXCR5$^+$ Foxp3$^+$), IL-21$^+$ CD4$^+$ T cells (CD4$^+$ VFP$^{3+}$), IL-4$^+$ CD4$^+$ T cells (CD4$^+$ GFP$^+$) OT2 T cells (CD4$^+$ CD45.2$^+$ Vβ5$^+$), OT2 TFH cells (CD4$^+$ CD45.2$^+$ Vβ5$^+$ PD1$^+$ CXCR5$^+$), 2D2 T cells (CD4$^+$ CD45.2$^+$ Vα3.2$^+$), TFH-like 2D2 T cells (CD4$^+$ CD45.2$^+$ Vα5$^+$ ICOS$^{high}$), plasma cells (B220$^-$ CD138$^+$), plasmablasts (B220$^{mid}$ CD138$^+$), GC B cells (B220$^+$ GL7$^+$ Fas$^+$), Light zone GC B cells (B220$^+$ GL7$^+$ Fas$^+$ CD86$^+$), dark zone GC B cells (B220$^+$ GL7$^+$ Fas$^+$ CXCR4$^+$), IgG1 switched GC B cells (B220$^+$ GL7$^+$ Fas$^+$ IgG1$^+$), OVA-specific GC B cells (B220$^+$ GL7$^+$ Fas$^+$ OVA-647$^+$), skin neutrophils (Ly6G$^+$ CD11b$^+$), lung eosinophils (SiglecF$^+$ CD11c$^-$), brain and SC CD4$^+$ T cells (CD45$^+$ CD4$^+$). CD4$^+$ T cell expression of surface ICOS, PD-1, CXCR5, CD28, SLAM, OX-40 and intranuclear BCL6 was also determined. All flow cytometry procedures were performed on a ZE5 Cell Analyzed (Bio-Rad) and analyzed using FlowJo software (TreeStar).

TABLE 2

Antibodies Used for Immunofluorescence and Quantification

| Antibodies to | Fluorochromes | Clone | Dilution |
|---|---|---|---|
| Extracellular | | | |
| Mouse CD3ε | Alexa Fluor 700 | 500A2 | 1 to 200 |
| Mouse IgG1 | FITC, APC | RMG1-1 | 1 to 200 |
| Mouse IgM | PE/Cy7 | RMM-1 | 1 to 200 |
| Mouse B220 | PE/Cy7 | RA3-6B2 | 1 to 200 |
| Mouse BCL-6 | PE | 7D1 | 1 to 200 |
| Mouse CD11b | BV421 | M1/70 | 1 to 200 |
| Mouse CD11c | PE-Dazzle, BV605 | N418 | 1 to 200 |
| Mouse CD138 | PE | 281-2 | 1 to 200 |
| Mouse CD19 | Alexa Fluor 700 | 6D5 | 1 to 200 |
| Mouse CD4 | FITC, BV421, BV605 | RM4-5 | 1 to 200 |
| Mouse CD4 | PerCP/Cy5.5 | GK1.5 | 1 to 200 |
| Mouse CD44 | PE/Cy7 | IM7 | 1 to 200 |
| Mouse CD44 | FITC | 5035-41.1D | 1 to 200 |
| Mouse CD45 | PerCP/Cy5.5, BV605 | 30-F11 | 1 to 200 |
| Mouse CD45.1 | PerCP/Cy5.5 | A20 | 1 to 200 |
| Mouse CD45.2 | BV421 | 104 | 1 to 200 |
| Mouse CD8α | PerCP/Cy5.5 | 53-6.7 | 1 to 200 |
| Mouse CD86 | PE/Cy7 | GL-1 | 1 to 200 |
| Mouse CD95/FAS | PerCP/Cy5.5 | SA367H8 | 1 to 200 |
| Mouse CXCR4 | BV605 | L276F12 | 1 to 200 |
| Mouse CXCR5 | PE | L138D7 | 1 to 50 |
| Mouse F4/80 | APC, PE/Cy7 | BM8 | 1 to 200 |
| Mouse GL7 | Pacific Blue | GL7 | 1 to 200 |
| Mouse ICOS | PerCP/Cy5.5 | C398.4A | 1 to 200 |
| Mouse Ly6C | BV605 | HK1.4 | 1 to 200 |
| Mouse Ly6G | FITC | 1A8 | 1 to 200 |
| Mouse PD-1 | BV605 | 29F.1A12 | 1 to 200 |
| Mouse SiglecF | PE | S17007L | 1 to 200 |
| Mouse TER119 | APC | TER-119 | 1 to 200 |
| Mouse Vβ5.1, 5.2 | PE/Cy7 | MR9-4 | 1 to 200 |
| Human CD4 | FITC | RPA-T4 | 5 uL/test |
| Human CD3 | Alexa Fluor 700 | OKT3 | 5 uL/test |
| Human CD19 | APC/Cy7 | HIB19 | 5 uL/test |
| Human PD-1 | BV421 | EH12.2H7 | 5 uL/test |
| Human CXCR5 | PerCP/Cy5.5 | J252D4 | 5 uL/test |
| Human ICOS | BV605 | C398.4A | 5 uL/test |
| Human CD45RO | APC | UCHl1 | 5 uL/test |
| Intranuclear | | | |
| Mouse T-bet | PE, Alexa Fluor 647 | 4B10 | 3 uL/test |
| Mouse Foxp3 | BV421 | MF-14 | 3 uL/test |
| Mouse GATA3 | PE, PerCP/Cy5.5 | 16E10A23 | 3 uL/test |
| Mouse FOXP3 | Alexa Fluor 488, 647 | 150D | 3 uL/test |
| Mouse RORγt | PE | Q31-378 | 3 uL/test |
| Mouse/Human BCL-6 | PE | 7D1 | 5 uL/test |
| Intracellular | | | |
| Mouse IFN-γ | APC, PE/Cy7 | XMG1.2 | 1 to 200 |
| Mouse IL-10 | PE/Cy7 | JES5-16E3 | 1 to 200 |
| Mouse IL-13 | PE | EBio13A | 1 to 200 |
| Mouse IL-17 | PE, IL-17A | TC11-18H10.1 | 1 to 200 |

TABLE 2-continued

Antibodies Used for Immunofluorescence and Quantification

| Antibodies to | Fluorochromes | Clone | Dilution |
|---|---|---|---|
| Mouse IL-4 | APC | 11B11 | 1 to 200 |
| Mouse eIF-4E* | | 87/eIF-4E | 1 to 500 |
| *Secondary 1:100 Anti-Mouse IgG1 (Clone: RMG1-1 APC) | | | |
| Puromycin** | | MABE342 | 1 to 200 |
| **Secondary 1:100 Anti-mouse IgG2a (Clone: RMG2a-62 Alexa Fluor 488) | | | |
| Mouse eIF4GI | | D6A6 | 1 to 500 |
| **Secondary 1:1000 Goat anti-rabbit IgG (H + L) cross adsorbed (Clone A11012 Alexa Fluor 594) | | | |
| Immunoflorescence | | | |
| Mouse CD4 | Alexa Fluor 647 | GK1.5 | 1 to 100 |
| Mouse B220 | Alexa Fluor 594 | RA3-6B2 | 1 to 100 |
| Conjugates | | | |
| 2 mg/mL OVA 647 | Alexa Fluor 647 | ThermoFisher | 1 to 500 |
| Viability dye | | | |
| Zombie Fixable Viability Dye | Aqua/BV510 eFluor 660 | | 1 to 1000 1 to 1000 |

OVA Alum Immunizations and 4EGI-1 Treatments

OVA protein (Sigma A5503) was diluted in PBS and then in 20 mg/mL Imject Alum (ThermoFisher 77161) and mixed at room temperature for 30 minutes prior to i.p. injection of 100 µg OVA in 200 µL. When stated, mice were treated i.p. daily from day 0 to 6 or day 0 to 13 (just for TFR analysis) following OVA/Alum immunization with 25 mg/kg 4EGI-1 (MedChemExpress) or from day 7 to 13 following OVA/Alum immunization with 50 mg/kg or 75 mg/kg 4EGI-1. Vehicle control mice were administered 6 µL DMSO in 194 µL PBS i.p.

Detection of Intracellular eIF4E or eIF4GI Levels

Cells were incubated with a live/dead viability marker and extracellular stain prior to fix and permeabilization with Fixation/Permeabilization Solution kit (BD Biosciences) according to manufacturer's instructions to detect intracellular eIF4E and eIF4GI. Concentration and clones of primary and secondary antibodies used for staining detailed in Table 2.

CD4+ T Cell Intranuclear Stain

Single cell suspensions of noted tissues were incubated with a live/dead viability marker and extracellular stain prior to fix and permeabilization with Foxp3/Transcription Factor Staining Buffer set (eBioscience) according to manufacturer's instructions to detect intranuclear transcription factors Foxp3, GATA-3, T-bet, RORγt, or BCL6. Concentration and clones of flow cytometry antibodies used for staining detailed in Table 2.

Cycloheximide Treatment of Mouse Splenocytes for Identification of Short-Lived Proteins Mice were immunized with 100 µg OVA/Alum and 7 days following, spleens were harvested and single-cell suspensions were generated. Splenocytes were incubated in mouse T cell media with 100 µg/mL cycloheximide for 0, 1, 5, and 8 hours at 37° C. Cells were stained with a live/dead viability marker and then for extracellular expression of CD4, PD-1, or ICOS or intranuclear expression of BCL6.

In Vitro Treatment of Mouse Splenocytes with 4EGI-1 and Surface Sensing of Translation (SUnSET) Assay Mice were immunized with 100 µg OVA/Alum and 7 days following, spleens were harvested and single-cell suspensions were generated. Splenocytes were incubated in mouse T cell media (detailed in Silencing of eIF4E in OT2 T cells by lentivirus transduction) with 0-25 µM 4EGI-1 for 4 hours at 37° C. Cells were stained with a live/dead viability marker and then for extracellular expression of CD4, CXCR5, PD-1, or ICOS or intranuclear expression of BCL6. For the SuNSET assay, cells from above were incubated 37° C. with 10 µg/mL puromycin for 10 minutes. Control samples were incubated with puromycin and 100 µg/mL cycloheximide. Cells were incubated with a live/dead viability marker and extracellular stain prior to fixation and permeabilization (BD Biosciences Fixation/Permeabilization Solution) and intracellular staining with anti-puromycin followed by anti-mouse IgG2a antibody conjugated to Alexa Fluor 488.

In Vitro Treatment of Human Lymph Node Cells with 4EGI-1

Discarded, deidentified, reactive, but non-malignant human lymph node single cell suspensions were obtained. Presence of TFH cells was confirmed by identification of $CD4^+$ $CD45RO^+$ T cells that are $PD1^+$ $CXCR5^+$ $BCL6^+$ and $ICOS^+$. Lymph node suspensions were incubated overnight at 37° C. in X-VIVO media (Lonza) containing 5% human AB serum (Sigma) and Glutamax with 0-25 µM 4EGI-1. Cells were then stained with a live/dead viability marker and then for extracellular expression of human CD4, CD45RO, CXCR5, PD-1, or ICOS or intranuclear expression of BCL6. Expression of markers was normalized to % of control (0 µM 4EGI-1) to allow for combined statistical analysis of all 3 patients. Antibody clones and dilutions used to identify these populations are detailed in Table 2.

Induction of Active EAE, Scoring, and 4EGI-1 Dosing

Ten-week old female mice purchased from Jackson Laboratory were subcutaneously injected at two sites with 100 µL $MOG_{33-55}$ emulsified in CFA (Hooke Labs) per flank. On the same day, 6 hours later, and on day 2, mice were injected with 100 ng of pertussis toxin in 200 µL i.p. Mice were monitored daily and scored on a scale of 0-5 where 0, no disease; 1, tail paralysis; 2; hind limb paresis; 3, complete hind limb paralysis; 4, front limb weakness and hind limb paralysis, and 5, moribund state. When stated, mice were either administered 25 mg/kg 4EGI-1 or vehicle i.p. from d 0 to 21 following EAE induction or 75 mg/kg 4EGI-1 or vehicle i.p. from day 12 to 21 following EAE induction and randomization.

Induction of Passive EAE and Pre-Treatment of 2D2 Cells with 4EGI-1

CD4+ T cells were isolated from female 2D2 mice (>90% Vα3.2) and cultured under select Th17 conditions (20 ng/mL mouse IL-6, 20 ng/mL mouse IL-23, 20 ng/mL mouse IL-1β, 50 U/mL human IL-2, 10 µg/mL anti-mouse IL-4, 10 µg/mL anti-mouse IFN-γ) on 10 µg/mL anti-CD3 coated plates for 3 days. TH17 2D2 T cells were removed from activation and treated with vehicle or 20 µM 4EGI-1 for 1 h at 37° C. in vitro prior to transfer of $9.3 \times 10^6$ 2 D2 T cells i.p. per recipient. Mice were given 200 ng pertussis toxin i.p. 6 and 25 d following T cell injection. Animals were monitored daily for 35 days and scored on a scale of 0-5 as described above. At day 35, TFH-like ($ICOS^{high}$) Vα3.2 cells were identified from the spinal cord.

S. aureus Growth and Infection

S. aureus subspecies Rosenbach (ATCC 25923) was grown overnight in TSB broth (Corning). Following quantification, $1\times10^8$ CFU of S. aureus in 100 µL were injected subdermal in the base of the ear pinnae. On days 0 through 7, mice were treated daily with i.p. 25 mg/kg 4EGI-1 or vehicle. On day 8, mice were euthanized and the whole infected ear was collected along with the cervical lymph node (CLN) and blood. Blood was allowed to clot at room temperature, spun at 2,000×g for 30 minutes, and serum was collected and frozen until analysis. Ear thickness was measured with a digital caliper on day 8.

A fumigatus Isolation and Sensitization

A. fumigatus Fresenius (ATCC 13073) was grown for 7 days on potato dextrose agar plates (Thermo Scientific) at 37° C. Conidia were harvested by agitation in a flask with sterile PBS+0.1% Tween-20 and filtered through a 40 µm nylon mesh. Mice were intratracheally sensitized with $1.8\times10^6$ conidia in 50 µL of PBS on days 0, 7, and 11. On day 0 through 17 mice were treated daily with i.p. 25 mg/kg 4EGI-1 or vehicle. On day 18, mice were euthanized and lungs were collected along with mediastinal lymph node (MedLN) and blood. Serum was obtained and stored as described above.

Lentivirus Production

HEK 293T cells were transfected with pTRIPZ plasmid expressing NS shRNA (ACGTGACACGTTCGGAGAATT (SEQ ID NO: 5)) or eIF4E shRNA (GCGT-CAAGCAATCGAGATTTG (SEQ ID NO: 6)) along with psPAX2 and pMD2.G in Lipofectamine™ 2000 and Opti-MEM®. Supernatant was collected 48 hours later and centrifuged at 3000×g for 15 minutes at room temperature. Cell debris pellet was discarded and supernatant was incubated with PEG-it™ (System Biosciences) at 4° C. for 24 to 48 hours and then centrifuged for 1500×g for 30 minutes at 4° C. Supernatant was discarded and viral pellet was resuspended in cold PBS and frozen at −80° C. until use.

Silencing of eIF4E in OT2 T Cells by Lentivirus Transduction

CD4+ T cells were isolated (EasySep™ CD4+ T cell isolation; StemCell) from OT2 mice (>95% Vβ5.1/5.2) using negative selection. OT2 T cells were activated in mouse T cell media (RPMI containing 10% FBS, 55 µM 2-ME, 25 mM HEPES, 100 uM Sodium pyruvate, 2 mM Glutamax, non-essential amino acids, 100 U/mL penicillin, and 100 µg/mL streptomycin) and soluble 1 µg/mL anti-CD28 with 50 U/mL IL-2 on plates coated with 10 µg/mL anti-CD3 for 3 days. Following activation, cells were spin-transfected at $3\times10^6$ cells in 1 mL in 6-well plates with lentivirus and 4 µg/mL dextran (Sigma D9885) at 2,000×g for 60 minutes at 30° C. with no acceleration or break (Kurachi et al., "Optimized Retroviral Transduction of Mouse T Cells for in Vivo Assessment of Gene Function," Nat. Protoc. 12(9):1980-1998 (2017), which is hereby incorporated by reference in its entirety). Following spinoculation, cells were centrifuged and supernatant was decanted and replaced with fresh media. The next day (day 5) 2 µg/mL puromycin (Gibco) and PMA/ionomycin (BioLegend®) are added to the T cells and incubated for 3 days. On day 8, media was replaced and cells were incubated with PMA/ionomycin again for another 3 days. On day 10, it was confirmed that control cells not transfected with virus were >98% dead and $1.5\times10^6$ OT2 NS or OT2 eIF4Esh were transferred i.p. to CD45.1 mice. One day following adoptive transfer, mice were placed on doxycycline diet (200 mg/kg) and remained on this diet for the entire study. After 7 days on doxycycline diet (day 8 following transfer), mice were immunized i.p. with 100 µg of OVA/Alum and 7 days following immunization (15 days following transfer) mice were euthanized for analysis of OT2 T cells.

Mouse Tissue Digest and Processing

Spleens, draining lymph nodes, and brains were dissociated with the plunger-end of a syringe and passed through a 70 µm nylon filter. Splenocytes were subject to RBC lysis with ACK (Ammonium-Chloride-Potassium). Ears were subject to mechanical dissociation with scissors prior to incubation in 1 mL PBS in a 48-well plate with 100 µg/mL Liberase TL and 20 µg/mL DNase I for 1.5 hours at 37° C. Following incubation, cells were further dissociated by passing through a syringe, quenched with PBS+2% FCS, and filtered through a 70 µm nylon filter. Lungs were mechanically dissociated with a razor blade and incubated in a 6 cm dish with 5 mLs RPMI containing 250 µg/mL collagenase, 50 µg/mL Liberase TL, 1 mg/mL hyaluronidase, and 200 µg/mL DNase I for 30 minutes. Following incubation, cells quenched with PBS+2% FCS, and filtered through a 70 µm nylon filter. Ear and lung cells were subject to lymphocyte isolation using a gradient (Lymphocyte Separation Medium; Cellgro). Vertebral columns were flushed with PBS through a 19-gauge needle to remove intact spinal cords. Spinal cords were subject to mechanical dissociation with scissors and incubation in 1 mL PBS with 200 µg/mL DNase I and 50 µg/mL Liberase TL for 30 minutes at 37° C. Following incubation, cells were quenched with PBS+2% FCS and filtered through a 70 µm nylon filter.

Mouse In Vitro CD4+ T Cell Differentiation and Cytokine Production

Naïve CD4+ T cells were isolated (EasySep™ Naïve CD4+ T cell isolation; StemCell) and incubated in mouse T cell media (described under "Silencing of eIF4E in OT2 T cells by lentivirus transduction section") containing soluble 1 µg/mL anti-CD28, cytokines, and anti-cytokine antibodies as detailed for polarization to TH1: 10 ng/mL mouse IL-12, 50 U/mL human IL-2, 10 µg/mL anti-mouse IL-4; TH2: 10 ng/mL mouse IL-4, 50 U/mL human IL-2, 10 µg/mL anti-mouse IFN-γ; TH17: 20 ng/mL mouse IL-6, 10 ng/mL mouse IL-23, 10 ng/mL mouse IL-113, 2 ng/mL human TGF-β1, 50 U/mL human IL-2 10 µg/mL IL-4, 10 µg/mL anti-mouse IFN-γ; and Treg: 2 ng/mL mouse TGFβ, 300 U/mL human IL-2. TH1, TH2, and TH17 differentiation kits (Cytobox) along with human IL-2 were purchased from Miltenyi Biotec. Mouse TGFβ was purchased from BioLegend®. Naïve CD4+ T cells in conditions described above were activated on 10 µg/mL anti-CD3 coated plates for 3 days. Following differentiation, 20 µM 4EGI-1 was added to T cell cultures for 48 hours. Supernatant was removed and cytokine levels were determined using LEGENDPlex Mouse Th Cytokine Panel (BioLegend®).

Polysome Profiling

Mice were treated with OVA/Alum+vehicle or 25 mg/kg 4EGI-1 as described. Following removal of spleens through CD4+ T cell isolation, tissue and cells remained in 0.1 mg/mL cycloheximide until pelleted and flash frozen. Cell pellets were lysed for 10 min on ice with 400 polysome extraction buffer (15 mM Tris-Cl, pH7.4, 15 mM MgCl$_2$, 0.3 M NaCl, 0.1 mg/mL cycloheximide, 100 U superasin, 1% Triton X-100). The lysates were cleared by centrifugation at 13,200×g for 10 minutes. Equal RNA concentrations were layered onto 20-50% sucrose gradients. Gradients were sedimented at 151,263×g for 103 min in a SW55 Ti rotor at 4° C. An ISCO UA-6 (Teledyne) fraction collection system was used to collect 12 fractions, which were immediately mixed with 1 volume of 8M guanidine HCl. RNA was precipitated from polysome fractions by ethanol precipitation and dissolved in 20 µL of $H_2O$. Briefly, fractions were vortexed for 20 seconds. 600 µL of 100% ethanol was added, and fraction was vortexed again. Fractions were incubated overnight at −20° C. to allow for complete RNA precipitation. Fractions were centrifuged at 13000 rpm for 30 minutes at 4° C. The RNA pellet was washed with 75% ethanol. The pellet was resuspended in 400 µL 1× Tris-EDTA (pH 8.0). 0.1 volumes of 3M NaOAc (pH 5.3) and 2.5 volumes 100% ethanol were added and fractions were incubated at −20° C. to precipitate RNA. Fractions were centrifuged at 13,0000 rpm for 30 minutes at 4° C. The RNA pellet was washed with 75% ethanol. RNA was resuspended in 20 µL $H_2O$. Total RNA samples were isolated from cell lysates using Trizol per the manufacturer's instructions.

RNA Sequencing, Data Analysis, and Data Availability

Fractions containing 4 or more ribosomes (considered well-translated) were pooled and RNA quality was measured by a Bioanalyzer (Agilent Technologies). RNA-seq was carried out by the New York University School of Medicine Genome Technology Core using the Illumina HiSeq 4000 single read. The low-quality reads (less than 20) were trimmed with Trimmomatic (Bolger et al., "Trimmomatic: a Flexible Trimmer for Illumina Sequence Data," *Bioinformatics* 30(15):2114-2120 (2014), which is hereby incorporated by reference in its entirety) (version 0.36) with the reads lower than 35 nt being excluded. The resulted sequences were aligned with STAR (Dobin et al., "STAR: Ultrafast Universal RNA-Seq Aligner," *Bioinformatics* 29(1):15-21 (2013), which is hereby incorporated by reference in its entirety) (version 2.6.0a) to the hg38 reference genome in the single-end mode. The alignment results were sorted with SAMtools (Li et al., "The Sequence Alignment/Map Format and SAMtools," *Bioinformatics* 25(16):2078-2079 (2009), which is hereby incorporated by reference in its entirety) (version 1.9), after which supplied to HTSeq (Anders et al., "HTSeq—A Python Framework to Work with High-Throughput Sequencing Data," *Bioinformatics* 31(2):166-169 (2015), which is hereby incorporated by reference in its entirety) (version 0.10.0) to obtain the feature counts. The feature counts tables from different samples were concatenated with a custom R script. To examine differences in transcription and translation, total mRNA and polysome mRNA were quantile-normalized separately. Regulation by transcription and translation and accompanying statistical analysis was performed using RIVET (Ernlund et al., "RIVET: Comprehensive Graphic User Interface for Analysis and Exploration of Genome-Wide Translatomics Data," *BMC Genomics* 19:809 (2018), which is hereby incorporated by reference in its entirety), where significant genes were identified as P<0.05 and >1 log fold change. Reactome pathway analysis was performed on genes that were up- and down-regulated by transcription and translation using Metascape (Zhou et al., "Metascape Provides a Biologist-Oriented Resource for the Analysis of Systems-Level Datasets," *Nat. Commun.* 10:1523 (2019), which is hereby incorporated by reference in its entirety). Pathway analysis and enrichment plots of the top 100 genes that were the most regulated by transcription and/or translation were generated using DAVID (Huang et al., "Systematic and Integrative Analysis of Large Gene Lists Using DAVID Bioinformatics Resources," *Nat. Protoc.* 4:44-57 (2009), which is hereby incorporated by reference in its entirety) and Metascape. Prediction of transcription factors of the same list of 100 genes was performed using Enrichr (Chen et al., "Enrichr: Interactive and Collaborative HTML5 Gene List Enrichment Analysis Tool," *BMC Bioinformatics* 14:128 (2013), which is hereby incorporated by reference in its entirety) (TRANSFAC and JASPER PWM program) and PASTAA (Roider et al., "Predicting Transcription Factor Affinities to DNA from a Biophysical Model," *Bioinformatics* 23:134-141 (2007), which is hereby incorporated by reference in its entirety) online tool. Genes enriched in TFH cells was determined from GSE16697 (Johnston et al., "Bcl6 and Blimp-1 are Reciprocal and Antagonistic Regulators of T Follicular Helper Cell Differentiation," *Science* 325(5943):1006-1010 (2009), which is hereby incorporated by reference in its entirety) and similar genes between datasets were determined using Venny.

CD4$^+$ T Cell Stimulation and Intracellular Stain.

Single cell suspensions of noted tissues were resuspended in T cell media with 1× PMA/Ionomycin (cell activation cocktail; BioLegend®) and 1× brefeldin A (BioLegend®) for 5-6 hours at 37° C. Following stimulation, cells were incubated with a live/dead viability marker and extracellular stain prior to fix and permeabilization with Fixation/Permeabilization Solution kit (BD Biosciences) according to manufacturer's instructions to detect intracellular cytokines IL-17A, IFN-γ, or IL-13. Concentration and clones of flow cytometry antibodies used for staining detailed in Table 2.

Immunofluorescence (IF) and Quantification of CD4$^+$ T Cells in B Cell Zones in the Spleen Spleens from OVA/Alum immunized mice treated with vehicle or 4EGI-1 were harvested, embedded in OCT, and frozen immediately on dry ice. Five-micron thick cryosections were cut and fixed in acetone for 10 min. Slides were blocked with 1% BSA and stained with anti-CD4 conjugated to Alexa Fluor 647 and anti-B220 Alexa Fluor 555. Antibody clones are detailed in Table 2. Following 3 washes with PBS, slides were mounted with DAPI fluoromount (VECTASHIELD) and sealed with clear nail polish. Staining was visualized and tiled using a Zeiss 700 laser scanning inverted confocal microscope.

B cell (Alexa fluor 555) and CD4$^+$ T cell (Alexa fluor 647) channels were split using FIJI, and B cell zones were manually outlined. This outline was overlaid upon the CD4$^+$ T cell stain and intensity of CD4$^+$ T cell staining within these zones was measured using FIJI and normalized to a fixed area of 500 microns OVA-Specific IgG1 Enzyme-Linked Immunospot (ELISPOT)

PVDF-coated 96-well plates (Millipore) were activated with methanol for 2 minutes, washed with PBS, and coated with 4 µg/mL OVA overnight at 4° C. Plates were blocked with 1% BSA for 2 hours at 37° C. prior to incubation with 1×10$^7$ splenocytes in RPMI containing 2% Ultra-low IgG FCS, 55 µM 2ME, and 100 U/mL penicillin and 100 µg/mL streptomycin in the top well. Cells were diluted by 1/2 each row going down the plate and incubated immobile overnight at 37° C. Plates were washed with water+0.05% Tween 20 for 5 min prior to 3 washes in PBS+0.05% Tween-20 for 10 minutes. Plates were incubated with 1:1000 HRP-coupled goat anti-mouse IgG1 antibody (Southern Biotech) in PBS+0.05% Tween 20 for 2 h prior to 3 washes in PBS+0.05% Tween 20 and incubation in tetramethylbenzidine (TMB) ELISA substrate buffer (ThermoFisher). Plates were washed once in distilled deionized water and spots were manually enumerated and antibody-secreting cells (ASC) per million splenocytes was determined.

Enzyme-Linked Immunosorbent Assay (ELISA)

For quantification of OVA-specific IgG1, high-binding 96-well plates (Costar) were coated with 10 µg/mL OVA protein. For *S. aureus*-specific IgG1, plates were coated with heat-killed *S. aureus* (heat-killed at 80° C. for 30 min). For total IgE, plates were coated with 2 µg/mL rat anti-mouse IgE (Southern Biotech). Following overnight incubation at 4° C., plates were blocked with 1% BSA for 30 min at 37° C. After blocking, serum (diluted 1/20 initially then 1/2 down the plate) was incubated at 37° C. for 2 hours, plates were washed 3 times in PBS and then incubated with 1:1000 anti-mouse IgG1-HRP (Southern Biotech) or anti-mouse IgE-HRP (Southern Biotech) for 1 hour at 37° C. Plates were washed 3 times in PBS and incubated with TMB substrate. Following development, TMB Stop Solution (BioLegend®) was added and plates were read at 405 nm.

Immunohistochemistry (IHC) and Quantification

Lungs fixed in 4% PFA (ThermoFisher) and spinal cords fixed in 10% buffered formalin (Leica) were incubated overnight and moved to 70% ethanol prior to ethanol dehydration, xylene incubation, and paraffin embedding. Five-micron thick sections of lung were stained with hematoxylin and eosin (H&E), Periodic Acid-Schiff (PAS), or Masson's Trichrome Stain (MTS). Spinal cords were stained with H&E or Luxol fast blue and hematoxylin (LFB-H). Staining was visualized with an EVOS FLc microscope.

LFB-H images imported into FIJI underwent color deconvolution to isolate myelin staining. A binary image was generated and % myelination of the spinal cord was calculated. Spinal cords from mice not subjected to EAE were set to 100% and all other samples from the same group were normalized. H&E images imported into FIJI underwent color deconvolution to isolate hematoxylin staining. A binary image was generated and % infiltration of the spinal cord of was calculated.

Immunofluorescence (IF) Staining for CD4+ and CD19+ Cells in Spinal Cord

Five-micron sections of paraffin embedded tissue were stained with Akoya Biosciences® Opal™ multiplex automation kit reagents unless stated otherwise. Automated staining was performed on Leica BondRX® autostainer. The protocol was performed according to manufacturers' instructions with primary antibodies to CD19 (Cell Signaling Technology, cat #90176) and CD4 (Cell Signaling Technology, cat #25229). Briefly, all slides underwent sequential epitope retrieval with Leica Biosystems epitope retrieval 2 solution (EDTA based, pH9, Cat. AR9640), primary and secondary antibody incubation and tyramide signal amplification (TSA) with Opal® fluorophores Op690 and Op520. Primary and secondary antibodies were removed during epitope retrieval steps while fluorophores remain covalently attached to the epitope. Semi-automated image acquisition was performed on a Vectra® Polaris multispectral imaging system. After whole slide scanning at 10× the tissue was manually outlined to select fields for multispectral imaging at 20×. Phenochart® software from Akoya Biosciences was used for spectral unmixing of the whole slide scans. Scans were imported into QuPath and representative images were exported into FIJI.

OT2 T Cell Pre-Treatment with 4EGI-1 and CFSE Dilution

OT2 T cells were isolated and activated, as described in "Silencing of eIF4E in OT2 T cells by lentivirus transduction" and labeled with CFSE (Invitrogen). Cells were treated in vitro with vehicle or 20 μM 4EGI-1 for 1 hour at 37° C. and washed before transfer of $5 \times 10^6$ OT2 T cells i.p. per CD45.1 recipient. Following 24 hours, animals were immunized with 100 μg OVA alum and 3 days following, frequency of OT2 T cells that had divided, as determined by CFSE stain, was calculated.

OT2 T Cell Pre-Treatment with 4EGI-1

For functional TFH studies: OT2 T cells were isolated and activated, as described, and treated with vehicle or 20 μM 4EGI-1 for 1 hour at 37° C. in vitro prior to transfer of $2 \times 10^6$ OT2 T cells i.p. per CD45.1 recipient. Recipient animals were immunized with 100 μg OVA alum 4 days prior. Three days following transfer and 7 days following initial immunization, OT2 T cells that had formed TFH cells were determined.

For long-term studies: OT2 T cells were isolated and activated, as described, and treated with vehicle or 20 μM 4EGI-1 for 1 h at 37° C. in vitro prior to transfer of $12 \times 10^6$ OT2 T cells i.p. per CD45.1 recipient. OT2 T cells were enumerated 34 days post transfer and intracellular levels of eIF4E were determined.

Statistics

Values represent the mean±SEM from 2-3 independent experiments with 5-20 mice per group. Statistical calculations described below were performed with Prism (GraphPad). Levels of cells in control mice are indicated by horizontal dotted line where applicable. Comparison of three or more groups was performed by a one-way ANOVA test followed by Tukey's post-hoc analysis and data from only two groups were analyzed by a two-tailed unpaired t test to determine statistical significance. In the figures, statistically significant differences are indicated: *$P<0.05$, $P<0.01$, *$P<0.001$.

Data Availability

Genome-wide trancriptomic and translatomic data were analyzed using the on-line platform RIVET. All data are publicly available at (GEO # to be assigned). Source data for all main and Extended Data figures are available in the Supplementary Dataset.

Example 1—Partial Pharmacologic Inhibition of eIF4E Activity Inhibits CD4+ T Cell Differentiation to TFH Cells but not Other T Helper Cell Subsets Since TH1 and TFH cells require high levels of mTORC1 activity, the sensitivity of all T helper cell subsets, including Tregs, to reduction in eIF4E activity with regard to their differentiation and effector functions was investigated. The small molecule inhibitor 4EGI-1 blocks engagement of eIF4E with eIF4G, thereby downregulating eIF4E-mediated mRNA translation (Sekiyama et al., "Molecular Mechanism of the Dual Activity of 4EGI-1: Dissociating eIF4G from eIF4E but Stabilizing the Binding of Unphosphorylated 4E-BP1," Proc Natl Acad Sci USA 112(30):E4036-E4045 (2015), which is hereby incorporated by reference in its entirety). Dose level and frequency of administration for 4EGI-1 to mice were established at 25 mg/kg daily, the same as in the tumor inhibition setting (Sekiyama et al., "Molecular Mechanism of the Dual Activity of 4EGI-1: Dissociating eIF4G from eIF4E but Stabilizing the Binding of Unphosphorylated 4E-BP1," Proc Natl Acad Sci USA 112(30): E4036-E4045 (2015), which is hereby incorporated by reference in its entirety). At this dose and frequency, 4EGI-1 inhibited eIF4E cap-dependent protein synthesis in the CD4+ T cell compartment by approximately 30% (FIG. 1A) and as shown later, was well tolerated. Different animal models were used to determine the effect of downregulation of eIF4E activity on different T cell subsets. To assess the effect of downregulation of eIF4E activity on TH1 and TH17 cells, mice were infected sub-dermally with Staphylococcus aureus in the ear pinnae, an established model for TH1 and TH17 cell induction, then treated with vehicle or 4EGI-1 throughout infection (FIG. 2A). 4EGI-1 downregulation of eIF4E activity at these levels had no effect on differentiation or effector function of TH1 cells (T-bet+ or IFN-γ+) or TH17 cells (RORγT+ or IL17A+) in the skin, or on levels of general skin inflammation, measured by ear thickness and skin neutrophil levels (FIGS. 1B-1I; FIGS. 2B-2E). Moreover, differentiated TH1 or TH17 cells treated in vitro with 4EGI-1 were not altered in levels of secretion of IFN-γ or TNF-α (TH1 cells), or IL-17A or IL-17F (TH17 cells) (FIGS. 1J-1N). Partial eIF4E inhibition therefore does not affect TH1 or TH17 cell induction or function.

Figures 2A, 2B, 2C, 2D, 2E, 2F, 2G:
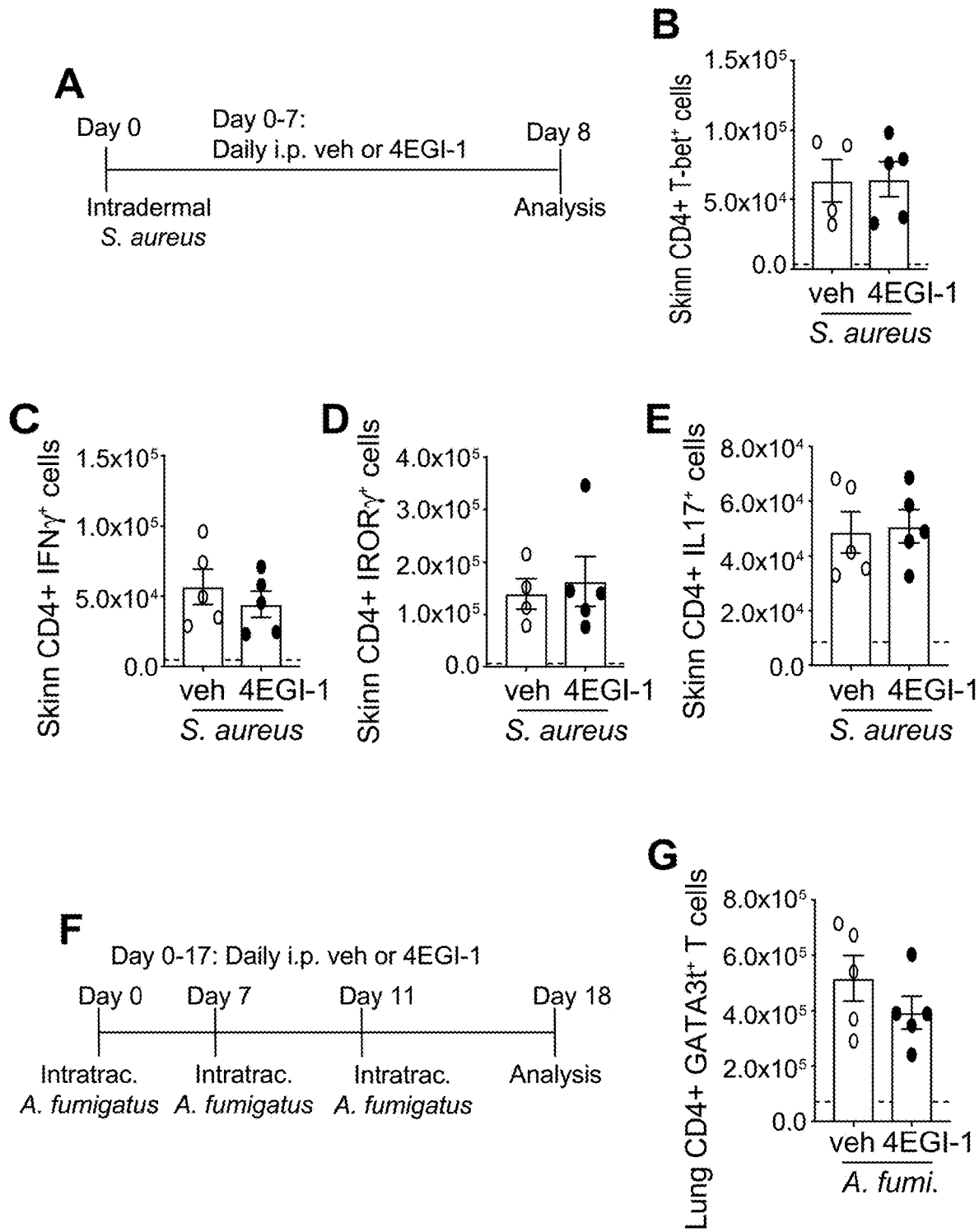
Figure 2H:
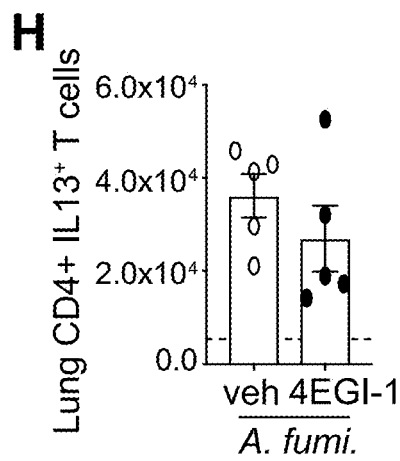
Figure 2I:
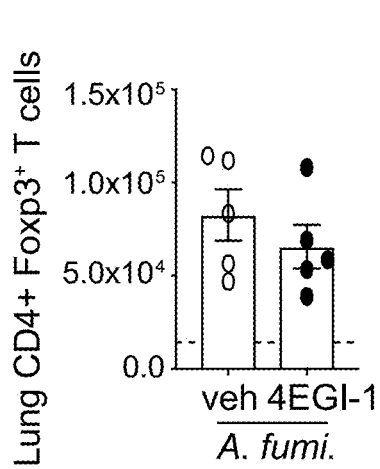
Figures 3A, 3B, 3C, 3D, 3E:
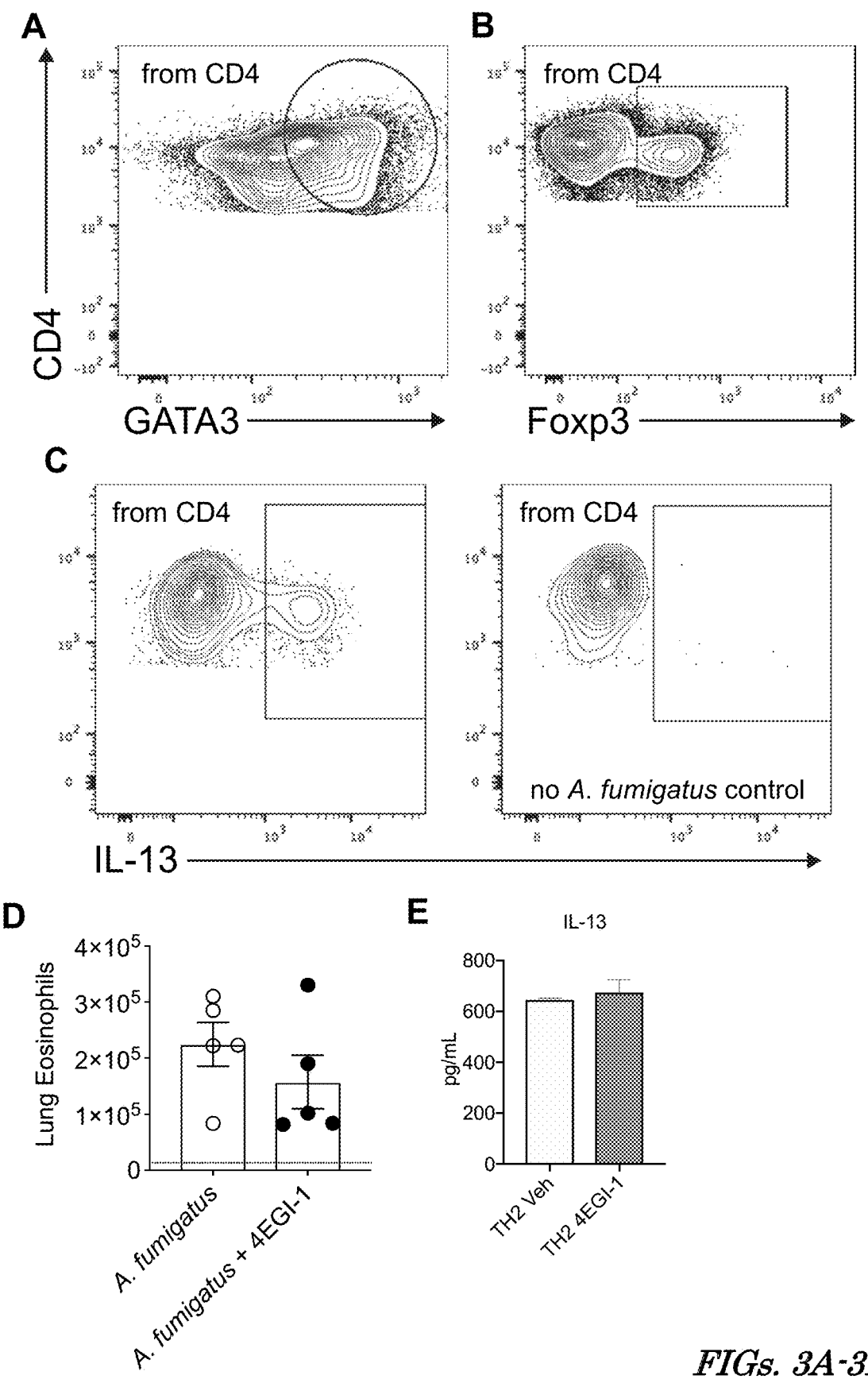
Figures 3F, 3G:
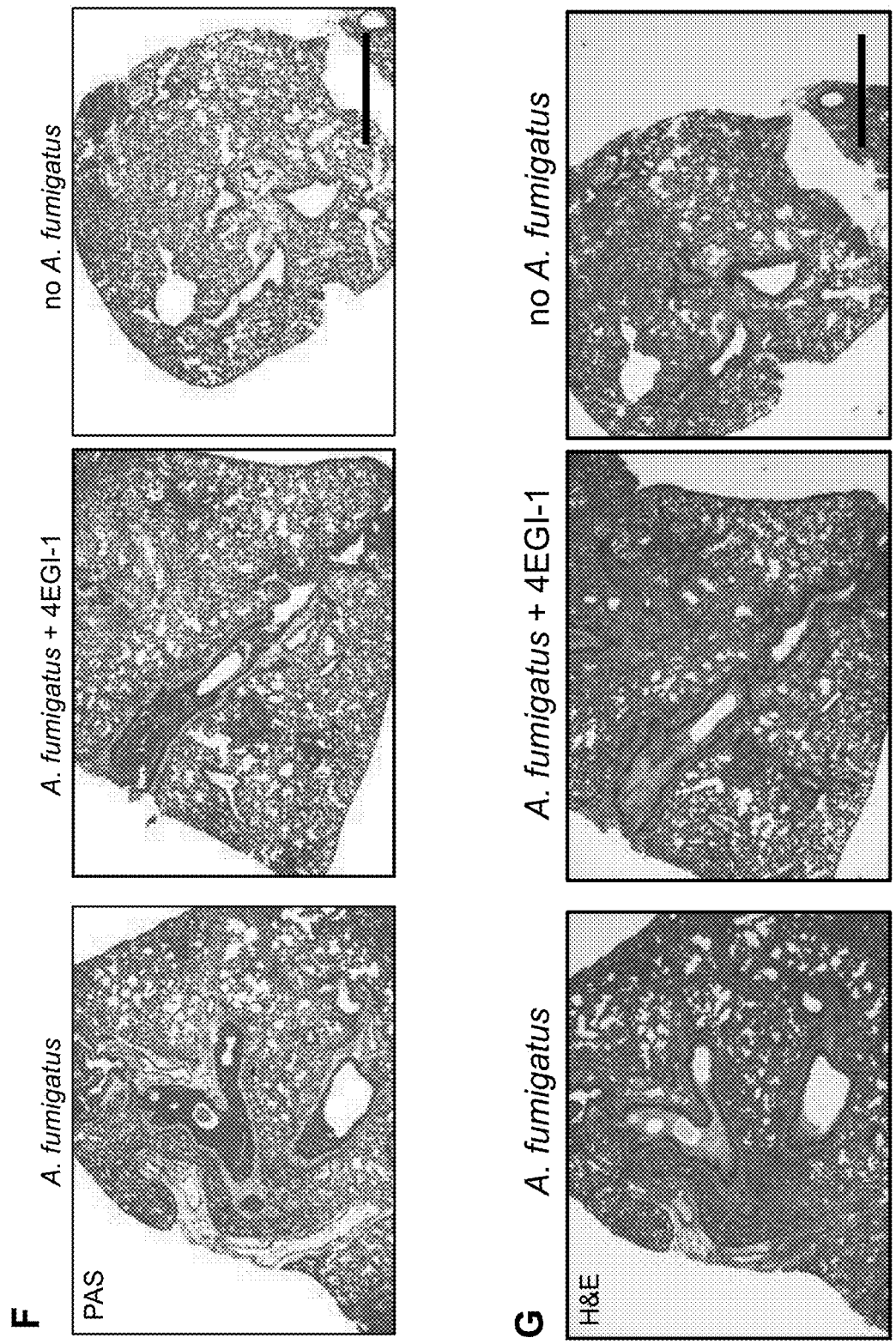

To determine the effect of partial eIF4E inhibition on TH2 cells and Tregs, an established model of airway disease caused by repeat sensitization to *Aspergillus fumigatus* conidia was used. Mice were treated with vehicle or 4EGI-1 throughout sensitization (FIG. 2F). Treatment with 4EGI-1 had no effect on levels of pulmonary TH2 cells (GATA3$^+$ or IL-13$^+$), Tregs (Foxp3$^+$), eosinophils, mucin production, or airway inflammation (FIGS. 2G-2I; FIGS. 3A-3G). Further, treatment of in vitro differentiated TH2 cells with 4EGI-1 did not affect secretion of IL-13, a pathogenic TH2 cytokine (FIG. 3E). Therefore, partial eIF4E inhibition does not alter TH2 or Treg-dependent differentiation or function.

Figure 2J:
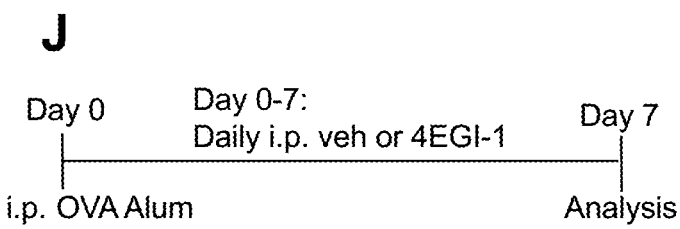
FIG. 2J is a scheme for mice immunized with OVA/Alum i.p. and treated with vehicle or 25 mg/kg 4EGI-1.
Figure 2K:
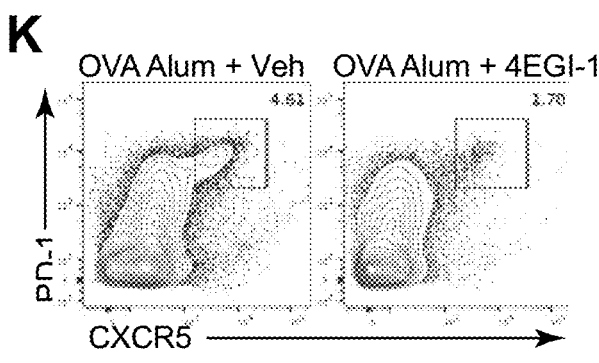
FIG. 2K shows representative flow cytometry identification of CD4+ TFH cells in mice administered vehicle or 4EGI-1 treatment.
Figure 2L:
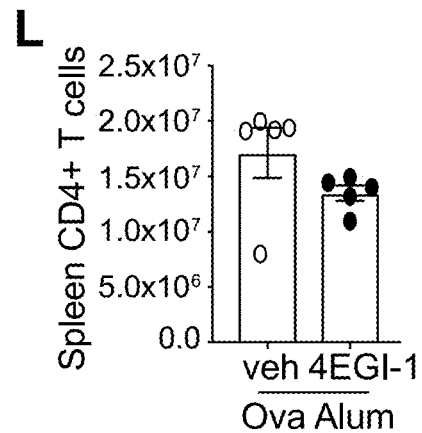
FIGS. 2L-2M are graphs showing quantification of CD4+ T cells and TFH cells for splenic CD4+ T cells (FIG. 2L) and TFH cells (FIG. 2M).
Figure 2M:
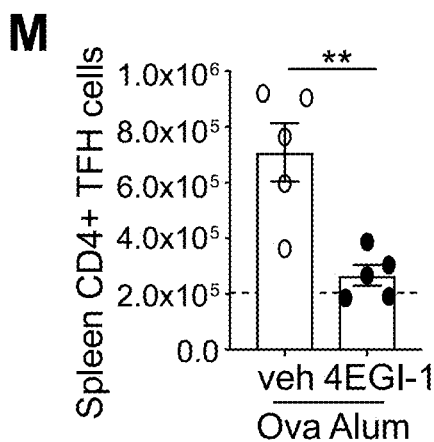
Figures 3H, 3I, 3J:
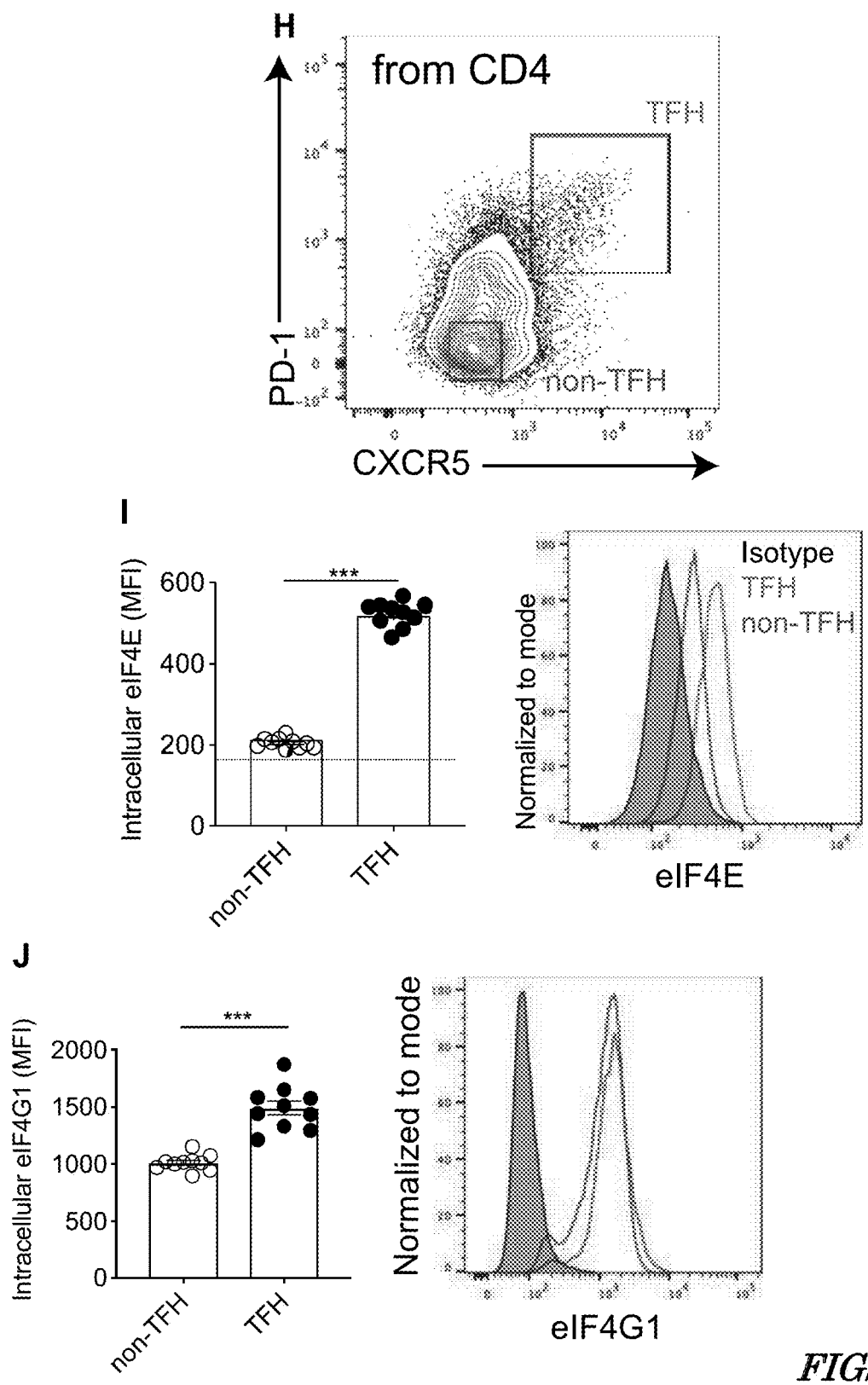

Lastly, to examine the effect of eIF4E downregulation on TFH cell development, mice were immunized with ovalbumin in alum (OVA/Alum), an established method for TFH cell induction, and treated with vehicle or 4EGI-1 throughout the response (FIG. 2J). While 4EGI-1 treatment did not alter overall CD4$^+$ T cell numbers, TFH cells in spleen were significantly reduced (3.5-fold; FIGS. 2K-2M). To understand the acute sensitivity of TFH cells to modest downregulation of eIF4E activity, eIF4E levels were examined in CD4$^+$ T cells and TFH cells. It was found that TFH cells express ~3-fold increased levels of eIF4E and slightly increased levels of eIF4GI (the major eIF4G member) compared to non-TFH CD4$^+$ T cells (FIGS. 3H-3J). These data suggest a potential greater requirement for higher levels of eIF4E in TFH cell development and function, which was next explored.

Example 2—Intrinsically Higher Levels of TFH Cell eIF4E are Essential for Strong Translation of mRNAs that Mediate TFH Cell Differentiation and Maintenance Whether the impact of downregulation of eIF4E activity on TFH cell differentiation is CD4$^+$ T cell intrinsic was determined by engineering reduced levels of eIF4E in a select CD4$^+$ T cell compartment. CD45.2 OT2 T cells are specifically activated by OVA peptide. OT2 T cells were transduced with a lentivirus expressing doxycycline (Dox)-inducible non-silencing (NS) or eIF4E shRNAs, puromycin selected, and transferred into CD45.1 congenic recipients (FIG. 2N). The eIF4E shRNA used was previously established to be eIF4E specific (de la Parra et al., "A Widespread Alternate form of Cap-Dependent mRNA Translation Initiation," *Nat. Commun.* 9:3068 (2018), which is hereby incorporated by reference in its entirety). Animals were placed on a Dox diet for the entire study. Seven days following Dox addition, eIF4E silencing in spleen and blood transduced OT2 T cells was confirmed to be 3-fold lower similar, to that of CD4$^+$ T cells compared to TFH cells, and continued throughout the study (FIG. 2O; FIG. 3K). While there was no impact on the level of OT2 T cells in the spleen (FIG. 2P), eIF4E shRNA-transfected OT2 T cells formed significantly fewer TFH cells (3-fold) than control NS OT2 cells (FIG. 2Q). Thus, higher levels of CD4$^+$ T cell intrinsic eIF4E is required for TFH cell differentiation.

Example 3—Higher Levels of eIF4E are Required for Selective Translation of mRNAs that Drive TFH Cell Differentiation, Function, and Maintenance Next, the question of which TFH cell-dependent programs require intrinsically higher levels of eIF4E for translation was investigated. Mice were immunized with OVA/alum and treated with vehicle or 4EGI-1 (FIG. 4A). Then, CD4$^+$ T cells were isolated and RNA sequencing (RNAseq) was performed on total mRNA (transcriptome) and well-translated (>4 ribosome) polysome-associated mRNA to establish individual mRNA translation activities based on ribosome content. Total mRNA was compared to levels of well-translated mRNAs (translatome). Performing the study on CD4$^+$ T cells allows comparison of an equal cell population between each group, since 4EGI-1 does not impact CD4$^+$ T cell numbers but does impair translation of mRNAs required for their differentiation to TFH cells, providing an unbiased identification of CD4$^+$ T cell programs dependent on higher levels of eIF4E for TFH cell differentiation. The open source analysis tool Ribosomal Investigation and Visualization to Evaluate Translation (RIVET) (Ernlund et al., "RIVET: Comprehensive Graphic User Interface for Analysis and Exploration of Genome-Wide Translatomics Data," *BMC Genomics* 19:809 (2018), which is hereby incorporated by reference in its entirety) was used for genome-wide transcriptomic and translatomic analysis. 641 mRNAs that were significantly altered in abundance and not translation activity (transcription alone), 667 mRNAs altered in translation alone without a change in abundance, and 64 mRNAs altered in both transcription and translation were identified (FIGS. 4B-4C). Only a small number of mRNAs changed in abundance or translation in CD4$^+$ T cells treated with 4EGI-1 (~4%). Of these, the majority were downregulated in transcription and/or translation by partial inhibition of eIF4E activity, with 61% of mRNAs reduced in abundance and 79% reduced in translation (FIG. 4C; FIG. 5A). Pathway analysis was performed on the top ranked (changed) mRNAs by 4EGI-1 partial inhibition of eIF4E. This analysis identified pathways and associated mRNAs that are particularly sensitive to only moderate (30%) inhibition of eIF4E activity in CD4$^+$ T cells.

Figure 4D:
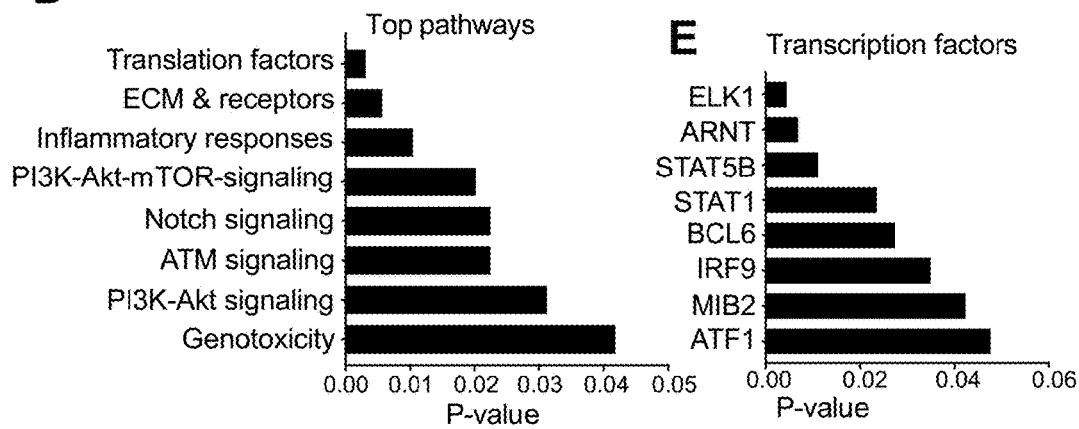
Figure 4E:
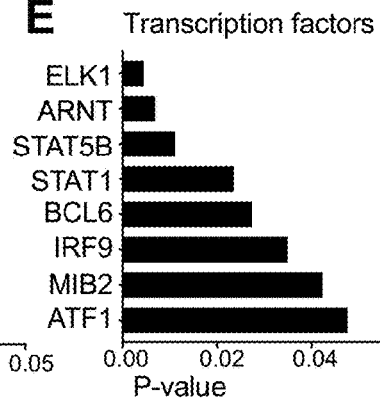

Top pathways that were downregulated in CD4$^+$ T cells with reduced eIF4E activity include eIF4E itself, suggesting a feed-forward mechanism for TFH cell translational upregulation of specification mRNAs, PI3K/Akt/mTOR signaling proteins that are also consistent with such a mechanism, extracellular matrix (ECM), membrane receptor expression proteins, and inflammatory immune responses among others, which are all involved in TFH cell differentiation and function (FIG. 4D). Transcription factors downregulated either in transcription, translation, or both by 4EGI-1 treatment included the canonical established transcription factors that regulate TFH cell development, including a small decrease in BCL6, STAT1, and ELK1, a member of the ternary complex factor (TCF) induced by JNK signaling (FIG. 4F).

Figure 4F:
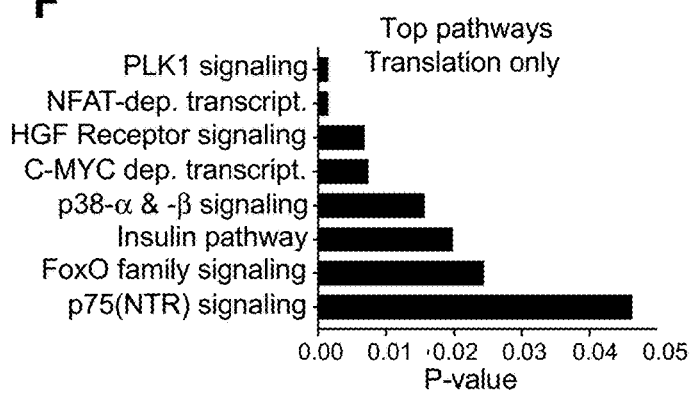
Figures 5A, 5B, 5C, 5D, 5E:
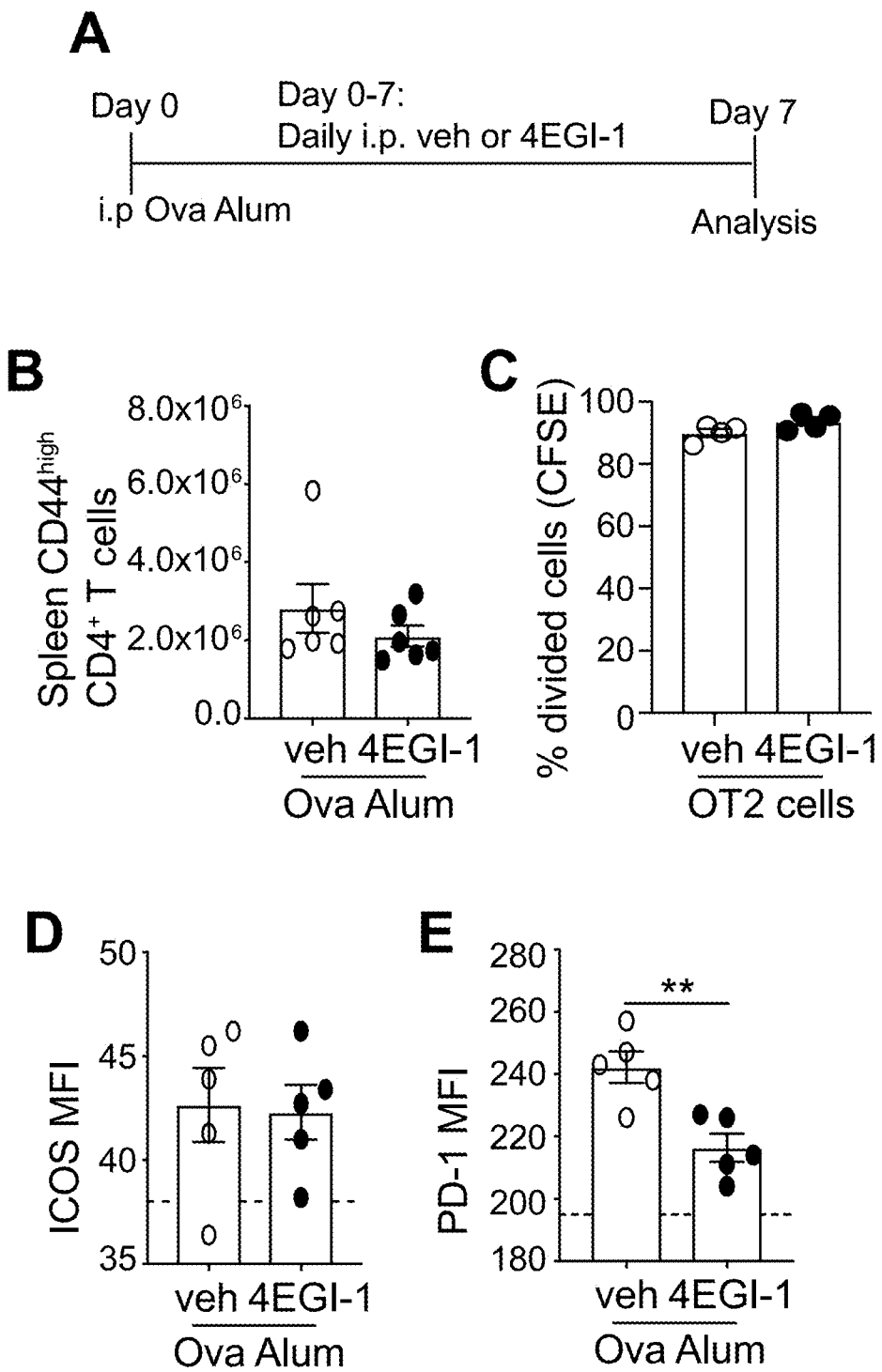

Pathway analysis of mRNAs that were only translationally downregulated by 30% inhibition of eIF4E included calcineurin-regulated NFAT-dependent transcription, c-MYC activation, and Foxo family signaling, among others (FIG. 4F). NFAT1 and NFAT2 signaling is essential for TFH cell development, including IL-21 production (Martinez et al., "Cutting Edge: NFAT Transcription Factors Promote the Generation of Follicular Helper T Cells in Response to Acute Viral Infection," *J. Immunol.* 196(5):2015-2019 (2016), which is hereby incorporated by reference in its entirety), MYC activated pathways which are involved in IL2$^+$ T cell development and are precursors of TFH cells (DiToro et al., "Differential IL-2 Expression Defines Developmental Fates of Follicular Versus Nonfollicular Helper T Cells," *Science* 361:6407 (2018), which is hereby incorporated by reference in its entirety), and Foxo signaling which controls expression of BCL6 (Hedrick et al., "FOXO Transcription Factors Throughout T Cell Biology," *Nat. Rev. Immunol.* 12(9):649-661 (2012), which is hereby incorporated by reference in its entirety). Thus, partial inhibition of eIF4E activity selectively impairs translation of mRNAs that are essential for cellular programs required for CD4+ T cell differentiation to TFH cells, including NFAT and Foxo which promote BCL6 expression.

Figure 6A:
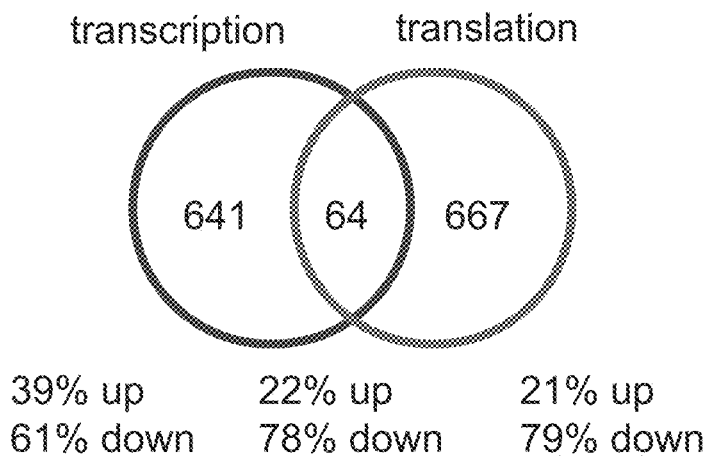
FIGS. 6A-6C illustrates the modulation of the transcriptome and translatome in CD4$^+$ T cells by downregulation of eIF4E function by 4E.
Figure 6B:
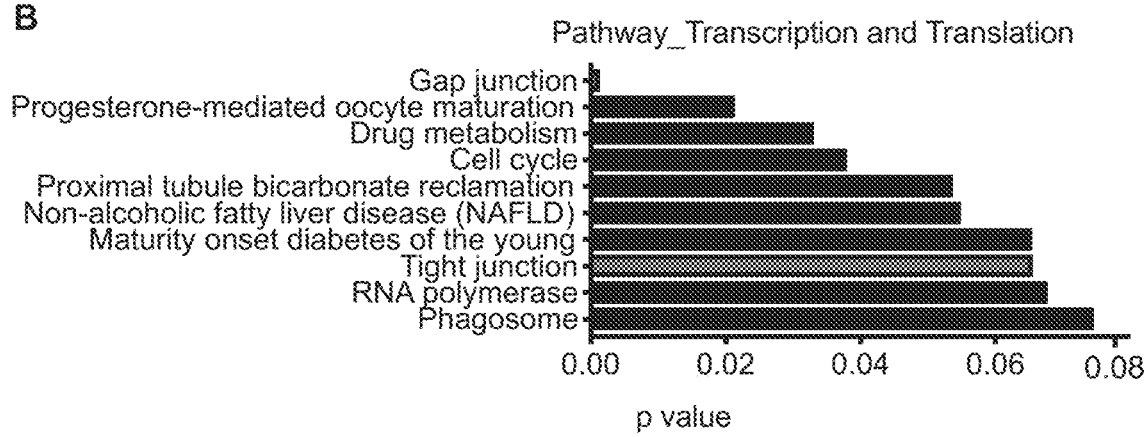
Figure 6C:
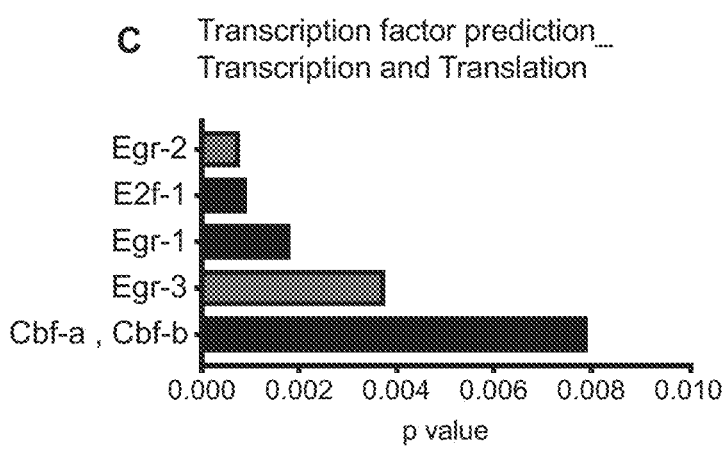

While the list of mRNAs downregulated by reduced eIF4E activity at both transcriptional and translational levels was smaller, pathway analysis identified gap and tight junction functions that are required for retention of TFH cells in GCs (DiToro et al., "Differential IL-2 Expression Defines Developmental Fates of Follicular Versus Nonfollicular Helper T Cells," *Science* 361:6407 (2018), which is hereby incorporated by reference in its entirety) (FIG. 6B). Notably, Egr transcription factors were reduced in expression (FIG. 6C) and are required for expression of BCL6 and cMyc (Ogbe et al., "Early Growth Response Genes 2 and 3 Regulate the Expression of Bcl6 and Differentiation of T Follicular Helper Cells," *J. Biol. Chem.* 290(33):20455-20465 (2015), which is hereby incorporated by reference in its entirety).

Figure 4G:
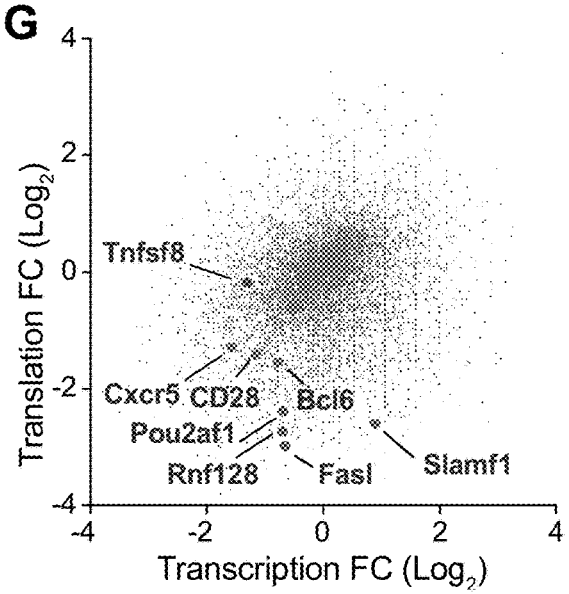

Next, the transcriptomic and translatomic data were analyzed by $\log_2$ scatter plots to simultaneously visualize changes in specific mRNAs with partial reduction in eIF4E activity (FIG. 4G). Among the mRNAs strongly dependent on higher levels of eIF4E and transcriptionally and/or translationally downregulated were those encoding well-established essential proteins for TFH cell development and function. These included those that are dependent on increased levels of eIF4E for their transcription through higher eIF4E-dependent translation of associated transcription factors and/or for their translation and are essential for TFH cell differentiation (CD28, Pou2af1, Bcl6), migration (CXCR5), and expression of co-receptors involved in TFH cell function and maintenance (Slamf1, Fasl, Tnfsf8, CD28).

Figure 4H:
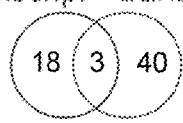

These results were also queried against a list of mRNAs that were previously found to be increased in expression in TFH cells compared to non-TFH CD4+ T cells, which was obtained from a comprehensive study that characterized the TFH cell transcriptome (Johnston et al., "Bcl6 and Blimp-1 are Reciprocal and Antagonistic Regulators of T Follicular Helper Cell Differentiation," *Science* 325(5943):1006-1010 (2009), which is hereby incorporated by reference in its entirety) (Table 3). These data were compared to the list of mRNAs downregulated by 4EGI-1 treatment and 18 mRNAs in both datasets that are regulated in transcription alone were identified, compared to 40 mRNAs in the dataset downregulated by translation alone with eIF4E inhibition (FIG. 4H).

Collectively, these findings suggest that a small group of mRNAs are specifically and acutely dependent on higher levels of eIF4E for TFH cell differentiation and function. Notably, none of the mRNAs upregulated in abundance or translation activity with partial eIF4E inhibition encode established inhibitors of TFH cell differentiation. Thus, mRNAs involved in TFH cell development and function are dependent on higher levels of eIF4E and are downregulated by 4EGI-1 treatment.

TABLE 3

| Gene Symbol | Gene Description |
| --- | --- |
| 1110014N23Rik | protein fat-free homolog |
| 1500011K16Rik | RIKEN cDNA 1500011K16 gene |
| 1500012F01Rik | hypothetical protein LOC68949 |
| 1700001G17Rik | RIKEN cDNA 1700001G17 gene |
| 1700027D21Rik | hypothetical protein LOC76573 |
| 2010300C02Rik | hypothetical protein LOC72097 |
| 2210015D19Rik | RIKEN cDNA 2210015D19 gene |
| 2310011J03Rik | hypothetical protein LOC66374 |
| 2610002J02Rik | RIKEN cDNA 2610002J02 gene |
| 2700049A03Rik | Talpid3 protein |
| 2810002N01Rik | apoptogenic 1 |
| 2810442I21Rik | Egfr long non-coding downstream RNA |
| 4632428N05Rik | platelet receptor Gi24 |
| 4931428F04Rik | hypothetical protein LOC74356 |
| 6330416G13Rik | transmembrane protein C9orf91 homolog |
| 6720456B07Rik | probable protein BRICK1 |
| 8430427H17Rik | hypothetical protein LOC329540 |
| AA415398 | hypothetical protein LOC433752 |
| Acap3 | arf-GAP with coiled-coil, ANK repeat and PH |
| Acot7 | cytosolic acyl coenzyme A thioester hydrolase |
| Adc | antizyme inhibitor 2 |
| Adpgk | ADP-dependent glucokinase precursor |
| Aggf1 | angiogenic factor with G patch and FHA domains |
| Agpat5 | 1-acyl-sn-glycerol-3-phosphate acyltransferase |
| Ahctf1 | protein ELYS |
| Ahdc1 | AT-hook DNA-binding motif-containing protein 1 |
| Ahsa1 | activator of 90 kDa heat shock protein ATPase |
| AI314180 | proteasome-associated protein ECM29 homolog |
| Akna | AT-hook-containing transcription factor |
| Akt1s1 | proline-rich AKT1 substrate 1 |
| Ano8 | anoctamin-8 |
| Anp32a | acidic leucine-rich nuclear phosphoprotein 32 |
| Arhgef1 | rho guanine nucleotide exchange factor 1 |
| Arhgef10 | rho guanine nucleotide exchange factor 10 |
| Arid3b | AT-rich interactive domain-containing protein |
| Arid5a | AT-rich interactive domain-containing protein 5A |
| Arl10 | ADP-ribosylation factor-like protein 10 |
| Arl6ip1 | ADP-ribosylation factor-like protein |
| Asb1 | ankyrin repeat and SOCS box protein 1 |
| Asb2 | ankyrin repeat and SOCS box protein 2 |
| Asf1a | histone chaperone ASF1A |
| Atg9b | autophagy-related protein 9B |
| Atp13a3 | probable cation-transporting ATPase 13A3 |
| Atp5j | ATP synthase-coupling factor 6, mitochondrial |

TABLE 3-continued

Co-Identified Genes

| Gene Symbol | Gene Description |
| --- | --- |
| Atp6v0e | V-type proton ATPase subunit e 1 |
| Atrip | ATR-interacting protein |
| Atxn2 | ataxin-2 |
| AW011738 | expressed sequence AW011738 |
| Axl | tyrosine-protein kinase receptor UFO |
| Azi1 | 5-azacytidine-induced protein 1 |
| B430319G15Rik | RIKEN cDNA B430319G15 gene |
| B4galt1 | beta-1,4-galactosyltransferase 1 |
| B4galt4 | beta-1,4-galactosyltransferase 4 |
| B930059L03Rik | RIKEN cDNA B930059L03 gene |
| Banf1 | barrier-to-autointegration factor |
| Bcl2 | apoptosis regulator Bcl-2 |
| Bcl6 | B-cell lymphoma 6 protein homolog |
| Bcr | breakpoint cluster region protein |
| Bdh2 | 3-hydroxybutyrate dehydrogenase type 2 |
| Btbd7 | BTB/POZ domain-containing protein 7 |
| Cacnb3 | voltage-dependent L-type calcium channel subunit |
| Camk2d | calcium/calmodulin-dependent protein kinase type |
| Camsap1l1 | calmodulin-regulated spectrin-associated protein |
| Cbx6 | chromobox protein homolog 6 |
| Cbx6-Nptxr | neuronal pentraxin with chromo domain |
| Ccdc102a | coiled-coil domain-containing protein 102A |
| Ccdc48 | coiled-coil domain-containing protein 48 |
| Ccno | cyclin-O |
| Cdc42se1 | CDC42 small effector protein 1 |
| Cdh23 | cadherin-23 precursor |
| Cdhr3 | cadherin-related family member 3 precursor |
| Cdk2ap2 | cyclin-dependent kinase 2-associated protein 2 |
| Cdkal1 | CDK5 regulatory subunit-associated protein |
| Cebpg | CCAAT/enhancer-binding protein gamma |
| Chchd10 | coiled-coil-helix-coiled-coil-helix |
| Clcf1 | cardiotrophin-like cytokine factor 1 precursor |
| Clic4 | chloride intracellular channel protein 4 |
| Clptm1l | cleft lip and palate transmembrane protein |
| Cnst | consortin |
| Comt1 | catechol O-methyltransferase |
| Cops8 | COP9 signalosome complex subunit 8 |
| Coro1a | coronin-1A |
| Coro1b | coronin-1B |
| Coro2b | coronin-2B |
| Cyb5 | cytochrome b5 |
| Cyth1 | cytohesin-1 |
| Cyth4 | cytohesin-4 |
| Cytip | cytohesin-interacting protein |
| D030028A08Rik | RIKEN cDNA D030028A08 gene |
| D430019H16Rik | RIKEN cDNA D430019H16 gene |
| D8Ertd738e | leydig cell tumor 10 kDa protein homolog |
| D930015E06Rik | transmembrane protein 131-like precursor |
| Dap | death-associated protein 1 |
| Dck | deoxycytidine kinase |
| Dcp2 | mRNA-decapping enzyme 2 |
| Ddx39 | ATP-dependent RNA helicase DDX39 |
| Ddx6 | probable ATP-dependent RNA helicase DDX6 |
| Dedd2 | DNA-binding death effector domain-containing |
| Dem1 | defects in morphology protein 1 homolog |
| Dhx30 | putative ATP-dependent RNA helicase DHX30 |
| Dot1l | histone-lysine N-methyltransferase, H3 lysine-79 |
| Dthd1 | death domain containing 1 |
| Dus2l | tRNA-dihydrouridine synthase 2-like |
| Dusp10 | dual specificity protein phosphatase 10 |
| Dym | dymeclin |
| Dyrk1a | dual specificity |
| Dyrk2 | dual specificity |
| Dzip1 | zinc finger protein DZIP1 |
| Eef1a1 | elongation factor 1-alpha 1 |
| Eef2 | elongation factor 2 |
| Eef2k | eukaryotic elongation factor 2 kinase |
| Egln3 | egl nine homolog 3 |
| Eif1ad | probable RNA-binding protein EIF1AD |
| Elf4 | ETS-related transcription factor Elf-4 |
| Espn | espin |
| Ets1 | protein C-ets-1 |
| Evl | ena/VASP-like protein |
| Exoc3l | exocyst complex component 3-like protein |
| Ext2 | exostosin-2 |
| F13a1 | coagulation factor XIII A chain precursor |
| F2r | proteinase-activated receptor 1 precursor |
| F3 | tissue factor precursor |
| Fam129a | protein Niban |
| Fam65c | hypothetical protein LOC69553 |
| Fam69a | family with sequence similarity 69, member A |
| Fam72a | hypothetical protein LOC108900 |
| Fancm | Fanconi anemia group M protein homolog |
| Farp1 | FERMRhoGEF (Arhgef) and pleckstrin domain |
| Fastkd1 | FAST kinase domain-containing protein 1 |
| Fbxo48 | F-box only protein 48 |
| Fchsd2 | FCH and double SH3 domains protein 2 |
| Fhad1 | forkhead-associated domain-containing protein 1 |
| Fkbp3 | peptidyl-prolyl cis-trans isomerase FKBP3 |
| Flnb | filamin-B |

TABLE 3-continued

Co-Identified Genes

| Gene Symbol | Gene Description |
|---|---|
| Fnbp1 | formin-binding protein 1 |
| Fndc7 | fibronectin type III domain-containing protein 7 |
| Fntb | protein farnesyltransferase subunit beta |
| Fosl2 | fos-related antigen 2 |
| Foxj3 | forkhead box protein J3 |
| Gabpa | GA-binding protein alpha chain |
| Gcat | 2-amino-3-ketobutyrate coenzyme A ligase, |
| Gga1 | ADP-ribosylation factor-binding protein GGA1 |
| Gipc1 | PDZ domain-containing protein GIPC1 |
| Gm672 | CBP80/20-dependent translation initiation |
| Gna13 | guanine nucleotide-binding protein subunit |
| Gnb1 | guanine nucleotide-binding protein |
| Gng7 | guanine nucleotide-binding protein |
| Gnl3 | guanine nucleotide-binding protein-like 3 long |
| Gpr176 | probable G-protein coupled receptor 176 |
| Gpr18 | N-arachidonyl glycine receptor |
| Gramd1a | GRAM domain-containing protein 1A |
| Gstt4 | glutathione S-transferase theta-4 |
| Gtpbp3 | tRNA modification GTPase GTPBP3, mitochondrial |
| H1f0 | histone H1.0 |
| Hdgf | hepatoma-derived growth factor |
| Hdhd2 | haloacid dehalogenase-like hydrolase |
| Hivep2 | transcription factor HIVEP2 |
| Hk2 | hexokinase-2 |
| Hmgb1 | high mobility group protein B1 |
| Hmha1 | minor histocompatibility protein HA-1 |
| Hnrnpd | heterogeneous nuclear ribonucleoprotein D0 |
| Hnrnpf | heterogeneous nuclear ribonucleoprotein F |
| Hook2 | protein Hook homolog 2 |
| Hpcal4 | hippocalcin-like protein 4 |
| Hras1 | GTPase HRas |
| Htra3 | probable serine protease HTRA3 |
| Id2 | DNA-binding protein inhibitor ID-2 |
| Il2rb | interleukin-2 receptor subunit beta precursor |
| Il7r | interleukin-7 receptor subunit alpha precursor |
| Ino80c | INO80 complex subunit C |
| Insr | insulin receptor precursor |
| Irak1 | interleukin-1 receptor-associated kinase 1 |
| Irf2bp2 | interferon regulatory factor 2 binding protein |
| Irf4 | interferon regulatory factor 4 |
| Isg15 | ubiquitin-like protein ISG15 precursor |
| Itgb4 | integrin beta-4 |
| Itpkb | inositol-trisphosphate 3-kinase B |
| Itpr2 | inositol 1,4,5-trisphosphate receptor type 2 |
| Kank3 | KN motif and ankyrin repeat domain-containing |
| Kcna7 | potassium voltage-gated channel subfamily A |
| Kcnab2 | voltage-gated potassium channel subunit beta-2 |
| Kcnn4 | intermediate conductance calcium-activated |
| Kctd7 | BTB/POZ domain-containing protein KCTD7 |
| Kdm6b | lysine-specific demethylase 6B |
| Keap1 | kelch-like ECH-associated protein 1 |
| Kif21b | kinesin-like protein KIF21B |
| Klf9 | Krueppel-like factor 9 |
| Klhl25 | ectoderm-neural cortex protein 2 |
| Klre1 | killer cell lectin-like receptor family E member |
| Lace1 | lactation elevated protein 1 |
| Lag3 | lymphocyte activation gene 3 protein precursor |
| Ldlrap1 | low density lipoprotein receptor adapter protein |
| Letmd1 | LETM1 domain-containing protein 1 |
| Lif | leukemia inhibitory factor |
| Lpin2 | phosphatidate phosphatase LPIN2 |
| Lrig1 | leucine-rich repeats and immunoglobulin-like |
| Lrp6 | low-density lipoprotein receptor-related protein |
| Lrrc56 | leucine-rich repeat-containing protein 56 |
| Lrrc6 | leucine-rich repeat-containing protein 6 |
| Lsm12 | protein LSM12 homolog |
| Lsp1 | lymphocyte-specific protein 1 |
| Ly9 | T-lymphocyte surface antigen Ly-9 precursor |
| Manba | beta-mannosidase precursor |
| Map3k1 | mitogen-activated protein kinase kinase kinase |
| Map3k12 | mitogen-activated protein kinase kinase kinase |
| Map4k1 | mitogen-activated protein kinase kinase kinase |
| Mapk1ip1l | MAPK-interacting and spindle-stabilizing |
| Mapk8ip3 | C-Jun-amino-terminal kinase-interacting protein |
| Mapkapk2 | MAP kinase-activated protein kinase 2 |
| March7 | E3 ubiquitin-protein ligase MARCH7 |
| Mbd2 | methyl-CpG-binding domain protein 2 |
| Mbp | Golli-Mbp |
| Mcm9 | DNA replication licensing factor MCM9 |
| Mef2d | myocyte-specific enhancer factor 2D |
| Memo1 | protein MEMO1 |
| Mepce | 7SK snRNA methylphosphate capping enzyme |
| Mex3b | RNA-binding protein MEX3B |
| Mfsd10 | major facilitator superfamily domain-containing |
| Mgea5 | bifunctional protein NCOAT |
| Mgll | monoglyceride lipase |
| Mll1 | histone-lysine N-methyltransferase MLL |
| Mllt11 | protein AF1q |

TABLE 3-continued

Co-Identified Genes

| Gene Symbol | Gene Description |
|---|---|
| Mllt6 | myeloid/lymphoid or mixed lineage-leukemia |
| Morf4l1 | mortality factor 4-like protein 1 |
| Msh2 | DNA mismatch repair protein Msh2 |
| Msi2 | RNA-binding protein Musashi homolog 2 |
| Mta3 | metastasis-associated protein MTA3 |
| Mtap6 | microtubule-associated protein 6 |
| Mterfd1 | mTERF domain-containing protein 1, mitochondrial |
| Mxd4 | max dimerization protein 4 |
| Mxi1 | max-interacting protein 1 |
| Myh9 | myosin-9 |
| Myo1g | myosin-Ig |
| N4bp2 | Nedd4 binding protein 2 |
| Napepld | N-acyl-phosphatidylethanolamine-hydrolyzing |
| Narfl | cytosolic Fe—S cluster assembly factor NARFL |
| Nbeal2 | neurobeachin-like protein 2 |
| Ndufa7 | NADH dehydrogenase [ubiquinone] 1 alpha |
| Nedd4l | E3 ubiquitin-protein ligase NEDD4-like |
| Nfatc1 | nuclear factor of activated T-cells, cytoplasmic |
| Nfkb1 | nuclear factor NF-kappa-B p105 subunit |
| Ngly1 | peptide-N(4)-(N-acetyl-beta- |
| Nphp4 | nephrocystin-4 |
| Npm1 | nucleophosmin |
| Nsmce2 | E3 SUMO-protein ligase NSE2 |
| Nuak1 | NUAK family SNF1-like kinase 1 |
| Nusap1 | nucleolar and spindle-associated protein 1 |
| Oip5 | protein Mis18-beta |
| Orai3 | protein orai-3 |
| ORF61 | membralin |
| Osm | oncostatin-M precursor |
| Oxsm | 3-oxoacyl-[acyl-carrier-protein] synthase, |
| P4htm | transmembrane prolyl 4-hydroxylase |
| Panx1 | pannexin-1 |
| Park7 | protein DJ-1 |
| Parp10 | poly (ADP-ribose) polymerase family, member 10 |
| Pbrm1 | protein polybromo-1 |
| Pde4b | phosphodiesterase 4B |
| Pdlim4 | PDZ and LIM domain protein 4 |
| Pds5a | sister chromatid cohesion protein PDS5 homolog |
| Peg13 | paternally expressed 13 |
| Pfdn2 | prefoldin subunit 2 |
| Pgm2 | phosphoglucomutase-1 |
| Pgs1 | CDP-diacylglycerol--glycerol-3-phosphate |
| Pias4 | E3 SUMO-protein ligase PIAS4 |
| Pigz | GPI mannosyltransferase 4 |
| Pik3cg | phosphatidylinositol-4,5-bisphosphate 3-kinase |
| Pip5k1c | phosphatidylinositol-4-phosphate 5-kinase type-1 |
| Pitpnc1 | cytoplasmic phosphatidylinositol transfer |
| Pitpnm1 | membrane-associated phosphatidylinositol |
| Pla2g12a | group XIIA secretory phospholipase A2 |
| Plcl2 | inactive phospholipase C-like protein 2 |
| Plec | plectin |
| Plod2 | procollagen-lysine,2-oxoglutarate 5-dioxygenase |
| Pmpca | mitochondrial-processing peptidase subunit alpha |
| Pnkp | bifunctional polynucleotide phosphatase/kinase |
| Pnpo | pyridoxine-5'-phosphate oxidase |
| Pold4 | DNA polymerase delta subunit 4 |
| Polr3e | DNA-directed RNA polymerase III subunit RPC5 |
| Ppp2r5c | serine/threonine-protein phosphatase 2A 56 kDa |
| Pqbp1 | polyglutamine-binding protein 1 |
| Prim2 | DNA primase large subunit |
| Prkar1a | cAMP-dependent protein kinase type I-alpha |
| Prmt6 | protein arginine N-methyltransferase 6 |
| Prr5l | proline-rich protein 5-like |
| Ptdss1 | phosphatidylserine synthase 1 |
| Ptk2b | protein-tyrosine kinase 2-beta |
| Ptpn1 | tyrosine-protein phosphatase non-receptor type |
| Ptpn5 | tyrosine-protein phosphatase non-receptor type |
| Ptprcap | protein tyrosine phosphatase receptor type |
| Ptprj | receptor-type tyrosine-protein phosphatase eta |
| Ptprs | receptor-type tyrosine-protein phosphatase S |
| Purb | transcriptional activator protein Pur-beta |
| Pusl1 | tRNA pseudouridine synthase-like 1 |
| Pxk | PX domain-containing protein kinase-like protein |
| Pygm | glycogen phosphorylase, muscle form |
| Qrfp | orexigenic neuropeptide QRFP precursor |
| Rab11fip4 | rab11 family-interacting protein 4 |
| Rabggta | geranylgeranyl transferase type-2 subunit alpha |
| Rala | ras-related protein Ral-A precursor |
| Ralb | ras-related protein Ral-B precursor |
| Ralgapa1 | ral GTPase-activating protein subunit alpha-1 |
| Ralgds | ral guanine nucleotide dissociation stimulator |
| Ramp1 | receptor activity-modifying protein 1 |
| Rasgrp1 | RAS guanyl-releasing protein 1 |
| Rassf2 | ras association domain-containing protein 2 |
| Rbbp8 | retinoblastoma-binding protein 8 |
| Rbm14 | RNA-binding protein 14 |
| Rbm47 | RNA-binding protein 47 |
| Relt | tumor necrosis factor receptor superfamily |
| Rhoh | rho-related GTP-binding protein RhoH precursor |
| Ripk2 | receptor-interacting serine/threonine-protein |
| Rock2 | rho-associated protein kinase 2 |
| Ropn1l | ropporin-1-like protein |
| rp9 | retinitis pigmentosa 9 protein homolog |
| Rpl24 | 60S ribosomal protein L24 |
| Rpl32 | 60S ribosomal protein L32 |
| Rps6ka1 | ribosomal protein S6 kinase alpha-1 |

TABLE 3-continued

Co-Identified Genes

| Gene Symbol | Gene Description |
|---|---|
| Rps6ka3 | ribosomal protein S6 kinase alpha-3 |
| Rptor | regulatory-associated protein of mTOR |
| Runx3 | runt-related transcription factor 3 |
| Saps2 | serine/threonine-protein phosphatase 6 |
| Satb1 | DNA-binding protein SATB1 |
| Sdccag3 | serologically defined colon cancer antigen 3 |
| Sel11 | protein sel-1 homolog 1 |
| Selplg | P-selectin glycoprotein ligand 1 |
| Sema4d | semaphorin-4D precursor |
| Sertad1 | SERTA domain-containing protein 1 |
| Setd7 | histone-lysine N-methyltransferase SETD7 |
| Setd8 | histone-lysine N-methyltransferase SETD8 |
| Sf3b4 | splicing factor 3B subunit 4 |
| Sf3b5 | splicing factor 3B subunit 5 |
| Sfrs13a | serine/arginine-rich splicing factor 10 |
| Sft2d2 | vesicle transport protein SFT2B |
| Sfxn1 | sideroflexin-1 |
| Sgip1 | SH3-containing GRB2-like protein 3-interacting |
| Sgsh | N-sulfoglucosamine sulfohydrolase |
| Sh3gl1 | endophilin-A2 |
| Sh3pxd2a | SH3 and PX domain-containing protein 2A |
| Siah2 | E3 ubiquitin-protein ligase SIAH2 |
| Ski | ski oncogene |
| Slc26a11 | sodium-independent sulfate anion transporter |
| Slc38a1 | sodium-coupled neutral amino acid transporter 1 |
| Slc41a2 | solute carrier family 41 member 2 |
| Slc44a3 | choline transporter-like protein 3 |
| Slco3a1 | solute carrier organic anion transporter family |
| Smad7 | mothers against decapentaplegic homolog 7 |
| Snapc4 | snRNA-activating protein complex subunit 4 |
| Snora7a | small nucleolar RNA, H/ACA box 7A |
| Snord19 | small nucleolar RNA, C/D box 19 |
| Snord37 | small nucleolar RNA, C/D box 37 [Mus musculus] |
| Snrnp70 | U1 small nuclear ribonucleoprotein 70 kDa |
| Sntb1 | beta-1-syntrophin |
| Snx18 | sorting nexin-18 |
| Socs2 | suppressor of cytokine signaling 2 |
| Sp3 | transcription factor Sp3 |
| Spsb1 | SPRY domain-containing SOCS box protein 1 |
| Srgap2 | SLIT-ROBO Rho GTPase-activating protein 2 |
| Ssbp3 | single-stranded DNA-binding protein 3 |
| St8sia1 | alpha-N-acetylneuraminide |
| Stat3 | signal transducer and activator of transcription |
| Stat5a | signal transducer and activator of transcription |
| Susd3 | sushi domain-containing protein 3 |
| Svil | supervillin |
| Sytl1 | synaptotagmin-like protein 1 |
| Tacc3 | transforming acidic coiled-coil-containing |
| Taf5l | TAF5-like RNA polymerase II p300/CBP-associated |
| Taok3 | serine/threonine-protein kinase TAO3 |
| Tapt1 | transmembrane anterior posterior transformation |
| Tarbp2 | RISC-loading complex subunit TARBP2 |
| Tbc1d10c | carabin |
| Tcf4 | transcription factor 4 |
| Tcf7 | transcription factor 7 |
| Tcfap4 | transcription factor AP-4 |
| Tcfe3 | transcription factor E3 |
| Tead3 | transcriptional enhancer factor TEF-5 |
| Tecpr1 | tectonin beta-propeller repeat-containing |
| Tfb2m | dimethyladenosine transferase 2, mitochondrial |
| Timm17b | mitochondrial import inner membrane translocase |
| Timm9 | mitochondrial import inner membrane translocase |
| Tle4 | transducin-like enhancer protein 4 |
| Tm7sf2 | delta(14)-sterol reductase |
| Tmc6 | transmembrane channel-like protein 6 |
| Tmem129 | transmembrane protein 129 precursor |
| Tmem143 | transmembrane protein 143 |
| Tnfaip8l2 | tumor necrosis factor alpha-induced protein |
| Tnfrsf18 | tumor necrosis factor receptor superfamily |
| Tnfrsf1b | tumor necrosis factor receptor superfamily |
| Tnfrsf8 | tumor necrosis factor receptor superfamily |
| Tnrc6b | trinucleotide repeat-containing gene 6B protein |
| Tox | thymocyte selection-associated high mobility |
| Tprgl | tumor protein p63-regulated gene 1-like protein |
| Tpst2 | protein-tyrosine sulfotransferase 2 |
| Trabd | traB domain-containing protein |
| Traf3 | TNF receptor-associated factor 3 |
| Trappc9 | trafficking protein particle complex subunit 9 |
| Trerf1 | transcriptional-regulating factor 1 |
| Tsfm | elongation factor Ts, mitochondrial precursor |
| Tuba1b | tubulin alpha-1B chain |
| Twf2 | twinfilin-2 |
| Txk | tyrosine-protein kinase TXK |
| Txnip | thioredoxin-interacting protein |
| Ubac2 | ubiquitin-associated domain-containing protein 2 |
| Ubash3b | ubiquitin-associated and SH3 domain-containing |
| Unc13a | protein unc-13 homolog A |
| Unc45a | protein unc-45 homolog A |
| Urb2 | unhealthy ribosome biogenesis protein 2 homolog |
| Urgcp | up-regulator of cell proliferation |
| Usp3 | ubiquitin carboxyl-terminal hydrolase 3 |
| Vegfa | vascular endothelial growth factor A |
| Vipar | VPS33B-interacting protein |
| Wdr6 | WD repeat-containing protein 6 |
| Wdtc1 | WD and tetratricopeptide repeats protein 1 |

TABLE 3-continued

Co-Identified Genes

| Gene Symbol | Gene Description |
|---|---|
| Wnt11 | protein Wnt-11 precursor |
| Ywhae | 14-3-3 protein epsilon |
| Zbtb7b | zinc finger and BTB domain-containing protein |
| Zcwpw1 | zinc finger CW-type PWWP domain protein 1 |
| Zdhhc18 | palmitoyltransferase ZDHHC18 |
| Zfp286 | zinc finger protein 286 |
| Zfp296 | zinc finger protein 296 |
| Zfp746 | zinc finger protein 746 |
| Zfr2 | zinc finger RNA binding protein 2 |
| Zhx2 | zinc fingers and homeoboxes protein 2 |
| Znfx1 | NFX1-type zinc finger-containing protein 1 |

Example 4—BCL6-Dependent TFH Cell Differentiation and Maintenance is Blocked by Partial eIF4E Inhibition The dependence on higher levels of eIF4E for expression of receptors, transcription factors, and cytokines identified by genome-wide analysis were tested on TFH cell differentiation and maintenance. Animals were immunized with OVA/alum, with and without partial inhibition of eIF4E function by 4EGI-1 (FIG. 5A). In agreement with the genome-wide transcriptomic/translatomic analysis, 4EGI-1 downregulation of eIF4E function did not affect CD4+ T cell activation (CD44$^{high}$), cell division, or levels of expression of ICOS (FIGS. 5B-5D). However, it did reduce by more than half the expression of PD-1, intranuclear BCL6, and surface CXCR5 on splenic CD4+ T cells (FIGS. 5E-5G). Thus, moderately reduced eIF4E activity specifically impairs T cell differentiation to TFH cells without impacting CD4+ T cell activation.

Figures 5I, 5J, 5K, 5L, 5M, 5N, 5O:
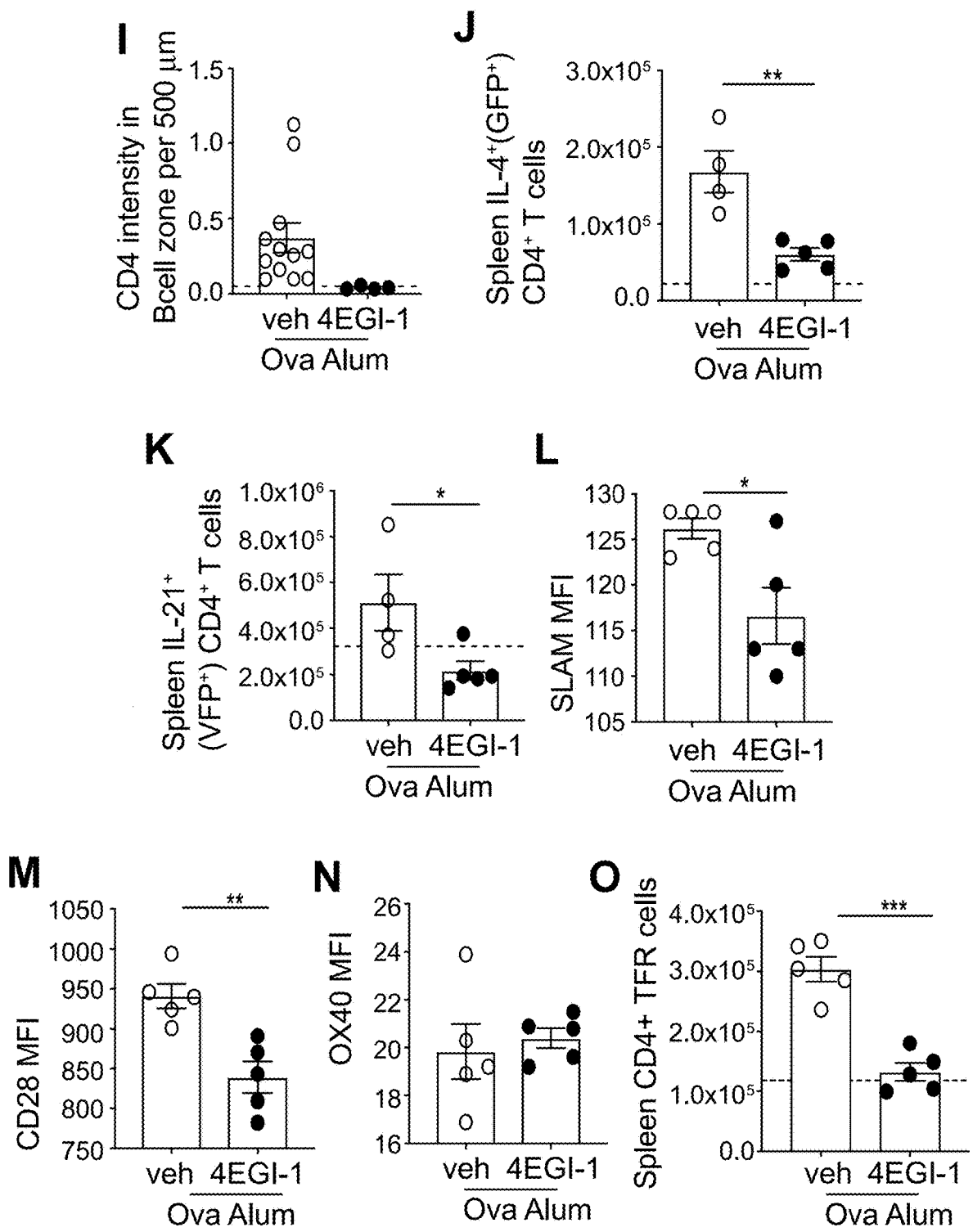

CXCR5 is central to CD4+ T cell migration into the B cell zone. Selective translation of CXCR5 mRNA suggests a foundational mechanism for control by levels of eIF4E in TFH cell development and function. Indeed, 4EGI-1 administration almost abolished infiltration of CD4+ T cells (green) in B cell zones (red, outlined) (FIGS. 5H-5I). Once within the B cell zone, TFH cells produce IL-4 and IL-21, and express co-receptors for engagement of GC B cells. Therefore, cytokine reporter mice were utilized to assess the sensitivity to eIF4E inhibition on in vivo production of endogenous IL-4 (GFP+) and IL-21 (VFP+). 4EGI-1 decreased by 2.5-fold the total number of CD4+ T cells producing IL-4 or IL-21 cytokines in the spleen following OVA-Alum immunization (FIGS. 3J-3K). Next, expression of proteins required for engagement of GC B cells within follicles and continued lineage commitment of TFH cells was further investigated. CD4+ T cell expression of SLAM and CD28 was decreased by half following 4EGI-1 treatment, but expression of OX40 was not affected, which is consistent with the genome-wide studies (FIGS. 5L-5M).

The requirement for higher levels of eIF4E activity on T follicular regulatory (TFR) cell development was also investigated. While TFR cells, like TFH cells, are reliant on CXCR5, BCL6, and CD28 for differentiation, if for some reason their levels were increased by eIF4E inhibition that could account for impaired TFH differentiation (Miles & Connick, "Control of the Germinal Center by Follicular Regulatory T Cells During Infection," Front. Immunol. 9:2704 (2018), which is hereby incorporated by reference in its entirety) rather than TFH cell intrinsic inhibition. However, similar to TFH cells, TFR cells were reduced 3-fold by 4EGI-1 downregulation of eIF4E activity, which was measured at day 14, the peak of the TFR response (FIG. 5M). Thus, the expression and translation of mRNAs required for expression of proteins that program TFH cell differentiation (CD28 and BCL6), migration (CXCR5), function (IL-4 and IL-21), and maintenance (SLAM, CD28) are all strongly dependent on high levels of eIF4E activity and acutely sensitive to its partial inhibition.

Figures 7A, 7B, 7C, 7D, 7E, 7F, 7G, 7H:
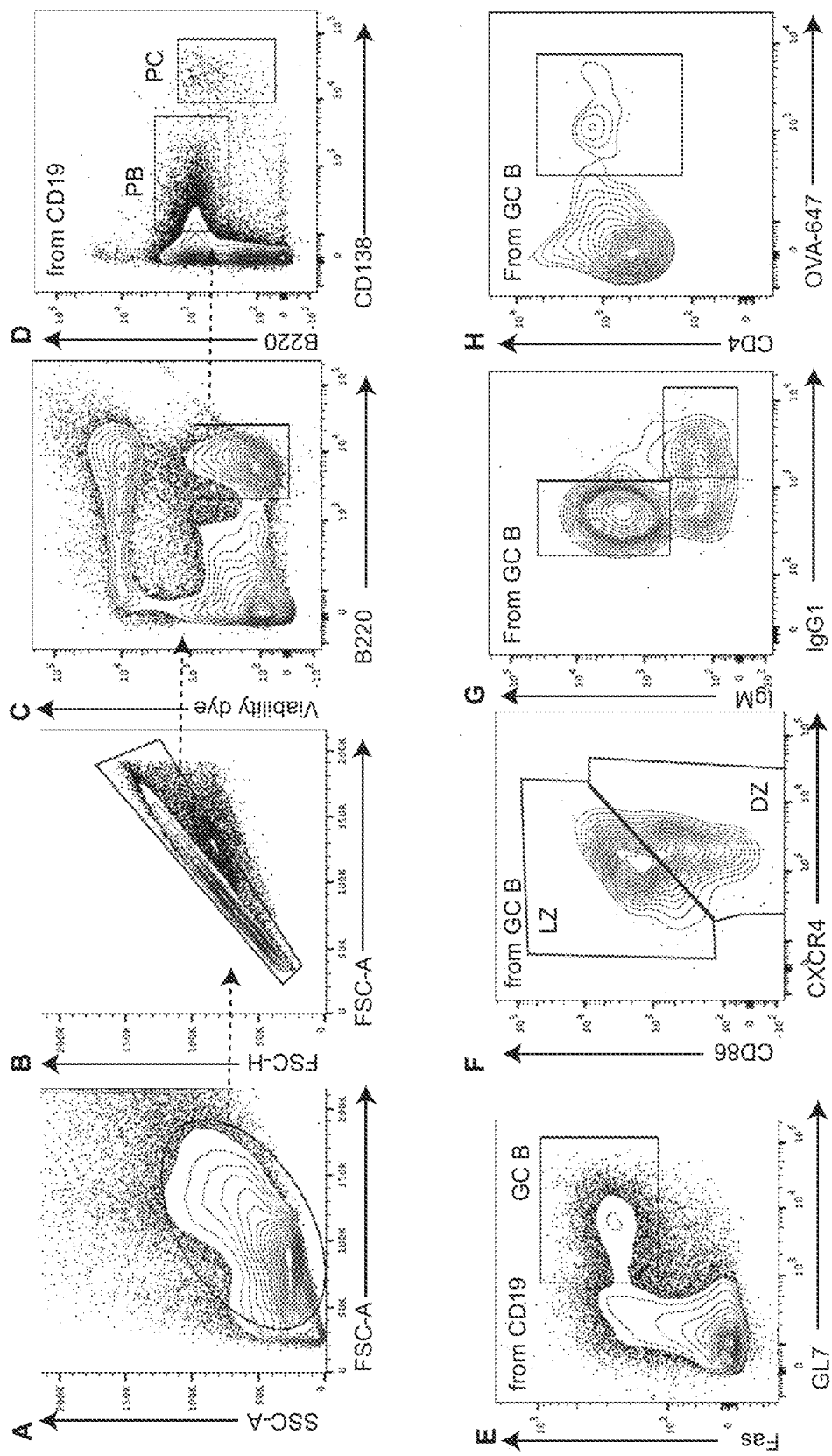
FIGS. 7A-7J show the identification and quantification of GC B cell subsets from animals treated with 4EGI-1.
Figures 7I, 7J:
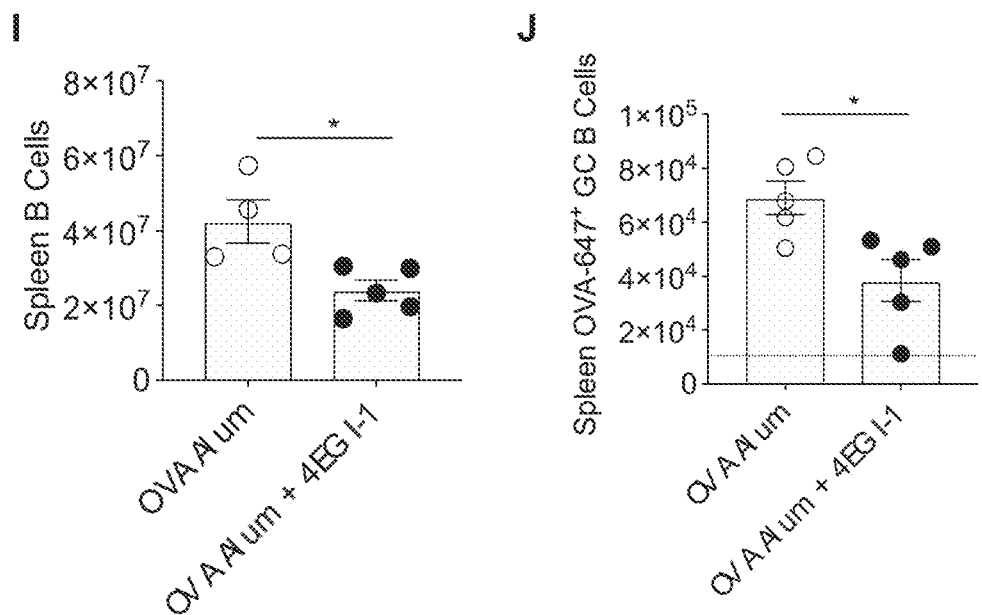
Figures 8A, 8B, 8C, 8D:
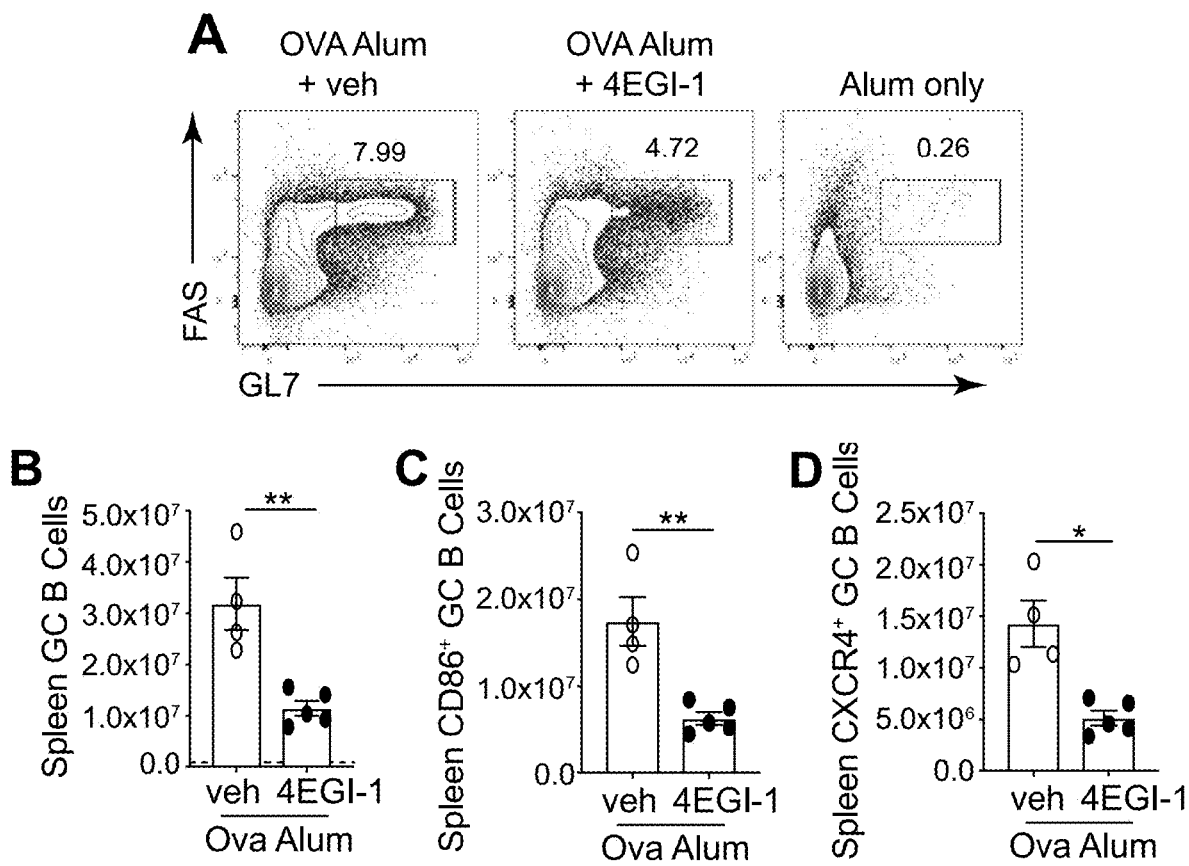
FIGS. 8A-8I show that downregulation of eIF4E activity inhibits GC B cell development and plasma cell formation.
Figures 8E, 8F, 8G, 8H, 8I:
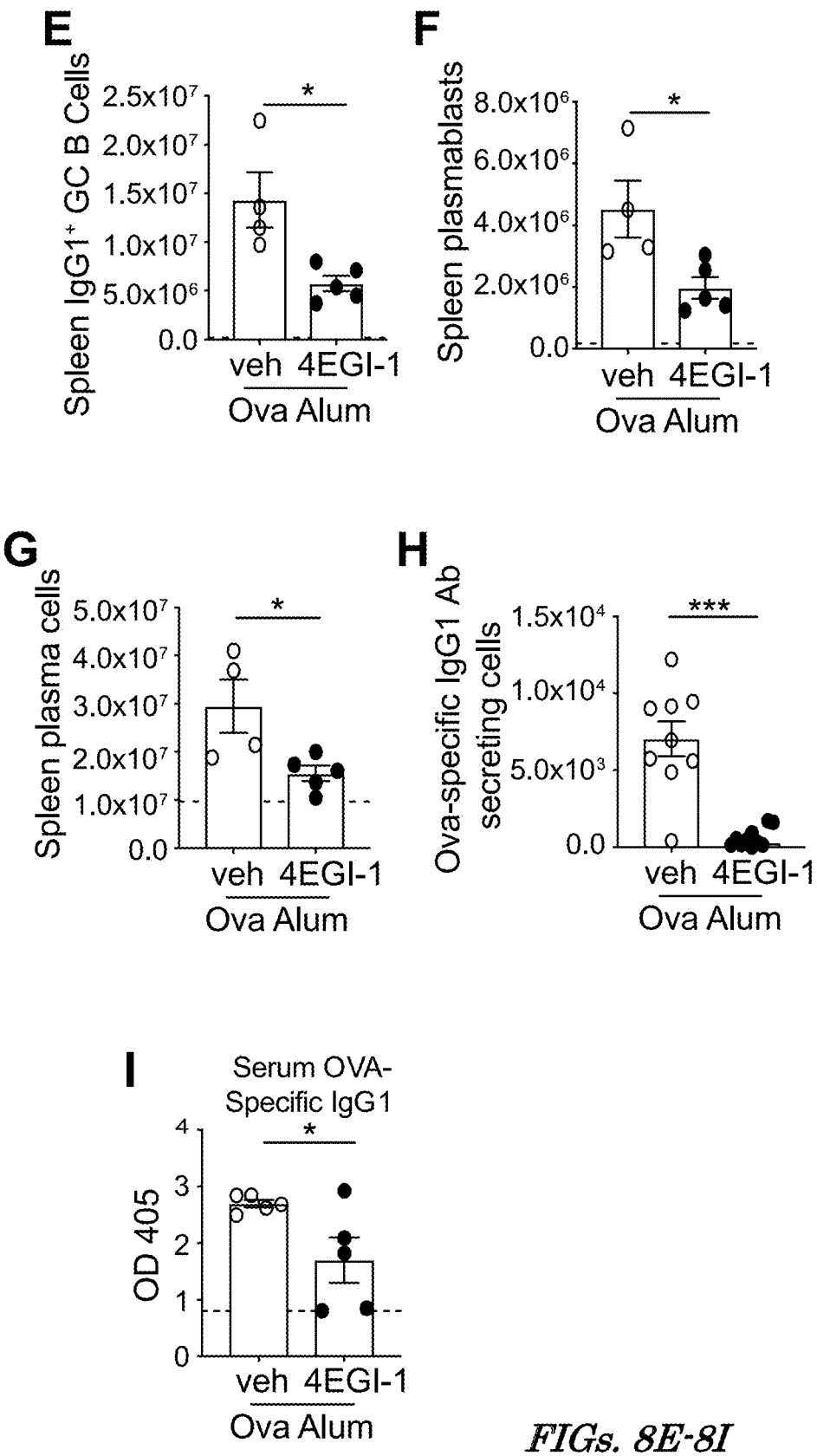
Figures 9A, 9B, 9C, 9D:
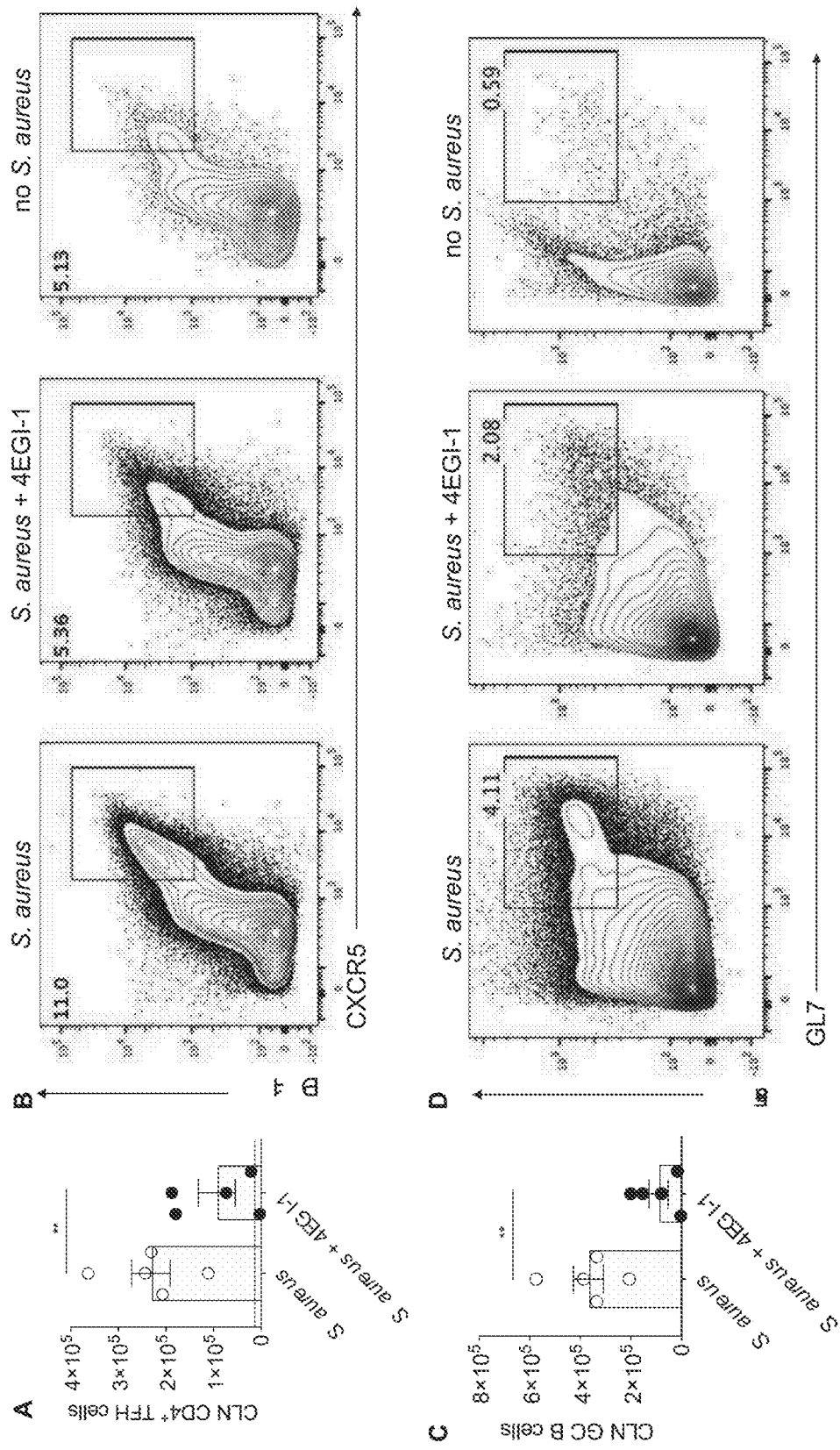
FIGS. 9A-9J show that downregulation of eIF4E function impairs TFH cell and GC B cell development in *S. aureus*-infected or *A. fumigatus*-sensitized mice.
Figure 9E:
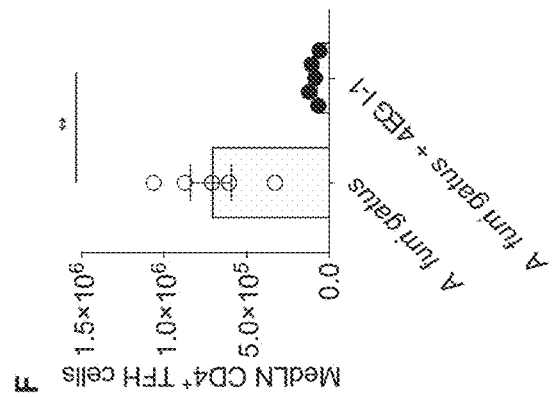
Figure 9F:
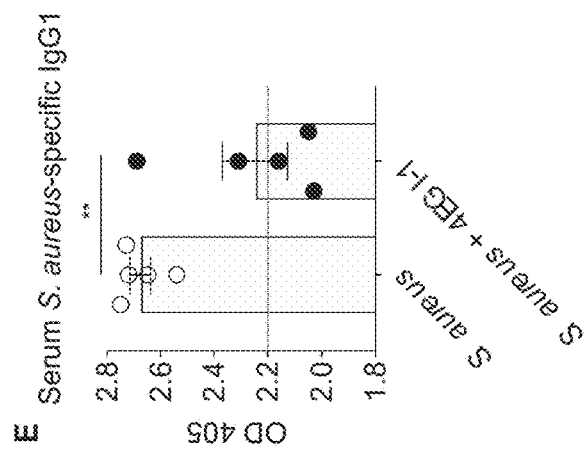
Figure 9G:
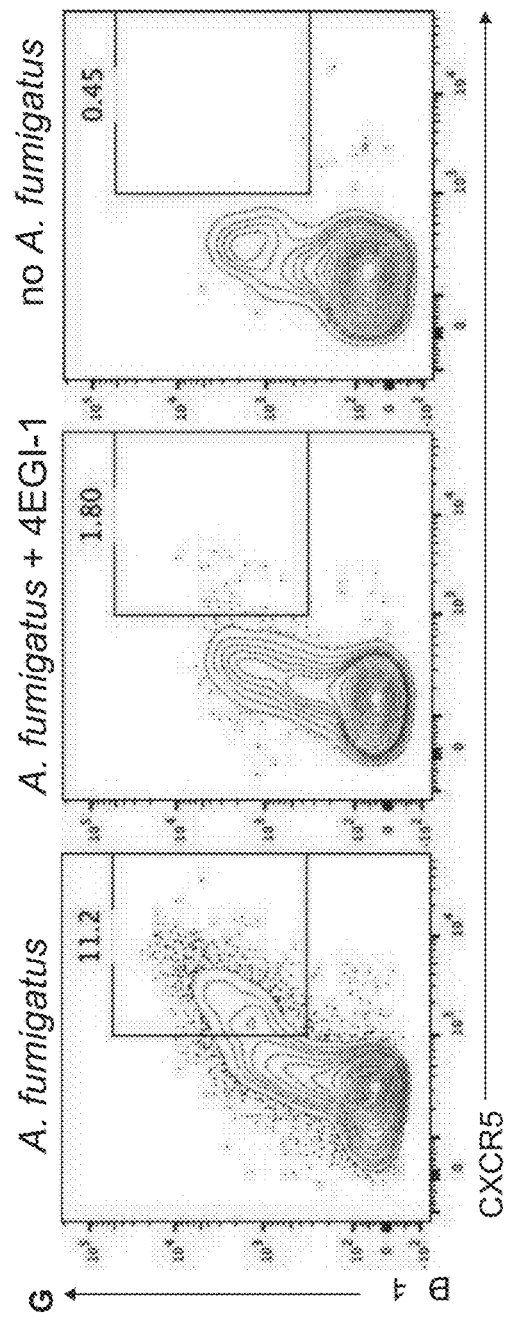
Figure 9H:
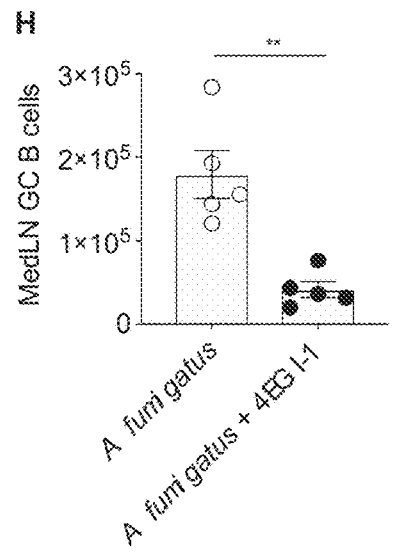
Figure 9I:
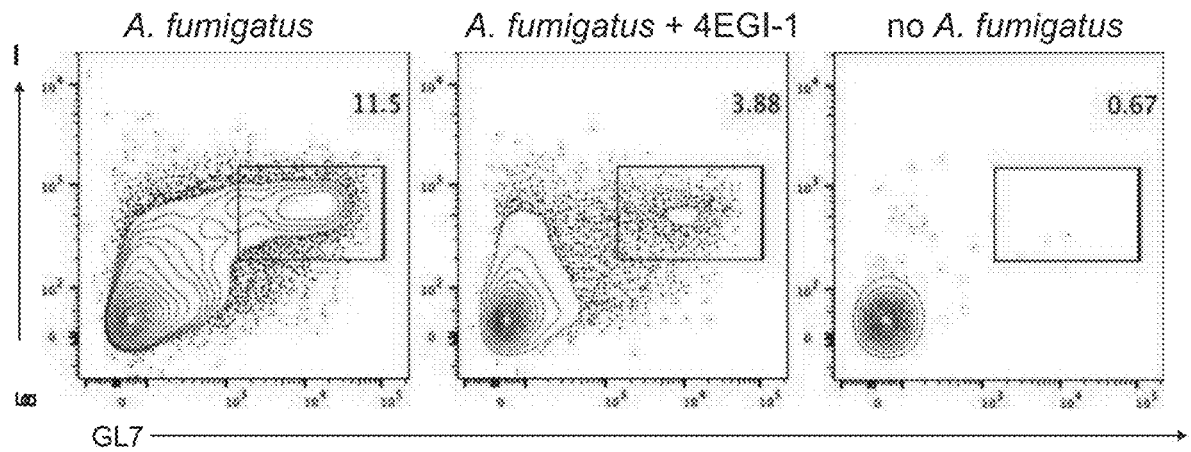
Figure 9J:
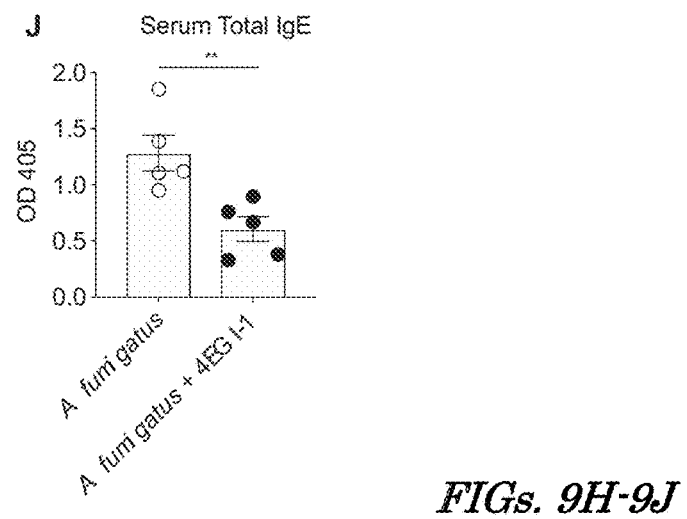

Example 5—Downregulation of eIF4E Activity Selectively Inhibits GC B Cell Development and Plasma Cell Formation CXCR5 is essential for TFH development because it mediates CD4+ T cell migration into the follicles (Webb et al., "Signals that Drive T Follicular Helper Cell Formation," Immunology 152:185-194 (2017), which is hereby incorporated by reference in its entirety). TFH cell differentiation and maintenance in the GC is also dependent on expression of co-receptors for engagement of GC B cells (Webb et al., "Signals that Drive T Follicular Helper Cell Formation," Immunology 152:185-194 (2017), which is hereby incorporated by reference in its entirety). Therefore, the effect of eIF4E downregulation on the splenic B cell compartment following OVA/Alum vaccination was investigated by quantifying OVA/alum induced B cell subsets, as well as GC cell light and dark zones (FIGS. 7A-7H). Reduced eIF4E activity decreased by 3-fold the number of total GC B cells, including those in the CD86+ light zone (LZ), CXCR4+ dark zone (DZ), and GC B cells that are class switched IgG1+ or OVA-specific (FIGS. 7I-7J; FIGS. 8A-8E). Additionally, the number of total plasmablasts and plasma cells were reduced 2-fold, OVA-specific IgG1 antibody secreting cells (ASCs) were almost abolished, and serum OVA-specific IgG1 antibody was reduced by half (FIGS. 8F-8I). Thus, moderate inhibition of eIF4E activity significantly impairs development of GC B cells and maturation to antigen-specific plasma cells following immunization. Moreover, reduced eIF4E activity during S. aureus infection (FIG. 2A) or allergic sensitization with A. fumigatus (FIG. 2F), also strongly reduced formation of both TFH cells and GC B cells in draining lymph nodes, as well as secretion of class-switched immunoglobulins (FIG. 9). Collectively similar inhibition of TFH cell development, function, and GC B cell levels by reduced eIF4E activity was observed in the context of three very different inflammatory states.

Figures 10A, 10B, 10C, 10D, 10E, 10F, 10G:
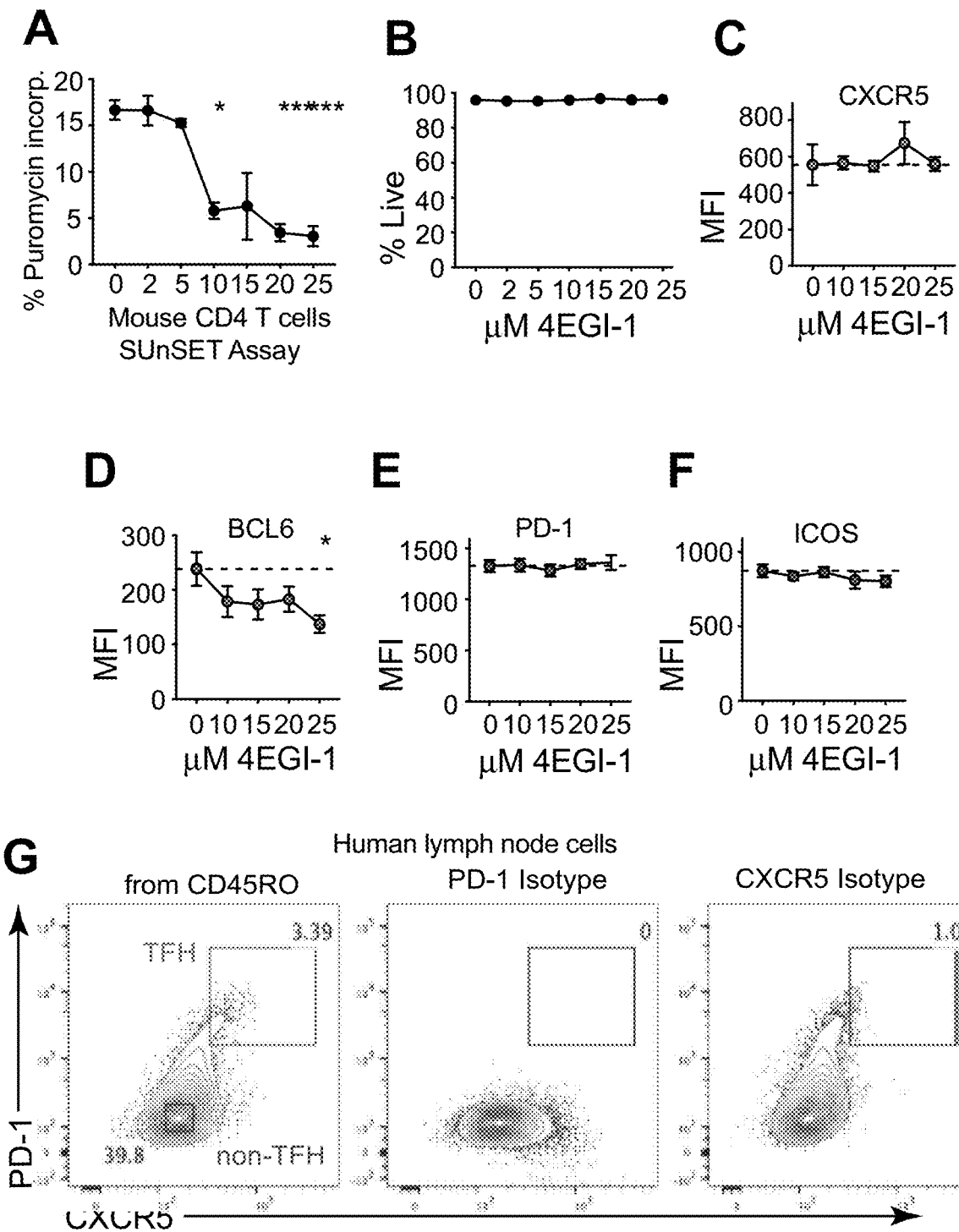
Figure 10H:
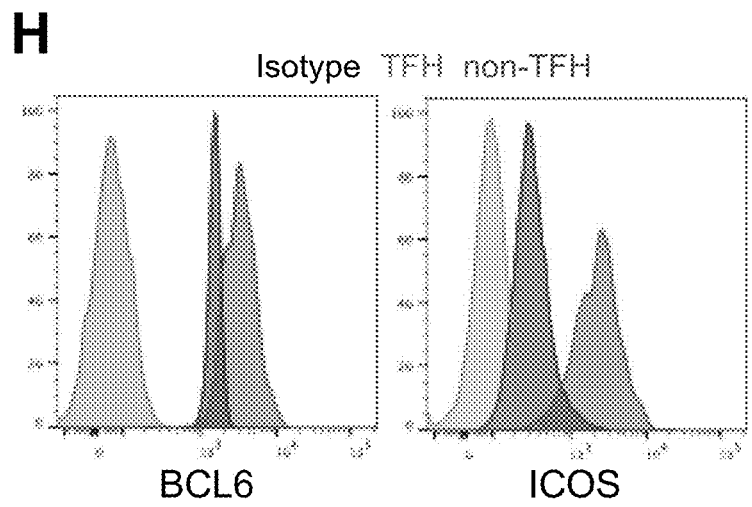
Figure 10I:
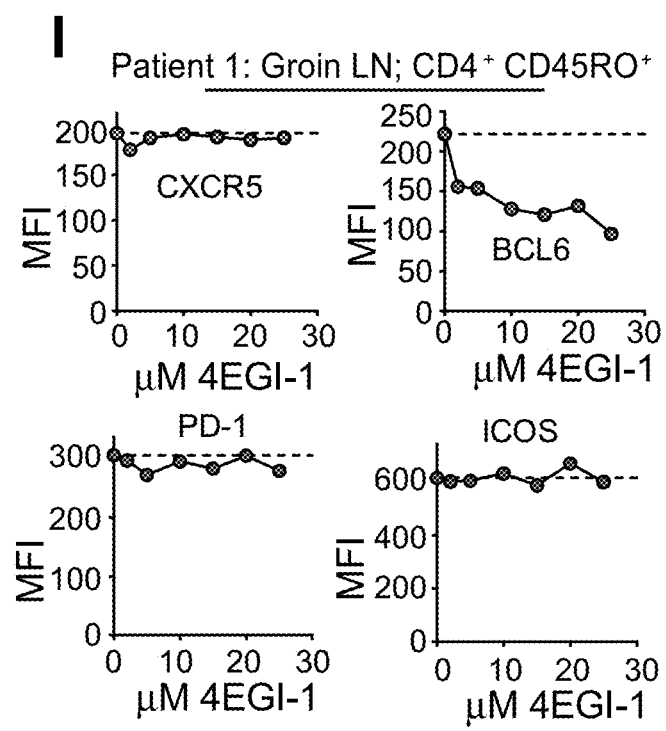
In FIGS. 10I-10K human lymph node cells from Patient 1 (FIG. 10I), Patient 2 (FIG. 10J), and Patient 3 (FIG. 10K) were incubated with 0-30 µM 4EGI-1 overnight, and CD4+ CD45RO+ T cells were quantified for expression of surface CXCR5, ICOS, PD-1, and intranuclear BCL6 from 3 independent human lymph nodes.
Figure 10J:
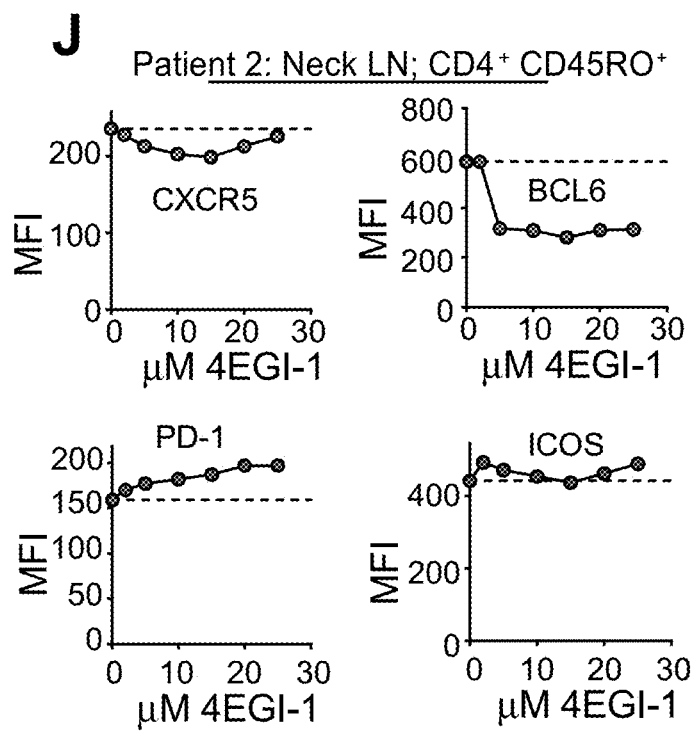
Figure 10K:
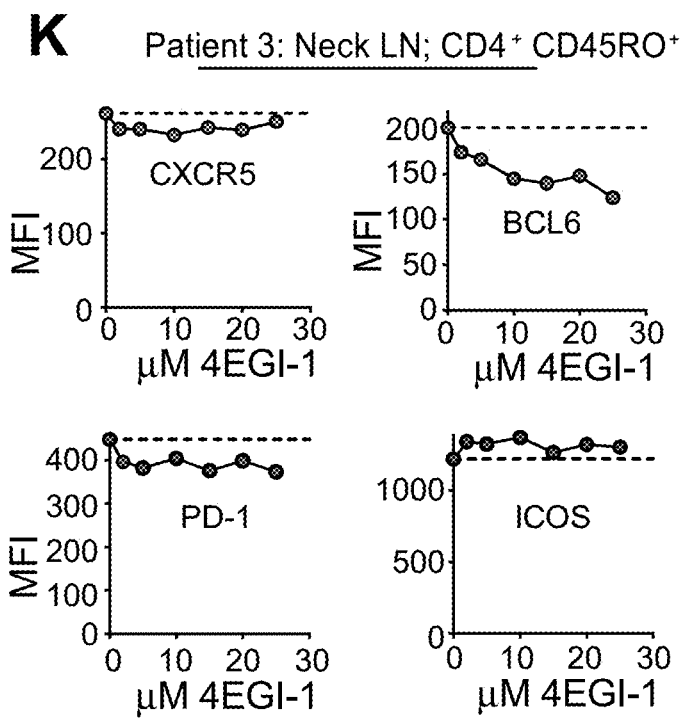
Figures 10L, 10M, 10N, 10O:
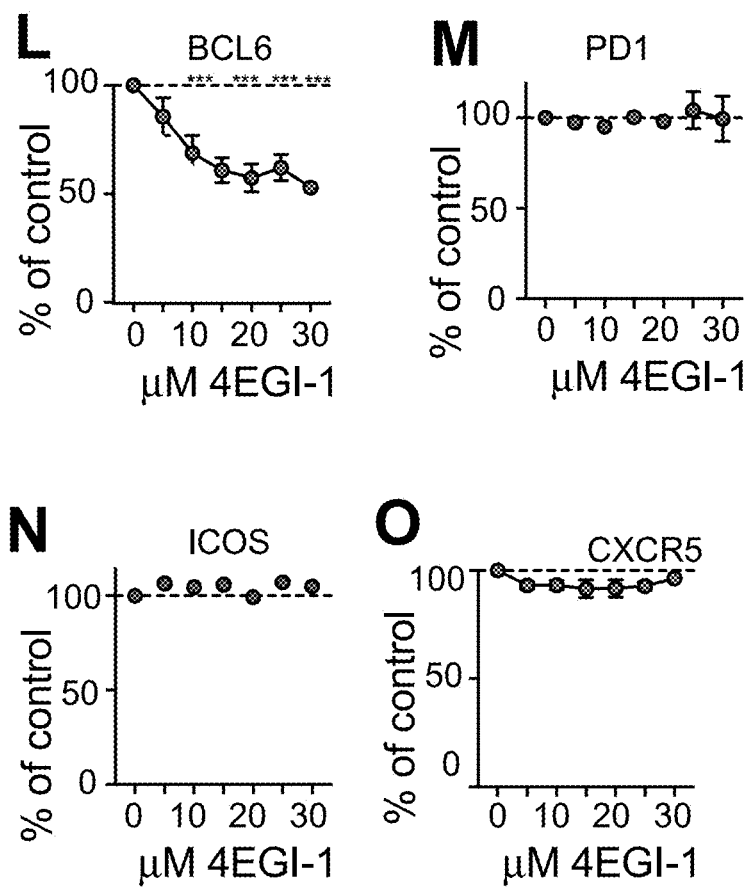

Example 6—Partial eIF4E Inhibition Causes Immediate Decline in Human and Mouse CD4+ T Cell BCL6 Levels FACS-isolated CD4+ lymphocytes from immunized mice were treated with 4EGI-1 from 10-25 µM and the effect on protein synthesis and viability quantified after placing cells in culture. 4EGI-1 reduced protein synthesis by 3-4 fold between 10-25 µM without reducing cell viability (FIGS. 10A-10B). Whereas levels of PD-1, CXCR5, and ICOS proteins were unchanged with a short time course of eIF4E inhibition, BCL6 protein levels were reduced ~3-fold, demonstrating a requirement for continuous BCL6 mRNA translation to maintain BLC6 protein levels (FIGS. 10C-10F). This is consistent with a short half-life of BCL6 protein (Webb et al., "Signals that Drive T Follicular Helper Cell Formation," *Immunology* 152:185-194 (2017), which is hereby incorporated by reference in its entirety). To examine human TFH cells, reactive non-malignant human lymph node biopsy samples containing TFH cells were obtained, FACS isolated (CD4$^+$ CD45RO$^+$ PD1$^+$ CXCR5$^+$ BCL6$^+$ ICOS$^+$) (FIGS. 10G-10H), and treated in short-term culture with 4EGI-1 (FIGS. 10I-10K). Three independent specimens from three different patients showed rapidly reduced levels of BCL6 protein but not CXCR5, ICOS, or PD-1 in activated lymph node CD4$^+$ T cells treated with 4EGI-1, with no effect on cell viability (FIGS. 10L-10O).

Figures 11A, 11B, 11C, 11D, 11E:
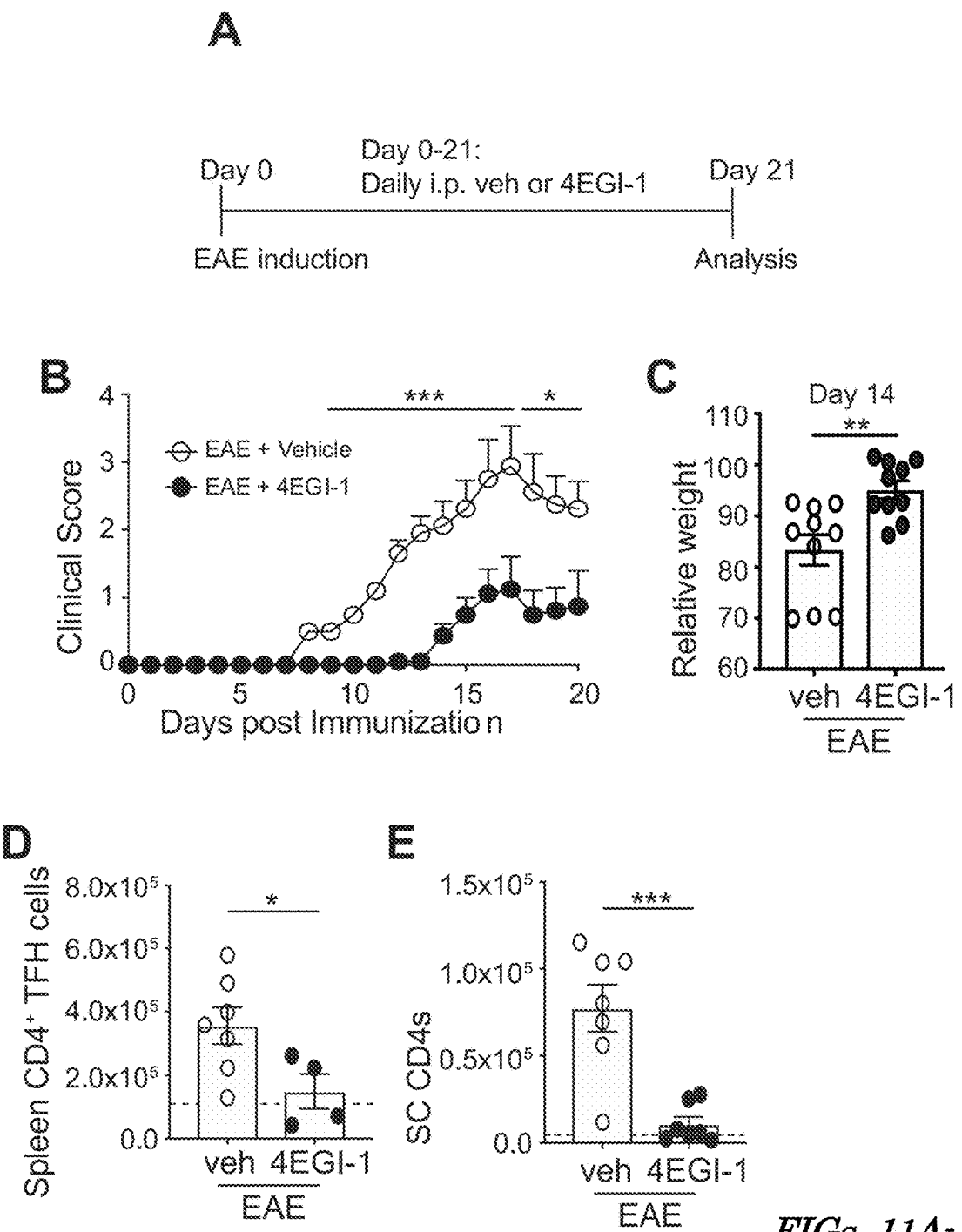
FIGS. 11A-11N show that onset, progression, and pathogenesis of EAE disease are blocked by only partial inhibition of eIF4E.
FIG. 11B is a graph showing daily clinical scores of EAE mice treated with vehicle or 4EGI-1.
FIG. 11C is a graph showing relative weight loss of animals at 14 days following onset of EAE disease.
FIGS. 11D-11H are graphs showing quantification at day 21 of EAE for spleen CD4+ TFH cells (FIG. 11D), spinal cord (SC) CD4+ T cells (FIG. 11E), SC percentage of CD4+ T cells (FIG. 11F), SC CD4+ T cells expressing IFN-γ+ (FIG. 11G), and IL-17A+ (FIG. 11H).
Figures 11F, 11G, 11H, 11I, 11J, 11K:
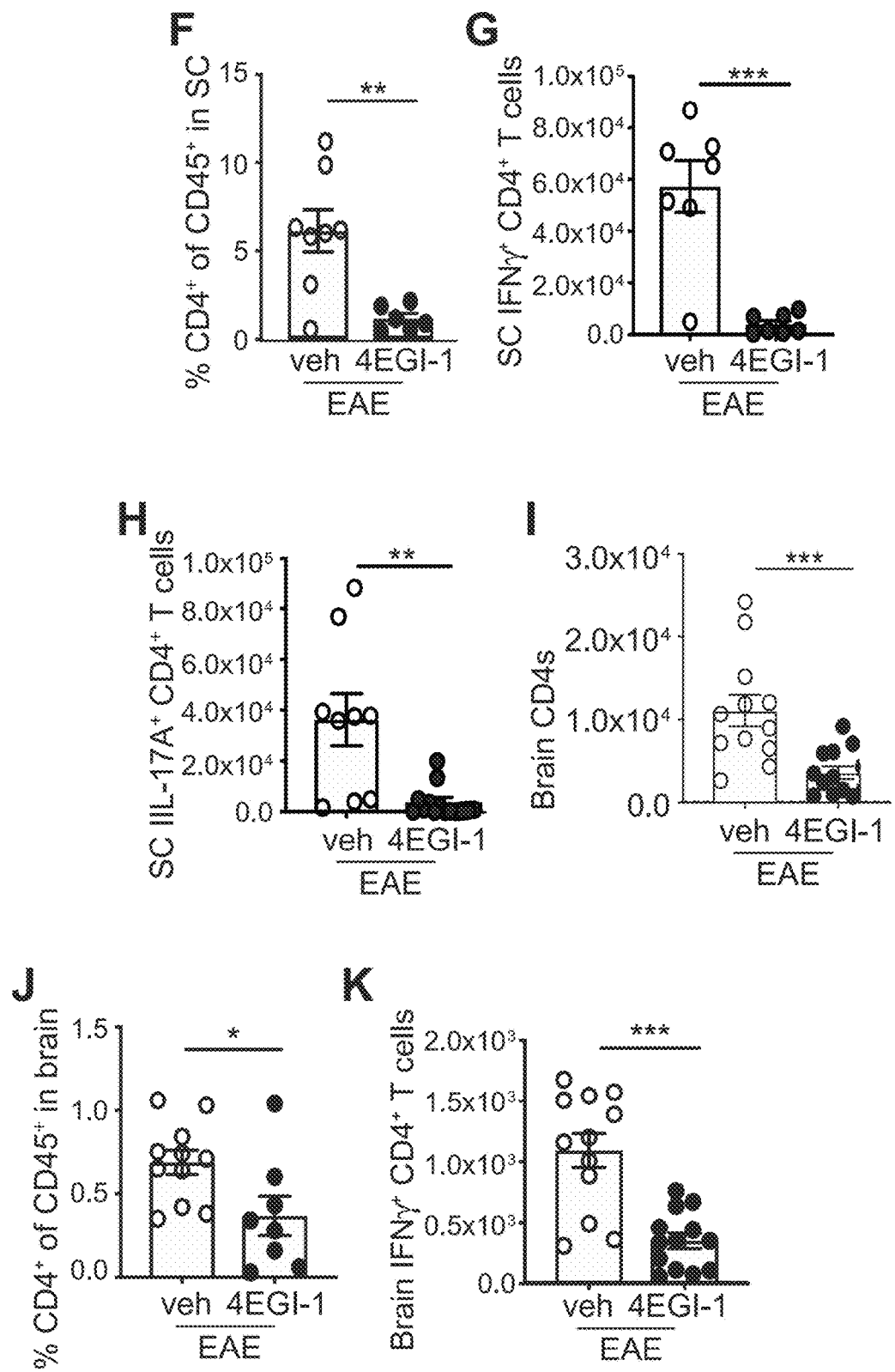
FIGS. 11I-11L are graphs showing quantification in brain at day 21 of EAE for CD4+ TFH cells in brain (FIG. 11I), percentage of CD4+ T cells (FIG. 11J), CD4+ T cells expressing IFN-γ+ (FIG. 11K), and IL-17A+ (FIG. 11L).
Figure 11L:
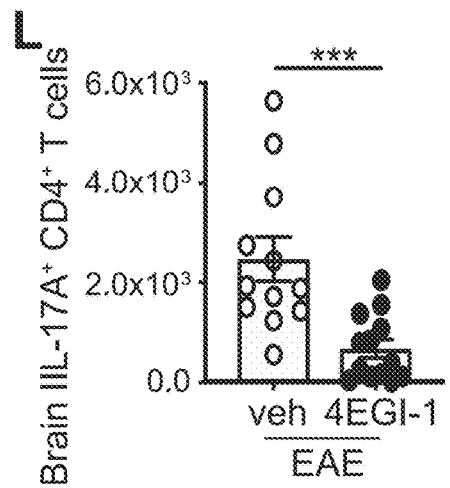
Figure 11M:
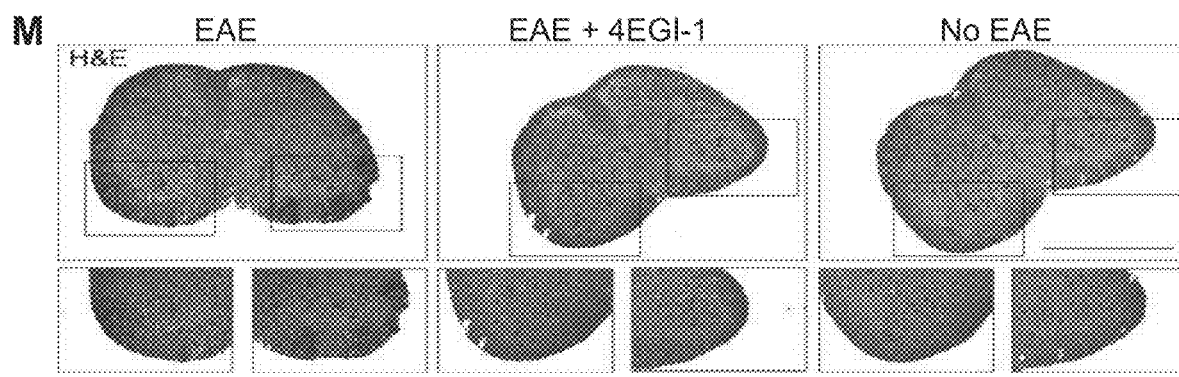
FIG. 11M are representative H&E stained cross-sections of spinal cords. Clusters of blue nucleoli identify cell infiltration. Scale bar, 500 microns.
Figure 11N:
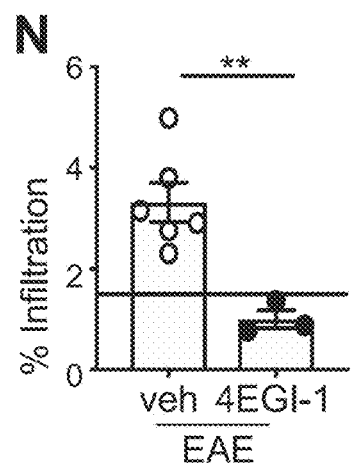
Figures 12A, 12B, 12C, 12D, 12E:
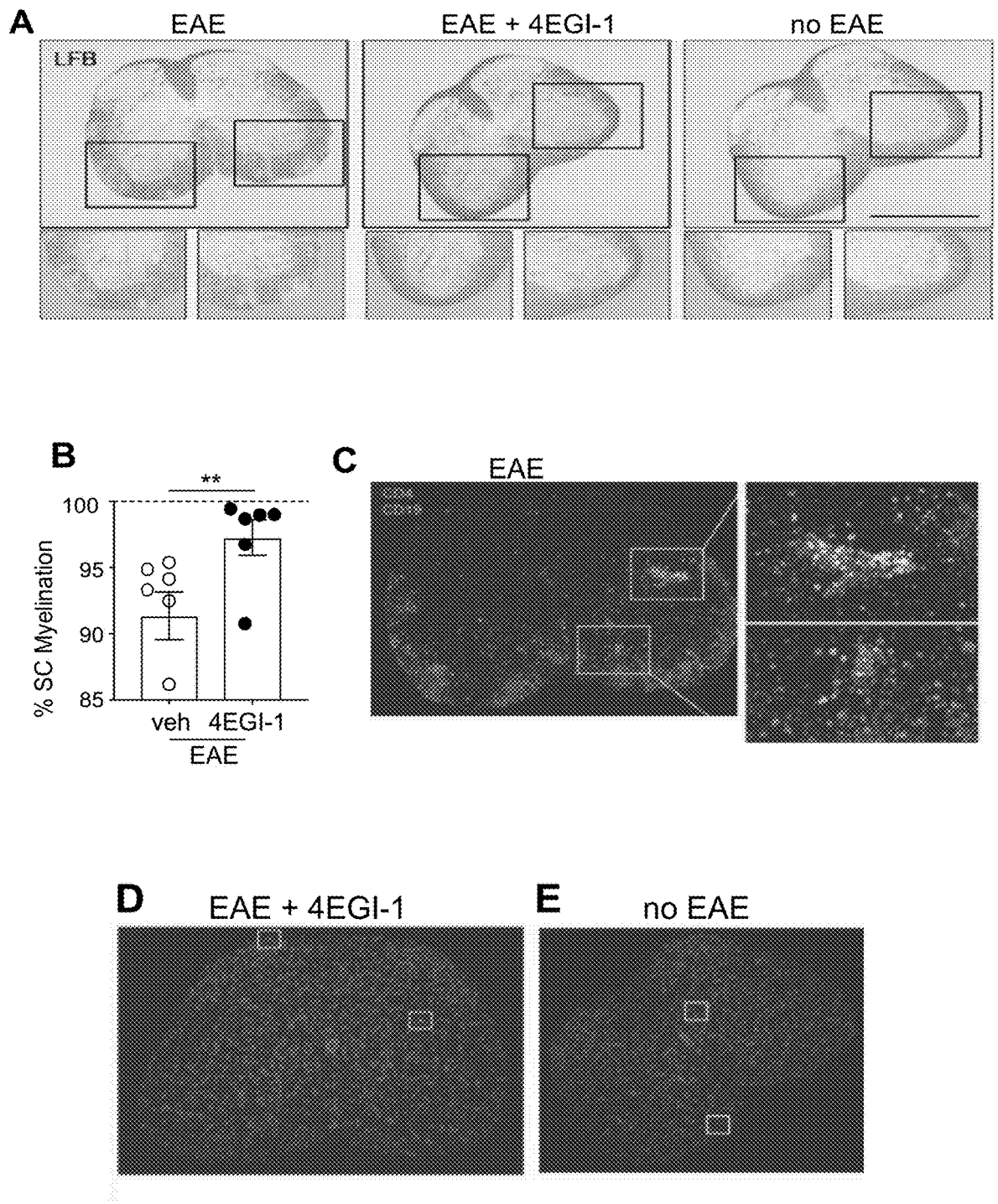
FIGS. 12A-12E demonstrate the inhibition of demyelination in EAE disease and CNS ELF formation by partial inhibition of eIF4E.

Example 7—Onset, Progression, and Pathogenesis of EAE Disease and CNS ELF Formation are Blocked by Partial Inhibition of eIF4E TFH cells are implicated in the pathogenesis of EAE but their causal role is not fully established. With the ability to pharmacologically block TFH cell development by down-regulating eIF4E activity, the impact of partial eIF4E inhibition on development of EAE, CNS ELFs, and inhibition of spinal cord demyelination was investigated. Active EAE was induced with MOG$_{33-55}$/CFA injections. Next, animals were treated with vehicle or 4EGI-1 from the time of initiation of EAE throughout progression (FIG. 11A). Mice receiving 4EGI-1 exhibited significantly reduced clinical EAE severity (FIG. 11B) and disease-associated weight loss (FIG. 11C). Partial inhibition of eIF4E reduced by 3-fold TFH cells in the spleen (FIG. 11D), as well as CD4$^+$ T cells in the spinal cord and brain, including those producing IFN-γ or IL-17A which were almost abolished (FIGS. 11E-11L). Importantly, 4EGI-1 reduction of eIF4E activity during EAE prevented demyelination of the spinal cord, with treated animals displaying near-normal levels of myelination (~98%) (FIGS. 12A-12B). Formation of ELFs is characterized by clusters of CD4$^+$ T and B cells in the spinal cords of EAE mice. ELFs were substantially reduced by treatment with 4EGI-1 in EAE mice, coincident with strongly reduced numbers of CD4$^+$ T and B cells that were abundant in EAE control untreated mice in the spinal cords, and were not proximal to each other in clusters (FIGS. 12C-12E). Thus, higher levels of eIF4E selectively program the translation of TFH cell specification mRNAs and play an important role in promoting pathogenesis of EAE disease.

Figures 13A, 13B, 13C, 13D, 13E, 13F:
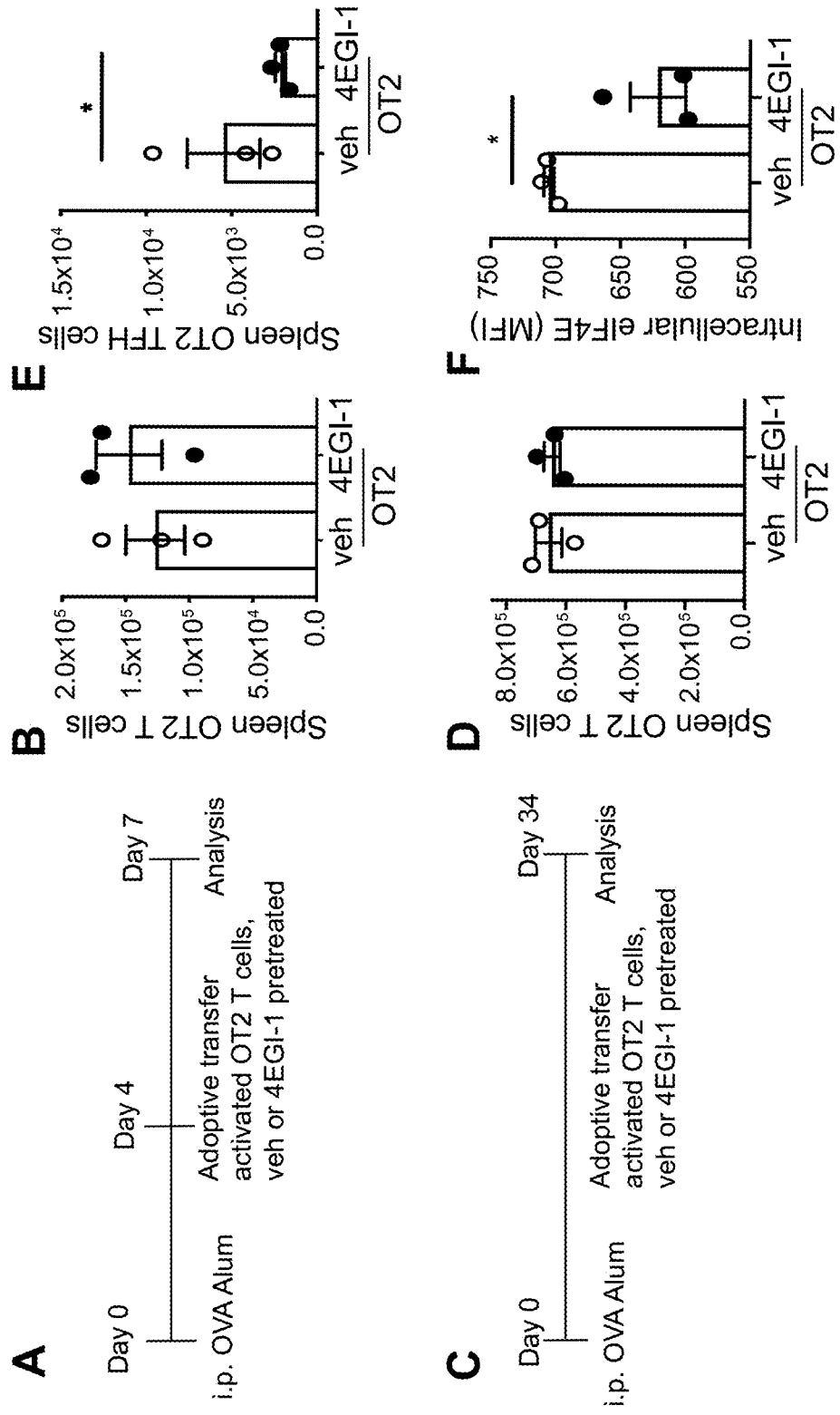

Example 8—Downregulation of eIF4E Activity Blocks TH17-Dependent ELF Formation in the CNS In a model of passive EAE, TH17-differentiated myelin-specific (2D2) CD4$^+$ T cells migrate to the spinal cord and form TFH-like cells that contribute to ELF formation (Peters et al., "Th17 Cells Induce Ectopic Lymphoid Follicles in Central Nervous System Tissue Inflammation," *Immunity* 35(6):986-996 (2011), which is hereby incorporated by reference in its entirety). This system was therefore used to determine whether higher levels of eIF4E act in a TFH cell-intrinsic manner and are essential for this specialized process. 4EGI-1 was used to downregulate eIF4E activity in OT2 T cells prior to adoptive transfer into congenic animals. Isolated OT2 T cells treated with 4EGI-1 prior to adoptive transfer, populated the spleen at levels equal to that of non-treated OT2 T cells when assayed 7 days (FIGS. 13A-13B) and 34 days (FIGS. 13C-13D) post-transfer. However, 4EGI-1 treated OT2 TFH cells in the spleen were reduced in number by two-thirds following OVA/Alum immunization (FIGS. 13D-13E). In fact, when OT2 T cells were recovered as late as day 34 post-transfer (equivalent to our passive EAE endpoint), they showed sustained reduction in intracellular levels of eIF4E (FIG. 13F). eIF4E mRNA translation itself was earlier found to be sensitive to eIF4E inhibition (FIGS. 4A-4H), possibly accounting for its sustained downregulation. Next, TH17-differentiated 2D2 T cells were treated with vehicle or 4EGI-1 in vitro prior to transfer into congenic animals for induction of passive EAE (FIG. 13G). While vehicle-treated TH17-differentiated 2D2 T cells induced EAE, mice receiving 2D2 T cells pre-treated with 4EGI-1 did not develop disease (FIG. 13H). Further, TFH-like 2D2 T cells (characterized as ICOS$^{high}$) treated with 4EGI-1 were reduced by half in the spinal cord of mice (FIG. 13I). Therefore, higher levels of CD4$^+$ T cell intrinsic eIF4E-dependent translation drives EAE and TH17-dependent development of TFH-like cells in the CNS.

Figures 14A, 14B, 14C, 14D, 14E:
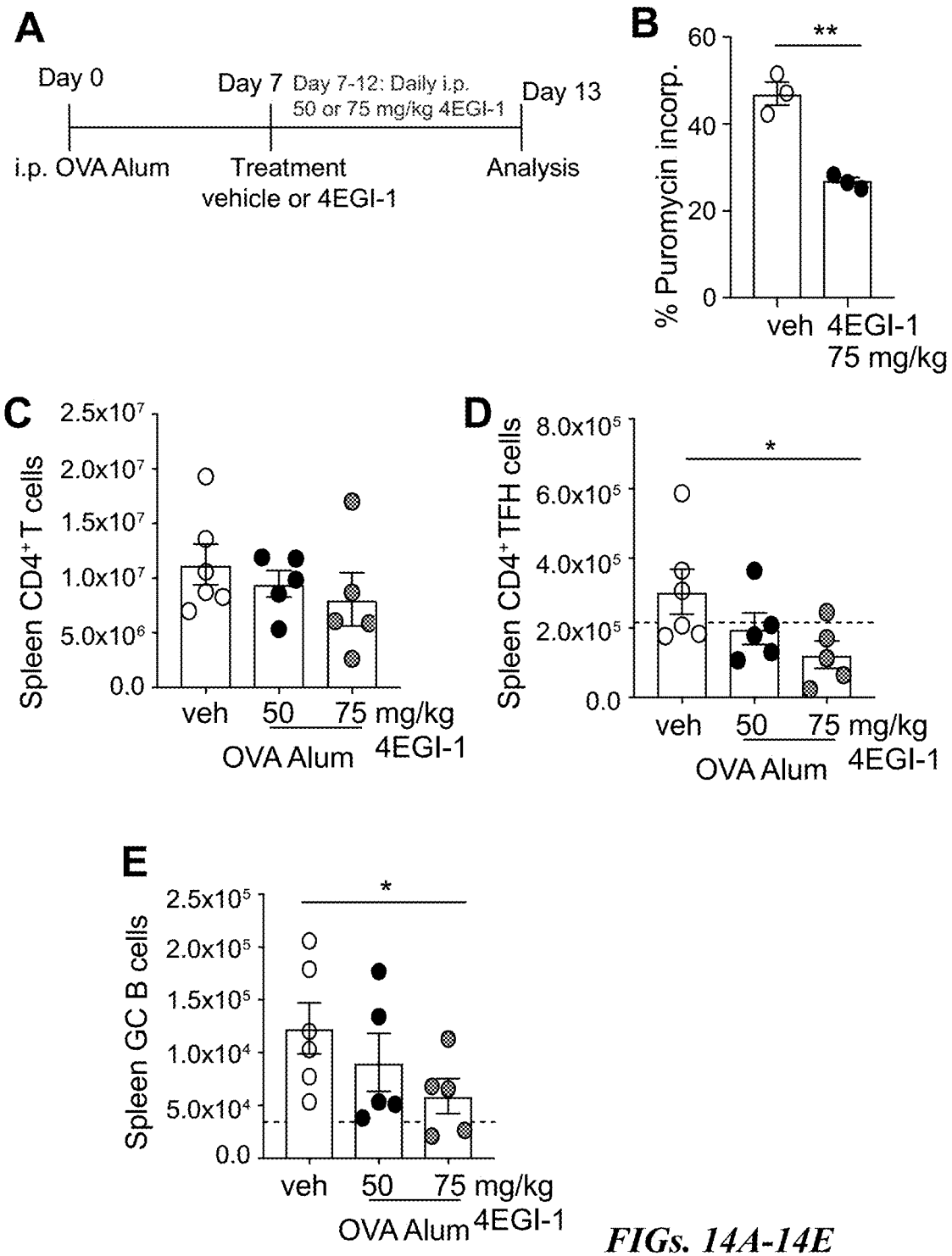

Example 9—Reduced eIF4E Activity Induces Rapid Remission and Remyelination after Development of EAE Disease Whether reducing eIF4E activity inhibits TFH cells following their differentiation and can reverse the progression of EAE disease was investigated. Mice were immunized with OVA/Alum to induce TFH cells, then following their development, treated with increasing doses of 4EGI-1 (FIG. 14A). 4EGI-1 was used at 75 mg/kg, which is still within its safety range (Sekiyama et al., "Molecular Mechanism of the Dual Activity of 4EGI-1: Dissociating eIF4G from eIF4E but Stabilizing the Binding of Unphosphorylated 4E-BP1," *Proc. Natl. Acad. Sci. USA* 112(30):E4036-E4045 (2015), which is hereby incorporated by reference in its entirety), which reduced CD4$^+$ T cell protein synthesis by approximately half (FIG. 14B), without significantly reducing the total number of CD4$^+$ T cells in spleen (FIG. 14C). However, 4EGI-1 treatment did reduce by 3-fold levels of pre-existing splenic CD4$^+$ TFH cells, GC B cells and OVA-specific IgG1 ASC cells, and moderately reduced serum OVA-specific IgG1 antibody (FIGS. 14D-14G). Therefore, the 75 mg/kg dose of 4EGI-1 was used to assess the effects of eIF4E downregulation on progression of EAE.

Figures 14F, 14G, 14H, 14I, 14J:
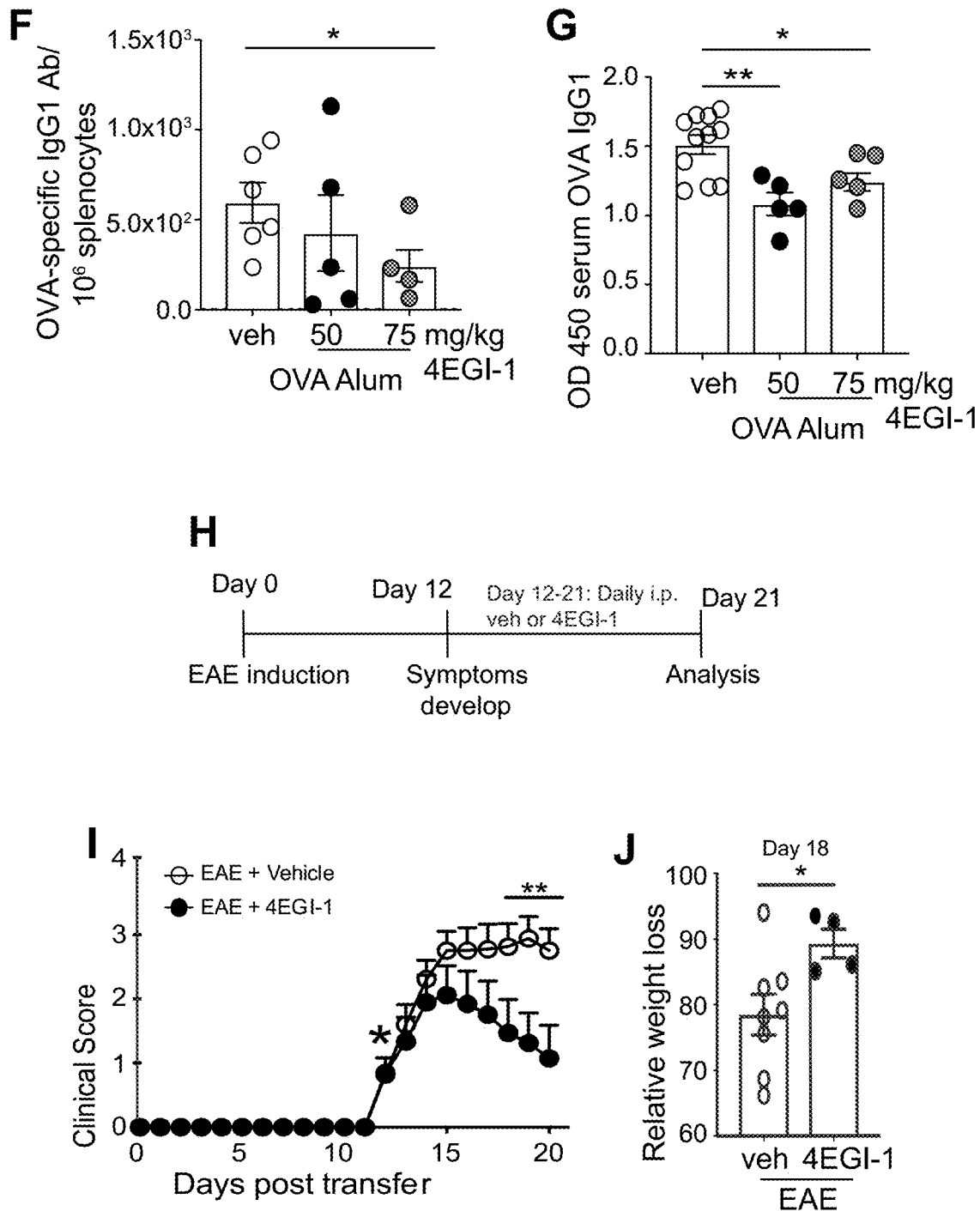
FIG. 14H is a scheme for active EAE induction and treatment with vehicle or 75 mg/kg 4EGI-1 following presentation of clinical symptoms.
FIG. 14I is a graph showing daily clinical scores of mice with EAE induction with and without 4EGI-1 treatment. * indicates beginning of treatment with 4EGI-1.
FIG. 14J is a graph showing the relative weight loss of mice at day 18.
Figure 14K:
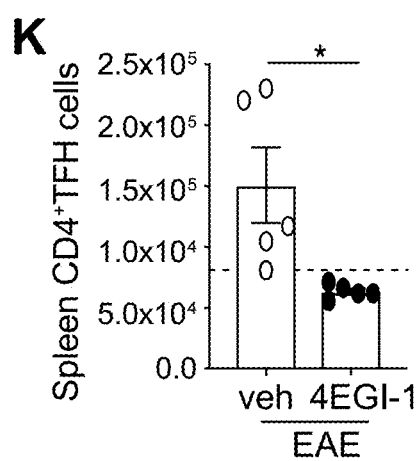
FIG. 14K is a graph showing quantification of CD4+ TFH cells in spleen at day 21 from animals with active EAE disease.
Figure 14L:
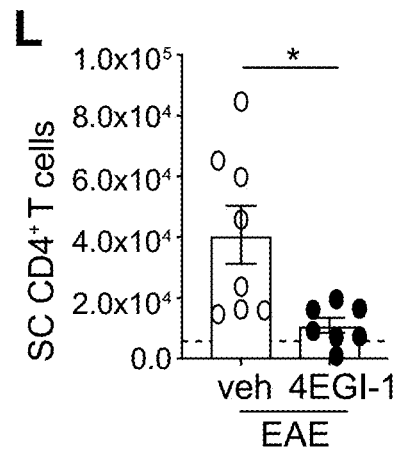
FIGS. 14L-14M are graphs showing quantification of CD4+ T cells in SC (FIG. 14L) and brain (FIG. 14M) at 21 days post-EAE.
Figure 14M:
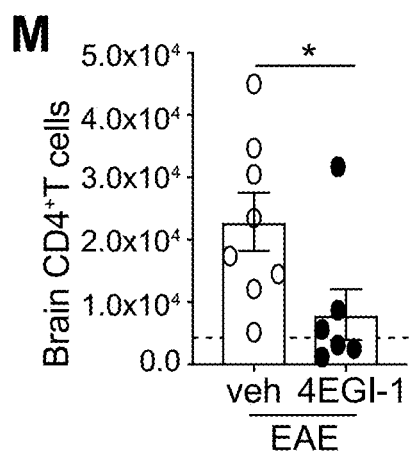
Figure 14N:
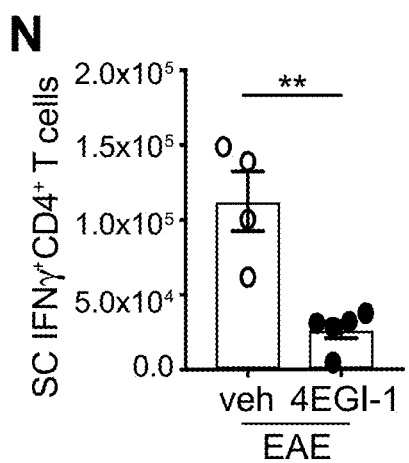
FIGS. 14N-14O are graphs showing quantification of CD4+ T cells at 21 days following EAE disease onset for expression of IFN-γ+ (FIG. 14N) or IL-17A+ (FIG. 14O) in the spinal cord.
Figure 14O:
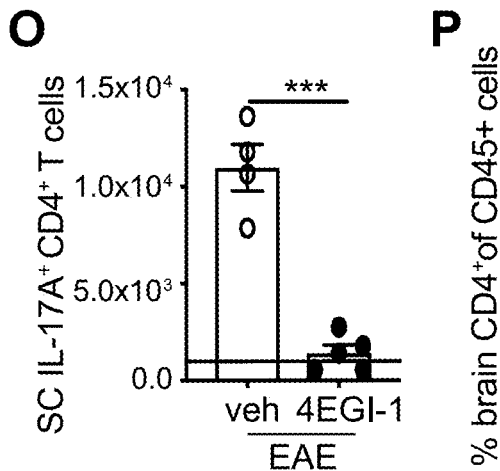
Figure 14P:
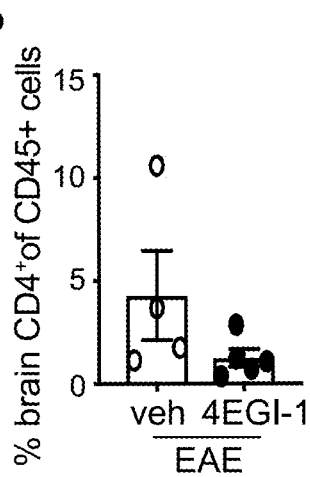
Figure 15C:
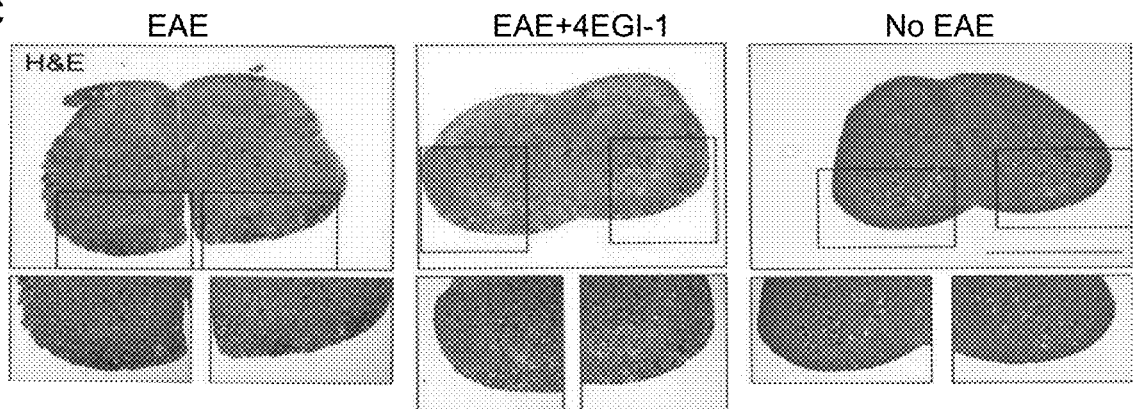
Figure 15D:
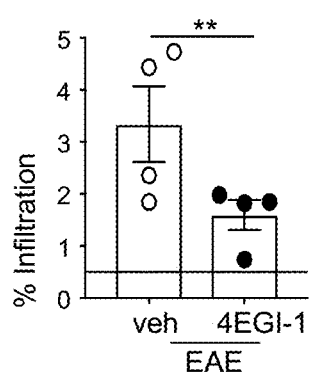
Figure 15E:
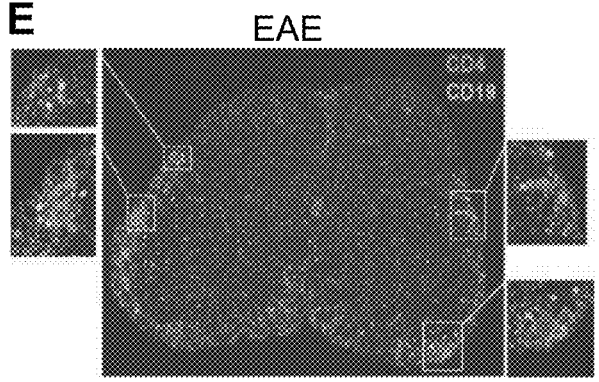
Figure 15F:
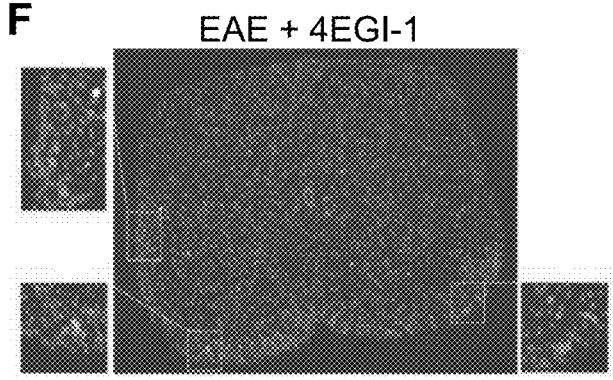
Figure 15G:
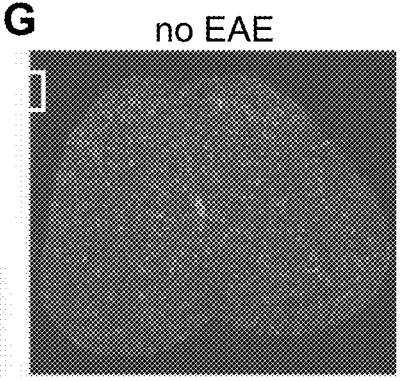

Following induction of EAE with MOG$_{33-55}$/CFA injections, mice began to show symptoms 12 days following immunization (FIGS. 14H-14I). Animals were treated with vehicle or 75 mg/kg of 4EGI-1 at 12 days and clinical score was monitored (FIG. 14I). Within 2-3 days of 4EGI-1 administration, mice exhibited marked improvement in clinical symptoms, progression of disease was inhibited, and mice entered remission by day 15 compared to vehicle-treated mice that progressed (FIG. 14I). 4EGI-1 treated mice also increased their weight compared to vehicle-treated animals (FIG. 14J). Reduced EAE disease was associated with 3-fold decreased levels of splenic TFH cells (FIG. 15K), and 4-fold decreased infiltration and retention of CD4$^+$ T cells in spinal cord and brain (FIGS. 14L-14M), including those producing IFN-γ or IL-17A (FIGS. 14N-14R). Remarkably, demyelination in mice treated with 4EGI-1, even after initiation of symptoms, was reduced compared to vehicle-treated mice, and previously demyelinated areas regained myelination to within 90% of normal levels (FIGS. 15A-15B). This was associated with a visibly marked reduction in spinal cord immune cell infiltration (FIGS. 15C-15D). While control mice with EAE disease displayed multiple ELFs in their spinal cord, those treated with 4EGI-1 following onset of symptoms at day 12 had smaller clusters of CD4$^+$ T cells with a lower frequency of B cells within them (FIGS. 15E-15G). Thus, only reducing the higher level of eIF4E by half after onset of disease was sufficient to block translation of TFH cell specification mRNAs, induce rapid remission, prevent progression of autoimmune disease and retention of pathogenic CNS T cells, and promote spinal cord myelination following disease onset.

Discussion of Examples 1-9

The experiments described herein relate to a new understanding regarding translational control of T helper cell function and the role of TFH cells in autoimmune disease. Using an inhibitor of eIF4E activity that is well tolerated, moderate downregulation of intrinsically higher levels of eIF4E in TFH compared to non-TFH CD4$^+$ T cells was shown to produce a selective defect in development and maintenance of TFH cells and GC B cells induced during immunization, infection, and allergy. Moreover, there were no observable perturbations in TH1, TH17, TH2, or Treg cell levels, even during induced inflammation. These findings suggest that downregulation of eIF4E activity is a plausible approach for specific amelioration of TFH cells in the autoimmune setting. The results presented herein provide five important findings regarding TFH cells, their translational regulation, and development: (1) eIF4E levels are intrinsically higher in TFH cells than CD4$^+$ T cells; (2) TFH cell development is acutely dependent on higher levels of eIF4E which confers selectively increased translation to TFH specification/differentiation mRNAs; (3) a higher level of eIF4E is essential to orchestrate TFH cell differentiation and function because it is specifically required for translation of established, canonical TFH cell fate-determining mRNAs, including CXCR5, SLAM, NFAT1/2, BCL6, and others; (4) clinically relevant pharmacologic reduction of eIF4E is well tolerated and specifically impairs TFH cell differentiation; and (5) TFH cells can be important drivers of autoimmune pathogenesis.

Translatome analysis from control and 4EGI-1 treated OVA/alum immunized mice reveal that the selective defect in TFH cells with partial downregulation of eIF4E activity is a result of reduction of transcription and translation of TFH cell-specific fate-determining mRNAs. While different mRNAs demonstrate different levels of transcriptional and/or translational downregulation, they include among others, Pou2af1 and CD28, which promote BCL6 expression (Linterman et al., "CD28 Expression is Required after T Cell Priming for Helper T Cell Responses and Protective Immunity to Infection," *eLife* 3:e03180 (2014) and Stauss et al., "The Transcriptional Coactivator Bob1 Promotes the Development of Follicular T Helper Cells Via Bcl6," *EMBO J.* 35(8):881-898 (2016), which are hereby incorporated by reference in their entirety), BCL6, and CXCR5, which promotes TFH cell function by promoting CD4$^+$ T cell migration into follicles and maintenance of these follicles. Most of the mRNAs dependent on higher levels of eIF4E only at the level of translation, are downstream of TCR signaling that regulates early TFH cell-fate determining events, such as nuclear localization of NFAT and FOXO expression, which are upstream of BCL6 expression. Certain transcription factor mRNAs are preferentially inhibited in translation by reducing the level of eIF4E activity. These mRNAs are primarily involved in expression of BCL6 and CXCR5. Additionally, expression of receptors that are essential for TFH maintenance, such as PD-1 and SLAM, require higher levels of eIF4E activity for translation of their mRNAs, and are remarkably sensitive to inhibition by fairly modest levels of eIF4E reduction. eIF4E levels and activity are therefore a critical set point for TFH cell development that impacts many points of the multi-stage, multi-factorial process of CD4$^+$ T cell differentiation and maintenance by modulating transcription and translation of key mRNAs.

The investigation into the requirement for higher levels of eIF4E in TFH cell differentiation presented herein concurs with previously published studies. For instance, BCL6-controlled regulatory networks identified calcium signaling, cytokine receptor expression, adherence junction and ECM receptor interaction as important functional categories for expression linked to TFH cell differentiation (Liu et al., "Genome-Wide Analysis Identifies Bcl6-Controlled Regulatory Networks during T Follicular Helper Cell Differentiation," *Cell Rep.* 14(7):1735-1747 (2016), which is hereby incorporated by reference in its entirety). The results presented herein demonstrate that these pathways are selectively programmed for translation of their mRNAs by higher levels of eIF4E in TFH cells and are acutely sensitive to moderate reduction in eIF4E activity. Additionally, depletion of BCL6 in CD4$^+$ T cells only impairs development of TFH cells and not other T helper cell subsets (Hollister et al., "Insights into the Role of Bcl6 in Follicular Th Cells using a New Conditional Mutant Mouse Model," *J. Immunol.* 191(7):3705-3711 (2013), which is hereby incorporated by reference in its entirety). It was found that inhibition of TFH cell-specific programs by pharmacologically reducing eIF4E activity strongly impairs BCL6, CXCR5, and other TFH cell mRNA translation but has no effect on differentiation or effector functions of other T helper cell types. While most mRNAs require eIF4E for their translation, including that encoding BCL6 (Yi et al., "The mTORC1-4E-BP-eIF4E Axis Controls de Novo Bcl6 Protein Synthesis in T Cells and Systemic Autoimmunity," *Nat. Commun.* 8(1):254 (2017), which is hereby incorporated by reference in its entirety), the results presented herein demonstrate that the selective translation of TFH cell specification mRNAs is exquisitely sensitive to and requires higher eIF4E levels, which serves to program CD4$^+$ T cell differentiation to TFH cells. Depletion of B cell eIF4E has been shown to impair in vitro immunoglobin class switching (Chiu et al., "The mTORC1/4E-BP/eIF4E Axis Promotes Antibody Class Switching in B Lymphocytes," *J. Immunol.* 202(2):579-590 (2019), which is hereby incorporated by reference in its entirety). Thus, therapeutic use of eIF4E inhibitors could synergistically block both formation of TFH cells and progressive class switching by GC B cells.

TFH cells are associated with MS and EAE disease pathogenesis, although their exact contribution to disease is not well understood. Investigation into the role of TFH cells in EAE has been confounded by many factors including lack of a TFH-specific inhibitor, T helper cell plasticity, and use of different animal models to induce EAE (active verses passive). Although BCL6 inhibitors are sometimes used to block and assess the role of TFH cells, they impair other T helper cell subtypes that express low levels of BCL6 during activation (Hatzi et al., "BCL6 Orchestrates Tfh Cell Differentiation Via Multiple Distinct Mechanisms," *J. Exp. Med.* 212(4):539-553 (2015), which is hereby incorporated by reference in its entirety). Moreover, the high levels of BCL6 in TFH cells require high concentrations of inhibitor which introduces toxicity. Use of an eIF4E inhibitor is more feasible, as low levels of eIF4E inhibition dramatically reduce TFH cell development and function by inhibiting translation of key TFH cell differentiation mRNAs including BCL6, without affecting differentiation and function of other T helper cell types.

It was important to assess the contribution of eIF4E to TFH cell function in both active and passive models of EAE. In active EAE, where mice are immunized with MOG/CFA, TFH cells were found in increased frequencies in secondary lymphoid organs such as spleen and lymph nodes, as well as within ELFs in the CNS (Guo et al., "T Follicular Helper-Like Cells are Involved in the Pathogenesis of Experimental Autoimmune Encephalomyelitis," *Front. Immunol.* 9:944 (2018), which is hereby incorporated by reference in its entirety). However, in the absence of a specific TFH cell inhibitor, it was previously not possible to establish whether the contribution of TFH cells to disease is correlative or causative. In a recent study, BCL6$^{fl/fl}$×CD4$^{cre}$ mice were used to demonstrate that TFH cells contribute to clinical score in active EAE, although the effects on T cell infiltration into the CNS, demyelination and ELFs, due to loss of TFH cells were not explored (Guo et al., "T Follicular Helper-Like Cells are Involved in the Pathogenesis of Experimental Autoimmune Encephalomyelitis," *Front. Immunol.* 9:944 (2018) and Quinn et al., "Role of TFH Cells in Promoting T Helper 17-Induced Neuroinflammation," *Frontiers in Immunology* 9:382 (2018), which are hereby incorporated by reference in their entirety). The studies presented herein demonstrate that downregulation of eIF4E-dependent mRNA translation, whether initiating at induction of EAE or subsequent to disease onset, results not only in significantly improved clinical score, but also reduced infiltration of CD4$^+$ T cells into the CNS, including TH1 and TH17 cells, which inhibited formation of ELFs in the spinal cord and blocked demyelination. Importantly, pharmacologic reduction of eIF4E activity following onset of EAE symptoms also rapidly induced remission, and quite remarkably, resulted in striking remyelination of the spinal cord. It is therefore believed that the major impact of eIF4E inhibition on symptoms following EAE development is the inability of TFH cells to translate mRNAs required for TFH cell retention within follicles (CXCR5) and maintain B cell contact (PD-1, SLAM). Overall, the results presented herein demonstrate that in active EAE, TFH cells significantly contribute to clinical disease, establishment of CNS ELFs, recruitment and maintenance of pathogenic T cells in the CNS and spinal cord demyelination, all of which are dependent on selective mRNA translation.

In passive EAE, where only MOG-specific T cells are transferred to induce EAE, TFH cells appear to play several roles. First, transferred MOG-specific TFH cells on their own do not induce EAE. Instead, donor MOG-specific TH17 cells differentiate into TFH-like cells and promote the differentiation of host TFH-like cells in the CNS, where ELFs are induced. Both host and transferred TFH cells likely contribute to continued TH17-dependent disease pathogenesis, as indicated by reduction in disease severity with anti-CXCL13 treatment, a ligand for CXCR5 (Peters et al., "Th17 Cells Induce Ectopic Lymphoid Follicles in Central Nervous System Tissue Inflammation," *Immunity* 35(6): 986-996 (2011) and Quinn et al., "Role of TFH Cells in Promoting T Helper 17-Induced Neuroinflammation," *Frontiers in Immunology* 9:382 (2018), which are hereby incorporated by reference in their entirety). To complement these studies, eIF4E deficiency was confined to the TH17-differentiated 2D2 T cell compartment and it was asked whether higher levels of eIF4E contribute to TFH-like differentiation from TH17 cells in the CNS. 4EGI-1 pretreated TH17 cells failed to induce EAE and form TFH cells, which further demonstrates that the level and activity of eIF4E governs TFH cell differentiation. These studies provide a potential therapeutic intervention for MS and other autoimmune diseases that involve TFH cells, including lupus, rheumatoid arthritis, and type 1 diabetes, by using pharmacologic downregulation of eIF4E activity.

Finally, while transcriptomic analysis has led to a better understanding of lymphocyte biology and function, how translational control governs T cell commitment of differentiation to different lineages, maintenance of the differentiated state, and function is just beginning to be understood. While canonical TFH programs, such as CD28-dependent BCL6 expression, were shown to be modulated at the level of selective mRNA translation, non-canonical mRNAs that are transcriptionally and/or translationally increased in expression by higher levels of eIF4E that are enriched in TFH cells that may also play important roles in their development and function were also identified. While some of these mRNAs are involved in broad programs that impact on TFH cell development and function, including angiogenesis and metastasis, others are involved in well-established TFH cell development pathways such as MAPK signaling, metabolism, and formation of gap junctions. Thus, in addition to transcriptional regulation, translational control represents a further step of regulation that is critical for differentiation and plasticity of T cells, and confers specialized regulation to TFH cells and B cell antibody responses.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting T Follicular Helper (TFH) cell-mediated differentiation and/or activation in a subject, said method comprising:
   administering to a subject in need of treatment for an autoimmune disorder a eukaryotic translation initiation factor 4E (eIF4E) inhibitor to inhibit TFH cell-mediated differentiation and/or activation in the subject, wherein the autoimmune disorder is selected from the group consisting of multiple sclerosis (MS), rheumatoid arthritis, asthma, allergies and food allergies, anaphylactic responses, Jorgen syndrome, autoimmune encephalitis (EAE), lupus nephritis, Type I diabetes, juvenile dermatomyositis, autoimmune myasthenia gravis, autoimmune thyroid disease, atherosclerosis, and graft versus host disease.

2. The method according to claim 1, wherein the subject is a mammal.

3. The method according to claim 2, wherein the subject is a human.

4. The method according to claim 3, wherein the subject is an infant, a child, an adolescent, an adult, or a geriatric adult.

5. The method according to claim 1, wherein the eIF4E inhibitor does not directly inhibit BCL6.

6. The method according to claim 1, wherein the eIF4E inhibitor is selected from the group consisting of a reversibly binding nucleotide analogue resembling m$^7$GTP and its derivatives; a covalently binding inhibitor to the eIF4E m$^7$GTP (cap) binding site; an inhibitor of eIF4E binding of eIF4E to eIF4G; an antisense RNA and antisense oligonucleotide (ASO) to eIF4E; Ribavarin and compounds that share similar structure to 7-methyl-GTP; a 7-methyl-GMP and analogues and derivatives thereof; and an inhibitor that uses 4E binding protein mimetic peptides to bind and block eIF4E.

7. The method according to claim 1, wherein the eIF4E inhibitor is selected from the group consisting of 4EGI-1, 4Ei-1, eFT-4Ei-1, eFT-4Ei-2, eFT-4Ei-3, 4Ei10, 4EIR-Cat, ribavirin, a 4EBP mimetic peptide, Bn7GMP, and derivatives thereof.

8. The method according to claim 1, wherein the eIF4E inhibitor is a nucleic acid molecule.

9. The method according to claim 8, wherein the nucleic acid molecule encodes an antisense oligonucleotide (ASO), siRNA, shRNA, or miRNA molecule.

10. The method according to claim 1, wherein the eIF4E inhibitor is eIF4E ASO LY2275796.

11. The method according to claim 1, wherein said administering is effective to inhibit TFH cell-mediated B-cell differentiation in the subject.

12. The method according to claim 1, wherein said administering is effective to inhibit TFH cell-mediated activation of TH17 cells in the subject.

13. The method according to claim 1, wherein said administering is effective to inhibit TFH cell-mediated differentiation and/or activation in the subject without inducing toxicity in the subject.

14. The method according to claim 1, wherein said administering is effective to inhibit TFH cell-mediated differentiation and/or activation in the subject with less toxicity than when said administering is carried out with a BCL6 inhibitor.

15. The method according to claim 1, wherein said administering does not directly disrupt or inhibit the differentiation of other T cell types selected from THI, TH2, THI7, and regulatory T (Treg) cells.

* * * * *